(12) United States Patent
Fallin et al.

(10) Patent No.: US 7,566,339 B2
(45) Date of Patent: Jul. 28, 2009

(54) ADJUSTABLE LINE LOCKS AND METHODS

(75) Inventors: T. Wade Fallin, Hyde Park, UT (US); M. Mary Sinnott, Logan, UT (US)

(73) Assignee: IMDS., Logan, UT (US)

( * ) Notice: Subject to any disclaimer, the term of this patent is extended or adjusted under 35 U.S.C. 154(b) by 818 days.

(21) Appl. No.: 10/936,376

(22) Filed: Sep. 7, 2004

(65) Prior Publication Data

US 2005/0288709 A1 Dec. 29, 2005

Related U.S. Application Data

(63) Continuation-in-part of application No. 10/459,375, filed on Jun. 11, 2003, now Pat. No. 7,150,757.

(51) Int. Cl.
- *A61B 17/04* (2006.01)
- *A61B 17/82* (2006.01)
- *A61B 17/53* (2006.01)
- *F16G 11/00* (2006.01)

(52) U.S. Cl. .......... 606/232; 606/74; 606/103; 24/129 R

(58) Field of Classification Search .......... 606/232, 606/74, 103, 222; 24/114.7, 115 R, 129 R, 24/130, 129 B, 129 W; 289/1.2, 13, 14
See application file for complete search history.

(56) References Cited

U.S. PATENT DOCUMENTS

| | | | | |
|---|---|---|---|---|
| 757,820 | A * | 4/1904 | Lykke | .......... 24/130 |
| 1,452,338 | A | 4/1923 | Flowers | |
| 1,610,309 | A * | 12/1926 | Niederer | .......... 24/114.7 |
| 1,806,162 | A | 5/1931 | Hahn | |
| 2,025,663 | A * | 12/1935 | Iuliano | .......... 24/114.7 |
| 2,441,336 | A | 5/1948 | Sova | |
| 2,543,056 | A * | 2/1951 | Pollack et al. | .......... 24/114.7 |
| 3,409,014 | A | 11/1968 | Shannon | |
| 3,678,543 | A | 7/1972 | Hobbs | |
| 3,715,782 | A | 2/1973 | Newell | |
| 3,785,009 | A | 1/1974 | Nysten | |
| 3,880,166 | A | 4/1975 | Fogarty | |

(Continued)

FOREIGN PATENT DOCUMENTS

EP     861050 B1     6/2004

(Continued)

*Primary Examiner*—Julian W Woo
(74) *Attorney, Agent, or Firm*—David W. Meibos; Barbara Daniels; Daniel F. Justin

(57) ABSTRACT

A line lock includes a body at least partially bounding a primary passageway, a secondary passageway, and a working passageway. The passageways may be sized to receive two locking portions of a suture such that each of the locking portions can only be moved through the line lock along one direction. The passageways may be symmetrically arranged to receive the two locking portions in symmetrical fashion. The passageways may also be arranged such that two ends of the suture can be drawn in substantially opposite directions to advance the body along the suture. The body may have one or more grooves into which corresponding portions of the suture can be pressed via tension in the suture to enhance locking. The body may have a generally circular profile that facilitates advancement of the body along the suture to tighten the suture against, for example, internal bodily tissue.

29 Claims, 38 Drawing Sheets

U.S. PATENT DOCUMENTS

| | | | |
|---|---|---|---|
| 3,910,281 | A | 10/1975 | Kletschka et al. |
| 3,976,079 | A | 8/1976 | Samuels et al. |
| 4,034,443 | A | 7/1977 | Turner |
| 4,105,349 | A | 8/1978 | Kupperman et al. |
| 4,280,435 | A | 7/1981 | Loomis |
| 4,477,947 | A | 10/1984 | Lyons |
| 4,480,357 | A | 11/1984 | Cummins |
| 4,480,358 | A | 11/1984 | Barling et al. |
| 4,646,394 | A | 3/1987 | Krauss |
| 4,785,509 | A | 11/1988 | Fisher |
| 4,831,692 | A | 5/1989 | Chuan |
| 4,910,934 | A | 3/1990 | Hennings |
| 4,932,962 | A | 6/1990 | Yoon et al. |
| 4,976,013 | A | 12/1990 | Wax |
| 5,030,228 | A * | 7/1991 | Wong et al. ............... 606/222 |
| 5,074,874 | A | 12/1991 | Yoon et al. |
| 5,123,913 | A | 6/1992 | Wilk et al. |
| 5,139,520 | A | 8/1992 | Rosenberg |
| 5,210,911 | A | 5/1993 | Brown |
| 5,284,485 | A | 2/1994 | Kammerer et al. |
| 5,306,301 | A | 4/1994 | Graf et al. |
| 5,374,269 | A | 12/1994 | Rosenberg |
| 5,403,330 | A | 4/1995 | Tuason |
| 5,445,167 | A | 8/1995 | Yoon et al. |
| 5,527,341 | A | 6/1996 | Gogolewski et al. |
| 5,572,770 | A | 11/1996 | Boden |
| 5,601,557 | A | 2/1997 | Hayhurst |
| 5,630,824 | A | 5/1997 | Hart |
| 5,645,588 | A | 7/1997 | Graf et al. |
| 5,653,719 | A | 8/1997 | Raiken |
| 5,693,060 | A | 12/1997 | Martin |
| 5,725,556 | A | 3/1998 | Moser et al. |
| 5,741,281 | A | 4/1998 | Martin |
| 5,741,301 | A | 4/1998 | Pagedas |
| 5,752,964 | A | 5/1998 | Mericle |
| 5,759,189 | A | 6/1998 | Ferragamo et al. |
| 5,769,894 | A | 6/1998 | Ferragamo |
| 5,782,864 | A | 7/1998 | Lizardi |
| 5,839,768 | A | 11/1998 | Wackerly |
| 5,891,168 | A | 4/1999 | Thal |
| 5,931,855 | A | 8/1999 | Buncke |
| 5,950,284 | A | 9/1999 | Persson |
| 6,024,758 | A | 2/2000 | Thal |
| 6,030,007 | A | 2/2000 | Bassily et al. |
| 6,045,574 | A | 4/2000 | Thal |
| 6,066,160 | A | 5/2000 | Colvin et al. |
| 6,095,282 | A | 8/2000 | Sadeck |
| 6,106,545 | A | 8/2000 | Egan |
| 6,132,439 | A | 10/2000 | Kontos |
| 6,171,317 | B1 | 1/2001 | Jackson et al. |
| 6,241,749 | B1 * | 6/2001 | Rayhanabad ............... 606/232 |
| 6,319,271 | B1 | 11/2001 | Schwartz et al. |
| 6,432,123 | B2 | 8/2002 | Schwartz et al. |
| 6,485,065 | B2 | 11/2002 | Lusk et al. |
| 6,533,802 | B2 | 3/2003 | Bojarski et al. |
| 6,652,561 | B1 | 11/2003 | Tran |
| 6,749,616 | B1 | 6/2004 | Nath |
| 6,770,076 | B2 | 8/2004 | Foerster |
| 2002/0123758 | A1 | 9/2002 | Bachman et al. |
| 2004/0015171 | A1 | 1/2004 | Bojarski et al. |
| 2004/0098053 | A1 | 5/2004 | Tran |
| 2004/0133217 | A1 | 7/2004 | Watschke |
| 2004/0133238 | A1 | 7/2004 | Cerier |
| 2004/0133239 | A1 | 7/2004 | Singhatat |
| 2004/0138683 | A1 | 7/2004 | Shelton et al. |
| 2004/0138706 | A1 | 7/2004 | Abrams et al. |
| 2004/0153103 | A1 | 8/2004 | Schwartz et al. |
| 2007/0233241 | A1 | 10/2007 | Graf et al. |

FOREIGN PATENT DOCUMENTS

| | | |
|---|---|---|
| EP | 1430840 A2 | 6/2004 |
| GB | 2 046 826 A | 11/1980 |
| JP | 6-114067 | 4/1994 |
| WO | WO2004062506 A1 | 7/2004 |

* cited by examiner

ADJUSTABLE LINE LOCKS AND METHODS

CROSS-REFERENCE TO RELATED APPLICATIONS

This application is a C.I.P. of U.S. patent application Ser. No. 10/459,375, filed on Jun. 11, 2003 now U.S. Pat. No. 7,150,757 and entitled ADJUSTABLE LINE LOCKS AND METHODS, the disclosure of which is incorporated herein by reference.

BACKGROUND OF THE INVENTION

1. The Field of the Invention

The present invention relates generally to devices to replace knots and more specifically to devices to replace surgical knots tied in open, arthroscopic, and endoscopic procedures.

2. The Relevant Technology

Numerous devices have been developed to eliminate the need to tie knots as a way of securing a line. The devices that accomplish the same function as a knot, which is in part to secure a line to retain tension in a portion of the line, are typically referred to as line locks.

Line locks generally operate in one of two ways. Some line locks are manually actuated to secure one or more lines so that tension is maintained in a portion of the line(s). Once actuated, the line lock resists sliding along the line(s) either toward or away from the tensioned portion of the line. Other line locks are continuously adjustable in one direction so that tension is increased in the portion of the line upon which the line lock is advanced. The continuously adjustable line locks resist movement away from the tensioned portion of the line, but can be further advanced toward the tensioned portion of the line with an appropriately applied force.

The portion of a line that is put under tension, typically to secure some object, is commonly referred to as the standing end. The portion of the line that extends toward the line handler is commonly referred to as the working end. A knot in a line, or a line lock attached to a line, is the demarcation between the standing end and the working end.

Continuously adjustable line locks offer several advantages. They are passive locking devices, meaning that no other operation is required to secure the line lock once it is moved along the line to its desired position. Furthermore, these line locks can be used to continuously increase the tension in the standing end until it reaches a desired level of tension.

The advantages of line locks over tied knots are very attractive in many varied applications, including the use of surgical sutures. However, the line locks developed to date have many deficiencies when considered for surgical suture applications. For example, known line locks use line on line friction to create the locking effect, and this line on line friction makes it difficult to advance the line lock over suture. Known line locks rely on maintenance of tension in the standing end to prevent the line lock from migrating back along the working end.

In surgical suture applications, the working end is typically trimmed closely to the line lock. As a result, the line lock can easily disassociate from the suture once tension in the standing end is lost. In most, if not all, surgical applications, a free-floating device such as a line lock can potentially harm adjacent body tissues. Additionally, known line locks are susceptible to loosening during cyclic variations in the tension of the standing end. This cyclic variation in the standing end tension is common in surgical applications as tissues are stressed and then relaxed. Loosening of the line lock thus compromises the securing function for which it was intended.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

The present invention relates to line locks that can be used in part to replace surgical knots tied in sutures in open, arthroscopic, and endoscopic procedures. By increasing the size of the line locks, it is also appreciated that the line locks can be used outside of surgical procedures for any use where it is desired to selectively adjust and/or tie off a line such as a rope, cord, string, or other conventional type of line.

Figure 1:
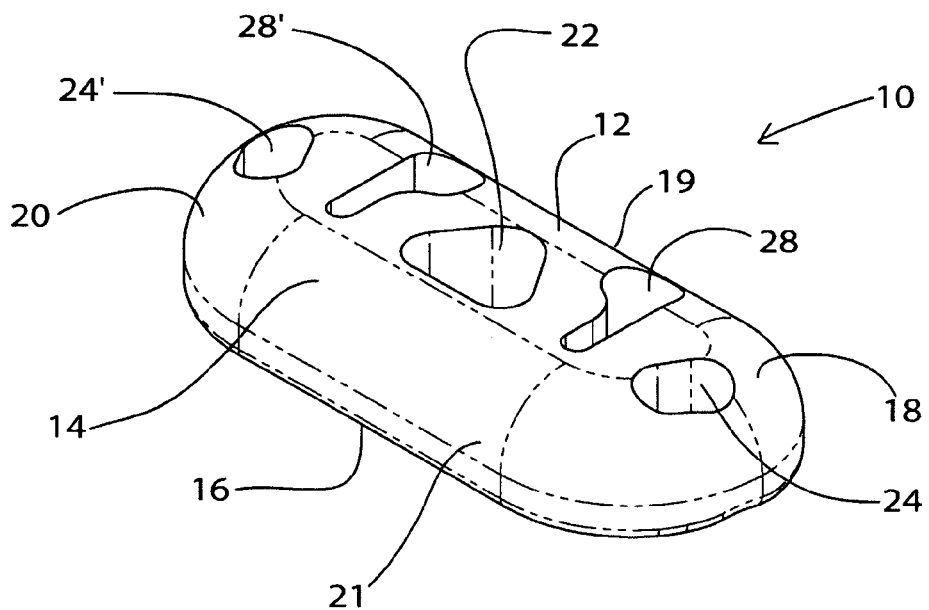
FIG. 1 is a perspective view of an adjustable line lock.

Depicted in FIG. 1 is one embodiment of a line lock 10 incorporating features of the present invention. Line lock 10 comprises an elongated body 12 having a top surface 14 and an opposing bottom surface 16 that each extend between a first end 18 and an opposing second end 20. Body 12 also has a first side 19 and an opposing second side 21 extending between first end 18 and second end 20. In the embodiment depicted, body 12 has a substantially rectangular configuration with rounded ends. As will be apparent from the following disclosure, however, body 12 can be any desired configuration such as triangular, circular, square or any other polygonal or irregular configuration.

In typical surgical applications, body 12 has a maximum dimension D along its length (FIG. 2) which is typically less than about 2 cm, more commonly less than about 1.5 cm, and even more commonly less than about 1 cm. Other dimensions can also be used. By way of example and not by limitation, in one embodiment body 12 has a height in a range between about 1 mm to about 1.5 mm, a width in a range between about 2 mm to about 3 mm, and length D in a range between about 5 mm to about 8 mm. In non-surgical applications, body 12 can be any desired dimension. For example, maximum dimension D can be in a range from about 5 cm to about 0.5 m. Again, other dimensions can also be used.

For use in surgical applications, body 12 can be comprised of any biocompatible material. The biocompatible material can be bioabsorbable or non-bioabsorbable. Examples of typical materials include non-bioabsorbable plastic, bioabsorbable plastic, synthetic tissue, and allograft tissue. In non-surgical applications, body 12 can be made of any desired material such as metal, plastic, wood, fiberglass, composite, or the like.

As depicted in FIG. 1, centrally extending through body 10 between top surface 14 and bottom surface 16 is a primary passageway 22. As used in the specification and appended claims, the term "passageway" is broadly intended to include closed apertures, such as depicted by primary passageway 22, partially bound apertures, open channels, recesses, grooves, slots, and the like, that are capable of receiving a line therein and at least partially retaining the line therein. The term "line" as used in the specification and appended claims is broadly intended to include suture, cord, rope, filament, wire, cable, and any other form of line.

Extending between surfaces 14 and 16 at first end 18 of body 12 is a first secondary passageway 24. A second secondary passageway 24' extends between surfaces 14 and 16 at second end 20. Extending through body 12 at a location between primary passageway 22 and first secondary passageway 24 is a first working passageway 28. In one embodiment, although not necessarily required, first working passageway 28 is disposed between primary passageway 22 and first secondary passageway 24 such that a geometric line segment 36 (FIG. 2) can be extended between primary passageway 22 and first secondary passageway 24 so that line segment 36 intersects with first working passageway 28. Similar to first working passageway 28, a second working passageway 28' extends through body 12 at a location between primary passageway 22 and second secondary passageway 24'.

Each working passageway 28 and 28' has an elongated transverse cross sectional area that extends between a first end 38 and an opposing second end 40. Each working passageway 28, 28' comprises an enlarged access region 32 at first end 38 which communicates with a constricted capture slot 34 at second end 40. Access region 32 is sized to enable easy feeding of a line into and through the corresponding working passageways 28, 28'. Accordingly, although access region 32 can be slightly smaller than the transverse cross sectional area of the line which is to be passed therethrough, access region 32 typically has a transverse cross sectional area that is equal to or slightly larger than the transverse cross sectional area of the line that is to be passed therethrough.

In contrast, capture slot 34 has a width W that is substantially equal to or less than the diameter of the line that is to be passed through working passageways 28, 28'. For example, in one embodiment width W is less than about 0.9 times the diameter of the line and more commonly less than about 0.75 times the diameter of the line. It is appreciated that working passageways 28, 28' can come in a variety of different configurations. For example, capture slot 34 can come in a variety of different constricted, tapered, or notched shaped configurations that are capable of securely retaining a line through wedged engagement. For line made of less compressible material, such as metal, the required difference between the width W and the diameter of the line may be less than the examples given above.

Figure 2:
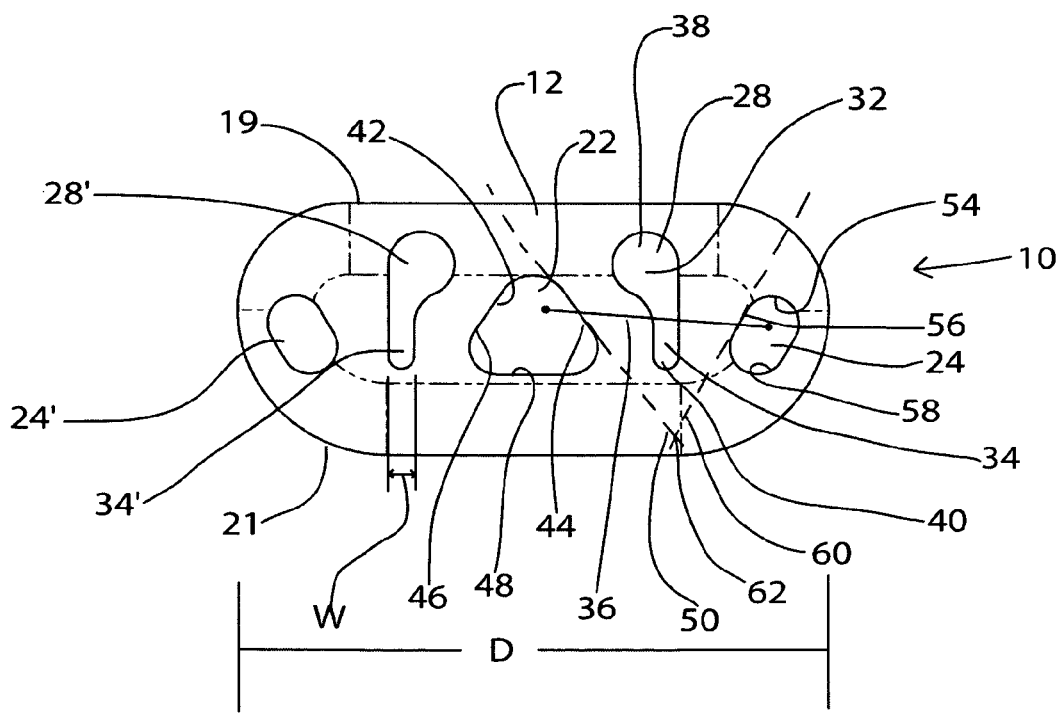
FIG. 2 is a top plan view of line lock shown in FIG. 1.

As depicted in FIG. 2, central passageway 22 is bounded by an interior surface 42 of body 12 having a substantially triangular transverse cross section. Interior surface 42 comprises a first side face 44 disposed toward first working passageway 28, a second side face 46 disposed toward second working passageway 28' and which intersects with first side face 44, and a third side face 48 extending between first side face 44 and second side face 46. Although side faces 44 and 46 are shown as being substantially flat, in alternative embodiments side faces 44 and 46 can be curved or irregular. In one embodiment, however, first side face 44 is substantially disposed in or tangent to a first plane illustrated by dashed line 50. With reference to FIG. 2, plane 50 slopes toward second end 40 of first working passageway 28 as plane 50 extends from first side 19 of body 12 to second side 21.

First secondary passageway 24 is bounded by an interior surface 54 of body 12 having an elongated transverse cross section. Interior surface 54 comprises a first side face 56 disposed toward first working passageway 28 and an opposing second side face 58. Although side faces 56 and 58 are shown as being substantially flat, in alternative embodiments side faces 56 and 58 can also be curved or irregular. Again, in one embodiment first side face 56 is substantially disposed in or tangent to a second plane illustrated by dashed line 60. With reference to FIG. 2, second plane 60 slopes toward second end 40 of first working passageway 28 as second plane 60 extends from first side 19 of body 12 to second side 21.

In the above discussed configuration, first plane 50 and second plane 60 are disposed so as to be converging as they extend from first side 19 of body 12 to second side 21. In the embodiment depicted, planes 50 and 60 intersect at a location 62 on body 12 that is at least substantially aligned with a central longitudinal axis of capture slot 34. In other embodiments, location 62 can be directly adjacent to body 12 or at a distance from body 12. Likewise, location 62 need not be aligned with the central longitudinal axis of capture slot 34. Although not required, in one embodiment planes 50 and 60 are disposed at equally opposing angles relative to the central longitudinal axis of capture slot 34. Furthermore, planes 50 and 60 can intersect so as to form an inside angle therebetween in a range between about 5° to about 85°.

Second secondary passageway 24' has substantially the same configuration as first secondary passageway 24. Likewise, second secondary passageway 24' has substantially the same relative position to second working passageway 28' and second side face 46 of primary passageway 22 as first secondary passageway 26 has to first working passageway 28 and first side face 44 of primary passageway 22. As such, the discussion with regard to planes 50 and 60 are also applicable to primary passageway 22 and second secondary passageway 24'.

By way of example of the passageways and not by limitation, for use with a size USP #2 braided suture, which has a diameter in a range between about 0.5 mm to about 0.6 mm, primary passageway 22 has a length in a range between about 1.3 mm to about 1.5 mm and a width in a range between about 1 mm to about 1.3 mm. Secondary passageways 24 and 24' have a width of about 0.8 mm and a length in a range between 1 mm to about 1.3 mm. Access region 32 of working passageways 28 and 28' have width in a range between about 0.7 mm to 1 mm while capture slots 17 have a width in a range between about 0.3 mm to 0.4 mm.

Figure 3:
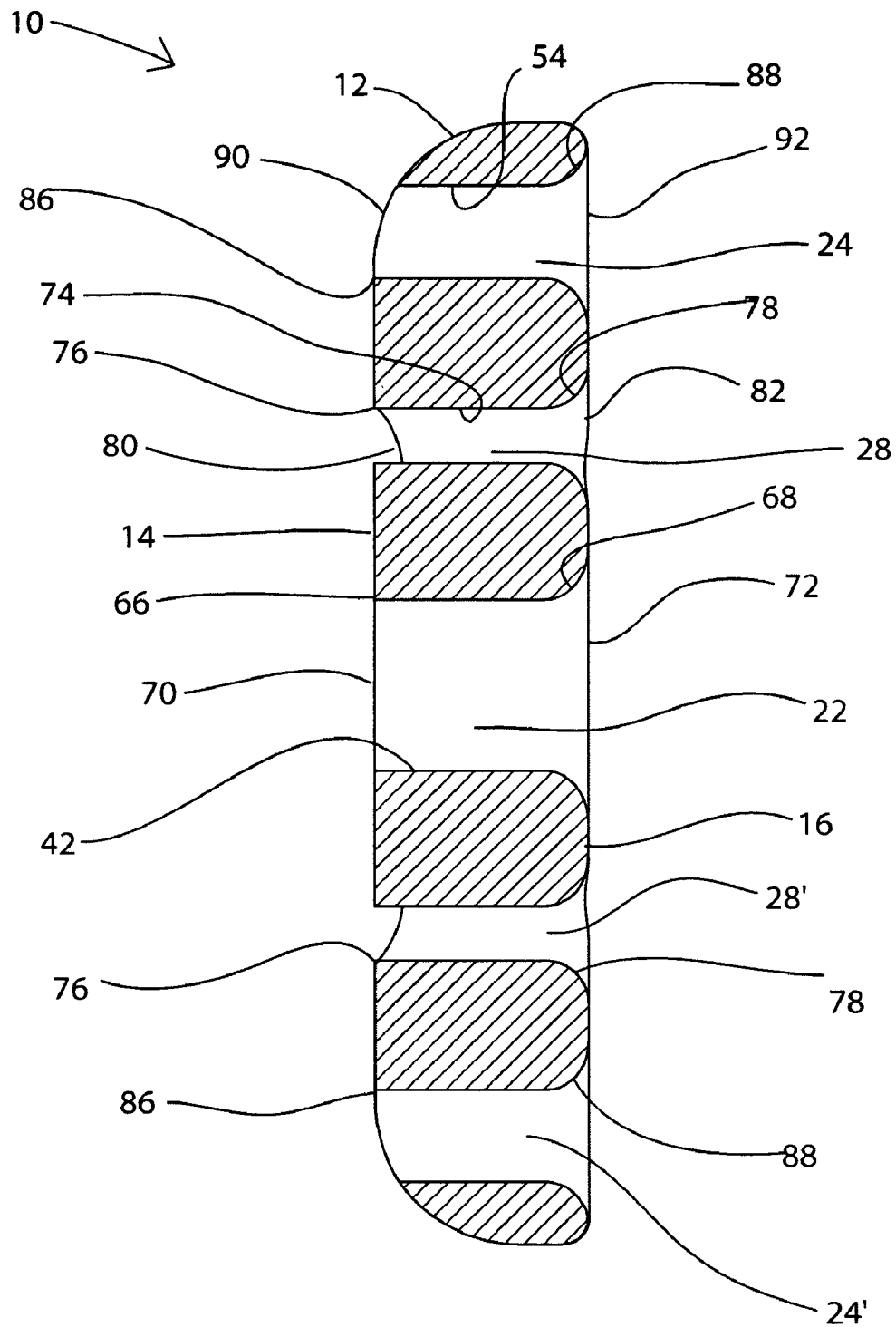
FIG. 3 is an elevated cross sectional side view of the line lock shown in FIG. 1.

Depicted in FIG. 3, interior surface 42 of primary passageway 22 extends to a top outside corner 66 and an opposing bottom outside corner 68. Top outside corner 66 bounds a top primary opening 70 while bottom outside corner 66 bounds a bottom primary opening 72. Similarly, first working passageway 28 has an interior surface 74 that extends to a top outside corner 76 and an opposing bottom outside corner 78. Top outside corner 76 bounds a top working opening 80 while bottom outside corner 76 bounds a bottom working opening 82. Likewise, interior surface 54 of first secondary passageway 24 extends to a top outside corner 86 and an opposing bottom outside corner 88. Top outside corner 86 bounds a top secondary opening 90 while bottom outside corner 86 bounds a bottom secondary opening 92.

For reasons as will be discussed below in greater detail, each of top outside corners 66, 76, and 86 has a radius of curvature that is smaller than the radius of curvature of the corresponding bottom outside corners 68, 78, 88. By way of example and not by limitation, in one embodiment top outside corners 66, 76, and 86 each have a radius of curvature in a range between about 0 mm to about 1 mm with about 0 mm to about 0.5 mm being more common. In contrast, bottom outside corners 68, 78, and 88 each have a radius of curvature in a range between about 0.25 mm to about 2 mm with about 0.5 mm to about 1.5 mm being more common. Other dimensions can also be used, particularly outside of the surgical area. In yet other embodiments it is appreciated that the top outside corners and the bottom outside corners can have the same radius of curvature or that only one or more of the top outside corners may be smaller than one or more of the bottom outside corners. In still other embodiments, it is appreciated that only a portion of one or more of the top outside corners may be smaller than a portion of one or more of the bottom outside corners.

It is again noted that second secondary passageway 24' and second working passageway 28' having substantially the same configuration as first secondary passageway 24 and first working passageway 28, respectively. As such, the same discussion with regard to the outside corners are also applicable thereto. Likewise, like elements are identified by like reference characters.

Figure 4A:
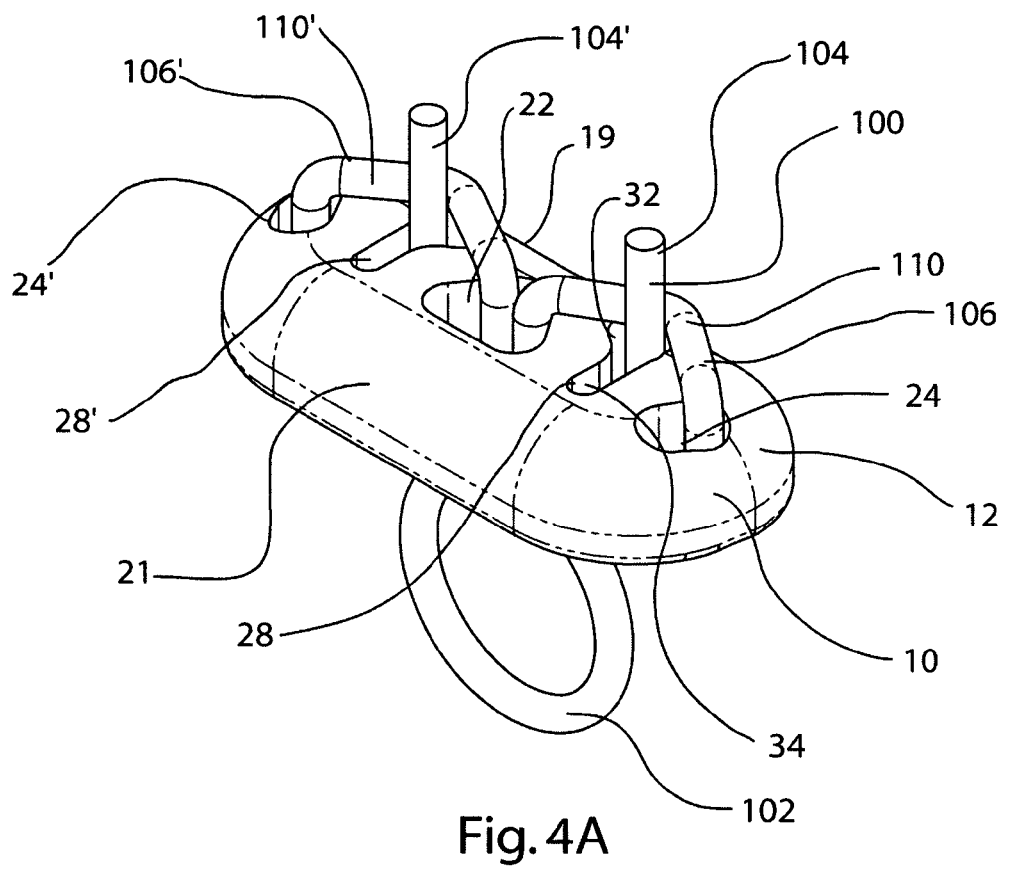
FIG. 4A is a perspective view of the line lock shown in FIG. 1 with a line routed therethrough in a slack unlocked position.

Depicted in FIG. 4A is a line 100 adjustably mounted on line lock 12. Line 100 comprises a standing portion 102 in the form of a loop which extends below primary passageway 22, a first working portion 104 which extends out of first working passageway 28, and a first locking portion 106 extending therebetween. It is appreciated that each of the sections 102, 104, and 106 of line 100 are relative to each other in that they change as line 100 is adjusted on line lock 10. Line 100 further includes a second working portion 104' which extends out of second working passageway 28' and a second locking portion 106' that extends between standing portion 102 and second working portion 104'.

First locking portion 106 extends up through primary passageway 22, down through first secondary passageway 24, and then up through first working passageway 28. The section of locking portion 106 extending between primary passageway 22 and first secondary passageway 24 is referred to as compression section 110. Line 100 passes up through first working passageway 28 so that first working portion 104 is disposed between compression section 110 and capture slot 34. Second locking portion 106' is similarly passed through passageways 22, 24', and 28'.

During use, standing portion 102 of line 100 is typically looped around, embedded within, or passed through tissue, or some other structure. To secure standing portion 102 to the structure, unwanted slack is removed from standing portion 102. This is accomplished by sliding line lock 10 over standing portion 102 and/or pulling on working portion 104 and/or 104' so that the unwanted slack is pulled through line lock 10. In either event, at least one of working portions 104 and 104' increases in length while standing portion 102 shortens.

In the configuration depicted in FIG. 4A, line 100 is passing through enlarged access regions 32 of working passageways 28 and 28'. In this position, relative locking portions 106 and 106' freely slide through corresponding passageways of line lock 10 as the unwanted slack from standing portion 102 is removed. A mild tension force is typically applied to working portions 104 and 104' as the unwanted slack is removed. The applied force pushes compression section 110 and 110' back toward first side 19 of body 12 and thus away from capture slots 34, 34'. In turn, the portion of line 100 passing through primary passageway 22 and secondary passageways 24 and 24' also naturally slides back within the passageways toward first side 19 of body 12. This movement of line 100 helps to decrease frictional resistance on line 100.

Figure 4B:
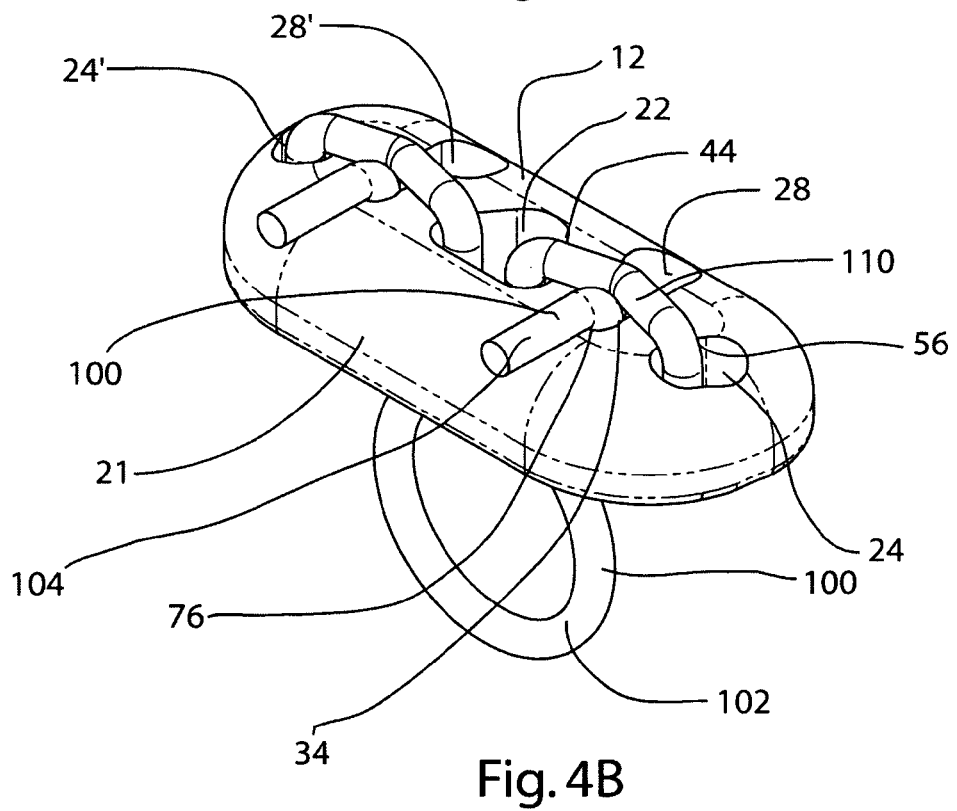
FIG. 4B is a perspective view of the line lock shown in FIG. 4A with the line in a tensioned locked position.

Once the slack is removed from standing portion 102, further force is applied to working portions 104, 104' and/or line lock 10 so as to tension locking portions 106, 106' on line lock 10. As depicted in FIG. 4B, as line 100 is tensioned, the diverging side face 44 of primary passageway 22 and side face 56 of first secondary passageway 24 cause the portions of line 100 passing therethrough, and thus compression portion 110 extending therebetween, to slide toward first side 21 of body 12.

Furthermore, as line 100 is tensioned, compression portions 110, 110' are shortened causing them to move into a more linear orientation. As a result of the above, tensioning of line 100 causes compression portions 110, 110' to force working portions 104, 104' toward corresponding capture slots 34, 34'. In turn, at least a portion of line 100 within working passageways 28 and 28' is forced into corresponding capture slots 34, 34' so that line 100 is secured therein by wedged frictional engagement. That is, line 100 is secured by compression within capture slots 34, 34' because line 100 has a diameter larger than the width of capture slots 34, 34'. Once line 100 is captured under compression in capture slots 34, 34', line 100 will remain captured even if there is a complete loss of tension in standing end 102. Thus, "locking" of line lock 10 to line 100 ensures that line lock 10 will not become separated from line 100, even under cyclic changes in line tension in standing end 102. Furthermore, line lock 10 is continuously adjustable in that further tension can be applied to standing portions 104 and/or 104' at any time to remove additional slack from standing portion 102 while retaining line 100 locked to line lock 10.

The passageways extending through line lock 10 are also configured such that as compression portions 110 and 110' force line 100 into capture slots 34 and 34', compression portions 110 and 110' also fold and/or bias working ends 104 and 104' over and/or against top outside corner 76 of capture slots 34 and 34'. In view of the relatively small radius of curvature of top outside corner 76, the engagement between the captured working ends 104 and 104' and top outside corner 76 creates a high degree of friction which forms a secondary locking mechanism between line 100 and line lock 10. As such, the engagement between capture working ends 104 and 104' and top outside corner 76 prevents backward movement of line lock 10 relative to line 100.

In the embodiment depicted in FIG. 4B, compression portion 110 is disposed above a portion of top outside corner 76 so as to directly bias working ends 104 against top outside corner 76. Compression portion 110 is also shown disposed directly above a portion of working end 104 that is biasing against top outside corner 76. In alternative embodiments, compression portion 110 when tensioned can extend between central passageway 22 and secondary passageways 24 without passing over working passageway 28. That is, compression portion 110 can pass at a location toward second side 21 of line lock 10 that is spaced apart from working passageway 28. In this embodiment, compression portion 110 still passes over working end 104, thereby remotely causing working end 104 to fold over and bias against top outside corner 76.

One of the unique features of the present embodiment is that as line lock 10 is advanced toward standing end 102 when standing end 102 is not under tension, i.e., when slack is being removed from standing end 102, working ends 104 and 104' tend to push away compression portions 110 and 110', as discussed above, thereby minimizing frictional engagement between working ends 104, 104', compression portions 110, 110' and line lock 10. As a result, line lock 10 can be easily advanced on line 100.

Furthermore, unlike some other continuously adjustable line locks known in the art that use a loop portion to draw in and wedge a portion of a line within a bore hole, compression portions 110 and 110' traverse a substantially straight path because they are constrained by secondary passageways 24 and 24' and primary passageway 22. This substantially straight path translates to a lower frictional resistance to sliding not possible with other adjustable line locks known in the art.

As previously discussed, line 100 is routed through passageways 22, 24, and 28 so as to pass over the outside corners of the passageways. When a tensioned section of line 100 passes around a first outside corner of line lock 10, friction produced between line 100 and the corresponding outside corner cause a decrease in tension on the portion of line 100 extending away from the outside corner on the side opposite the tensioned section. The friction produced at the outside corner must be overcome in order to cause line 100 to slide. Similarly, as the line passes around subsequent outside corners away from the tensioned section, each subsequent corner produces an incremental decrease in line tension and a corresponding incremental increase in friction that must be overcome to cause line 100 to slide. The loss in tension and increase in friction diminishes for each subsequent corner. Thus, the first corners are the most significant.

Figure 6:
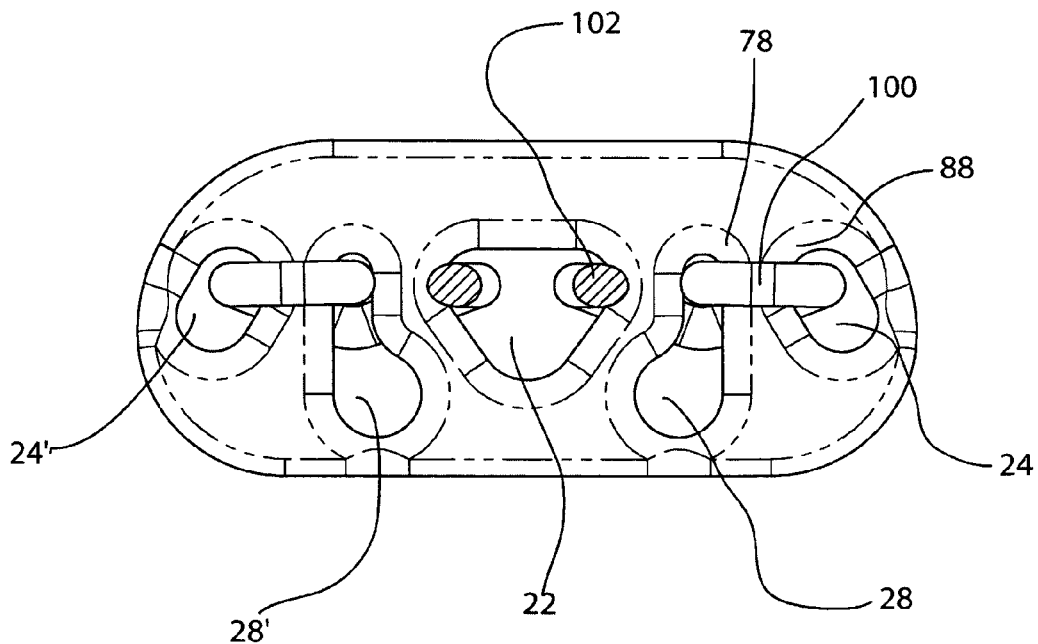
FIG. 6 is a bottom plan view of the line lock shown in FIG. 4B.

As depicted in FIG. 6, in view of the above discussion, when working end 104 is tensioned and standing end 102 is slack, line 100 extending from working end 104 toward line lock 10 first turns on bottom outside corner 78 of working passageway 28 and bottom outside corner 88 of secondary passageway 24. As a result of the fact that these are the closest outside corners to tensioned working end 104, outside corners 78 and 88 will produce the highest frictional resistance. Accordingly, to minimize the frictional resistance produced by outside corners 78 and 88 and thereby ease the sliding of line lock 10 toward standing end 102, outside corners 78 and 88 are generously rounded as previously discussed.

Figure 5:
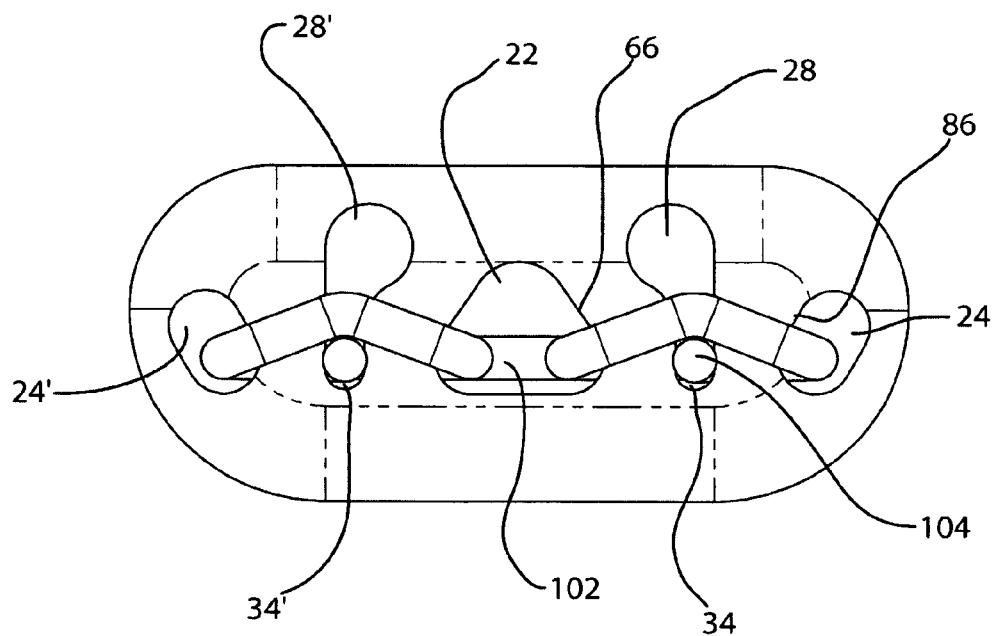
FIG. 5 is a top plan view of the line lock shown in FIG. 4B.

In contrast, as depicted in FIG. 5, when standing end 102 is tensioned and working end 104 is slack, line 100 extending from standing end 102 toward line lock 10 first turns on top outside corner 66 of primary passageway 22 and top outside corner 86 of secondary passageway 24. In view of the fact that these are the closest outside corners to tensioned standing end 102, outside corners 66 and 86 will produce the highest frictional resistance. Accordingly, to maximize the frictional resistance produced by outside corners 66 and 86 and thereby minimizing slipping of line 100 once tensioned, outside corners 66 and 86 are formed relative sharp as previously discussed. More specifically, top outside corners 66 and 86 have a smaller radius of curvature than bottom outside corners 78 and 88. It is noted that not all of each outside corner that bounds a corresponding opening has to have the same radius of curvature. For example, the portion of each outside corner that directly engages line 100 can have a radius of curvature that is different from the remainder of the corresponding outside corner.

Figure 7:
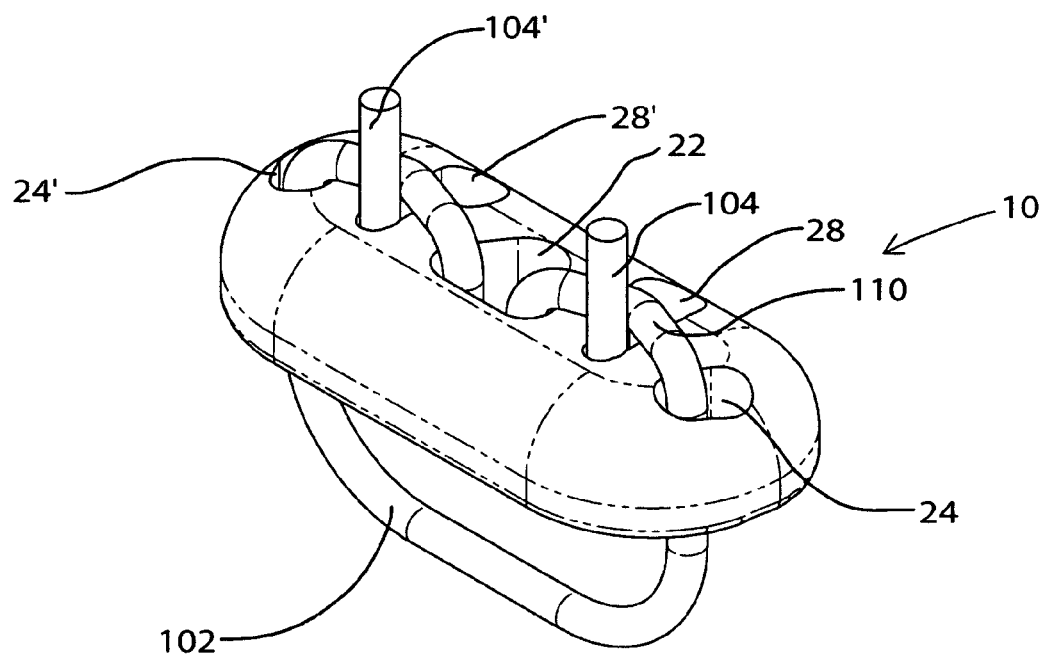
FIG. 7 is a perspective view of the line lock shown in FIG. 4A with the line routed in a different path.

Depicted in FIG. 7, line lock 10 is shown having an alternative routing of line 100. To achieve this routing, working ends 104 and 104' are passed up through secondary passageways 24 and 24', respectively, down through primary passageway 22, and then back up through working passageways 28 and 28', respectively. Again compression portions 110 and 110' are formed that selectively force working ends 104 and 104' toward capture slots 34 as discussed above. In yet another alternative, it is appreciated that one end of line 100 can be routed as shown in FIG. 4A while the opposing end of line 100 is routed as shown in FIG. 7.

Figure 8:
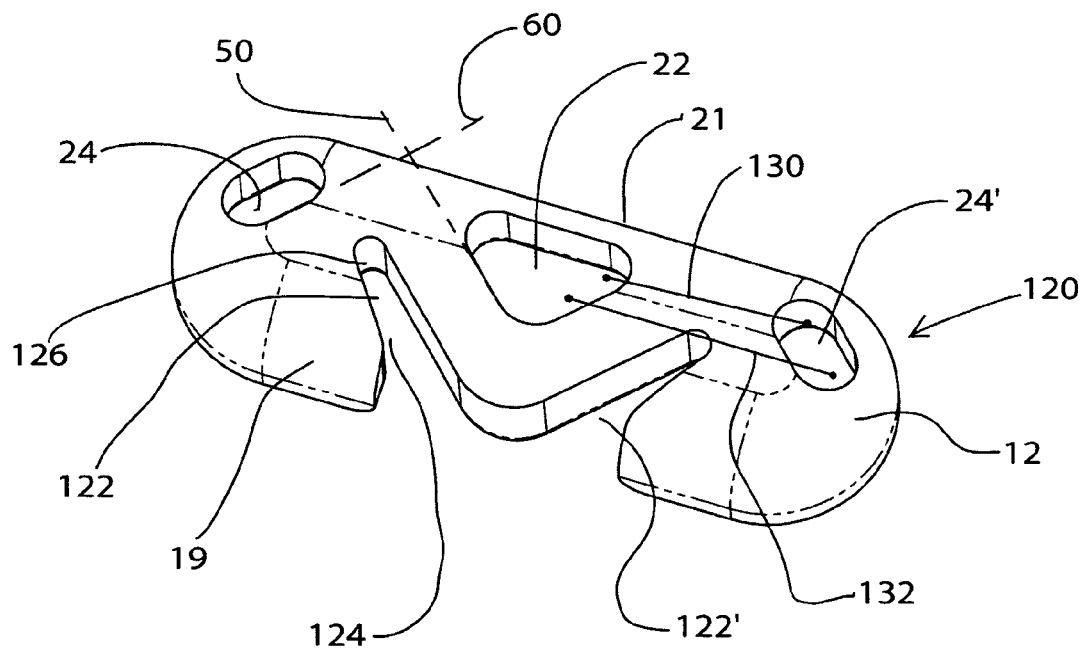
FIG. 8 is a perspective view of an alternative embodiment of the line lock shown in FIG. 1 with open working passageways.

Depicted in FIG. 8 is an alternative embodiment of a line lock 120. It is noted that all common elements of alternative embodiments of line locks disclosed herein are identified by like reference characters. Line lock 120 comprises body 12 having primary passageway 22 and secondary passageways 24 and 24' extending therethrough as discussed above with regard to FIG. 1. In contrast to the circumferentially closed working passageways 28, 28', however, line lock 120 comprises working passageways 122 and 122' that are circumferentially open. That is, each working passageway 122 and 122' comprises an elongated tapered slot having a first end 124 and an opposing second end 126. First end 124 is open along first side 19 of body 12 to facilitate convenient loading of line 100 therein. First end 124 also typically has a width greater than the diameter of line 100. Second end 126 extends to a location between primary passageway 22 and a corresponding one of secondary passageway 24, 24'.

In this embodiment it is noted that the passageways are positioned such that a geometric line segment 130 can be extended between primary passageway 22 and secondary passageway 24' such that line segment 130 does not intersect with working passageway 122'. However, a geometric line segment 132 can also be extended between primary passageway 22 and secondary passageway 24' such that line segment 132 intersects with working passageway 122'. Second end 126 of each working passageway 122, 122' typically has a width substantially equal to or smaller than the diameter of line 100.

Figure 9:
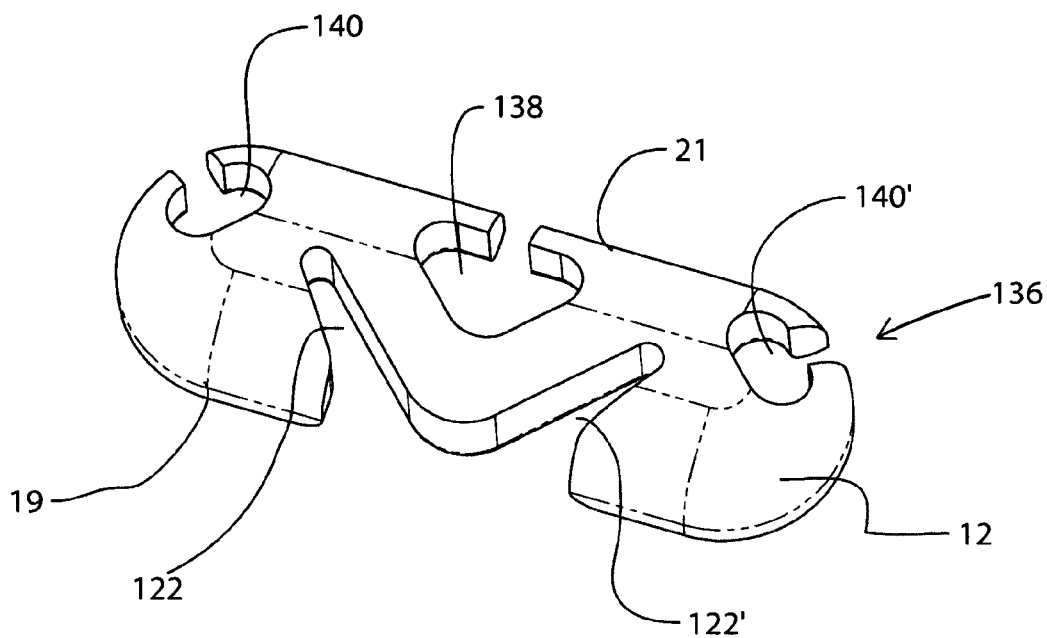
FIG. 9 is a perspective view of another alternative embodiment of the line lock shown in FIG. 1 with open passageways.

Depicted in FIG. 9 is another alternative embodiment of a line lock 136 having substantially the same configuration as line lock 120. In contrast to the circumferentially bounded primary passageway 22 and secondary passageways 24 and 24' of line lock 120 in FIG. 8, however, line lock 136 comprises a partially bounded primary passageway 138 which is open at second side 21 of body 12 and partially bounded secondary passageways 140 and 140' that are also each open at or adjacent to second side 21 of body 12.

Figure 10:
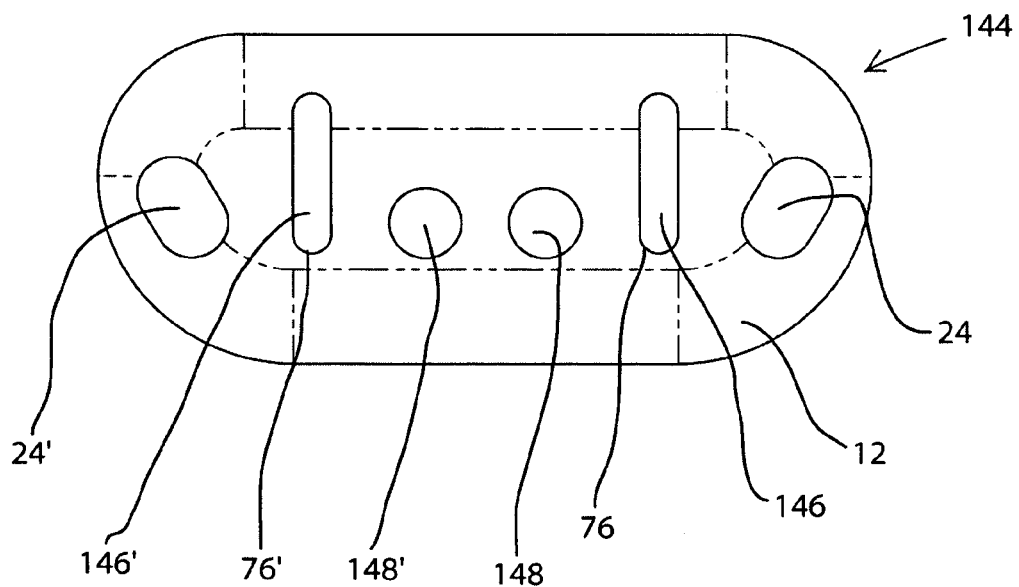
FIG. 10 is a perspective view of another alternative embodiment of the line lock shown in FIG. 1 with dual primary passageways and uniform working passageways.

Two separate locking features were previously discussed with regard to securing line 100 to line lock 10. Specifically, line 100 is secured by being wedged into capture slots 34 and 34' and by biasing working portions 104 and 104' against the top outside corner 76 of each working passageway 28, 28'. In alternative embodiments, it is appreciated that the locking features can be used independently. For example, depicted in FIG. 10 is a line lock 144 having body 12 with secondary passageways 24 and 24'. In contrast to line lock 10, however, line lock 144 comprises working passageways 146 and 146' wherein capture slots 34 have been eliminated. Working passageways 146 and 146' merely comprise elongated channels having a width substantially the same size or larger than the diameter of the line 100 to be passed therethrough. Line 100 is thus primarily secured to line lock 144 as a result of compression portions 110, 110' biasing line 100 against top outside corner 76 of each working passageways 146 and 146' as previously discussed.

Line lock 144 is also distinguished over line lock 10 in that primary passageway 22 has been replaced with a first primary passageway 148 and a spaced apart second primary passageway 148'. Primary passageways 148 and 148' operate with opposing ends of line 100. It is also noted that in alternative embodiments primary passageway(s) and/or the secondary passageways need not be elongated to allow the line passing therethrough to slide toward opposing sides 19 and 21 of body 12 as previously discussed with regard to line lock 10.

Figure 11:
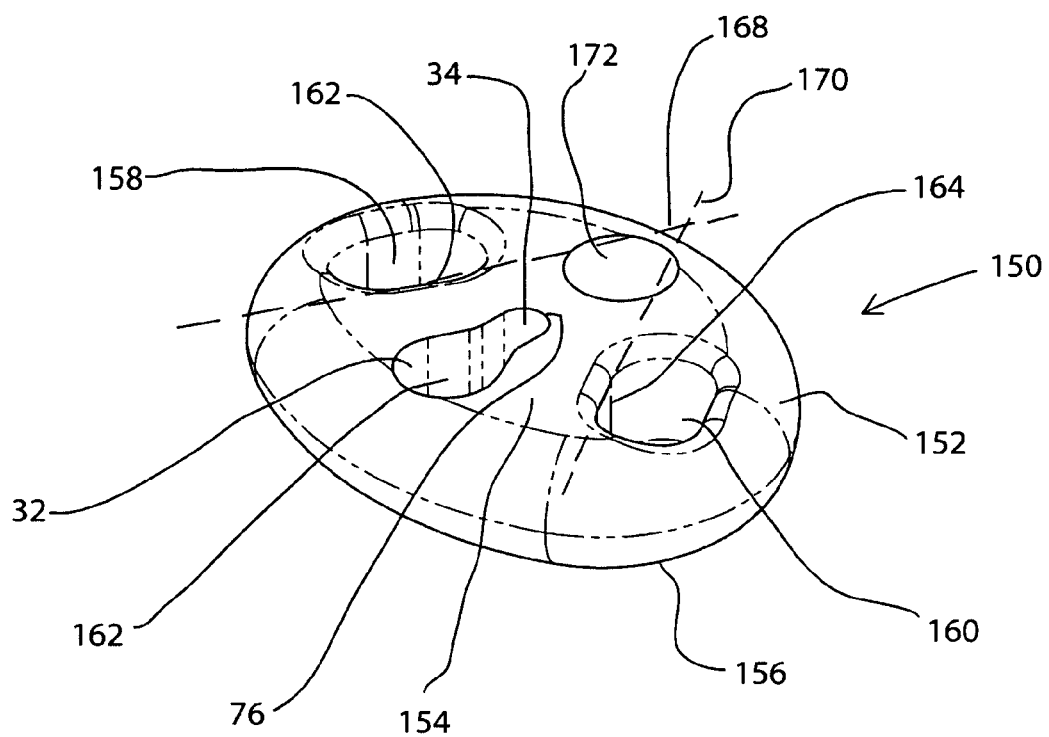
FIG. 11 is a perspective view of a line lock for use with a single strand of line.

Depicted in FIG. 11 is an alternative embodiment of a line lock 150 that is designed to slide along a single strand of line 100. Line lock 150 comprises a substantially disk shaped body 152 having a top surface 154 and an opposing bottom surface 156. Extending through body 152 between surfaces 154 and 156 is a primary passageway 158 and a spaced apart secondary passageway 160. Disposed between passageways 158 and 160 is a working passageway 162. Similar to line lock 10, working passageway 162 of line lock 150 has a first end with enlarged access region 32 and an opposing second end with constricted capture slot 34 thereat.

Primary passageway 158 and secondary passageway 160 have substantially the same elongated circular configuration which is similar to previously discussed secondary passageway 24. Each of passageways 158 and 160 has an inside face 162 and 164, respectively, that is disposed toward working passageway 162. Each inside face 162 and 164 is substantially disposed in or is tangent to a corresponding plane 168 and 170, respectively. Planes 168 and 170 converge toward capture slot 34 of working passageway 162 and diverge away from access region 32.

Also extending through body 152 between top surface 154 and bottom surface 156 is an end passageway 172. Although end passageway 172 can be positioned at a variety of different locations, end passageway 172 is shown aligned with working passageway 162 such that a plane extending between working passageway 162 and end passageway 172 separates primary passageway 158 from secondary passageway 160.

Figure 12A:
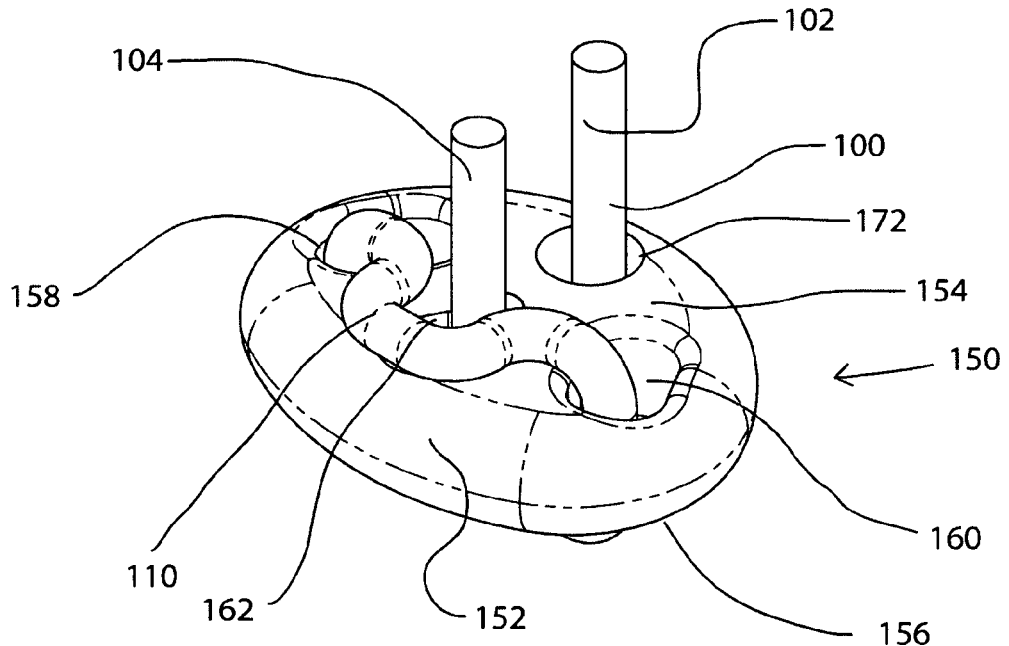
FIG. 12A is a perspective view of the line lock shown in FIG. 11 with a line routed therethrough.
Figure 12B:
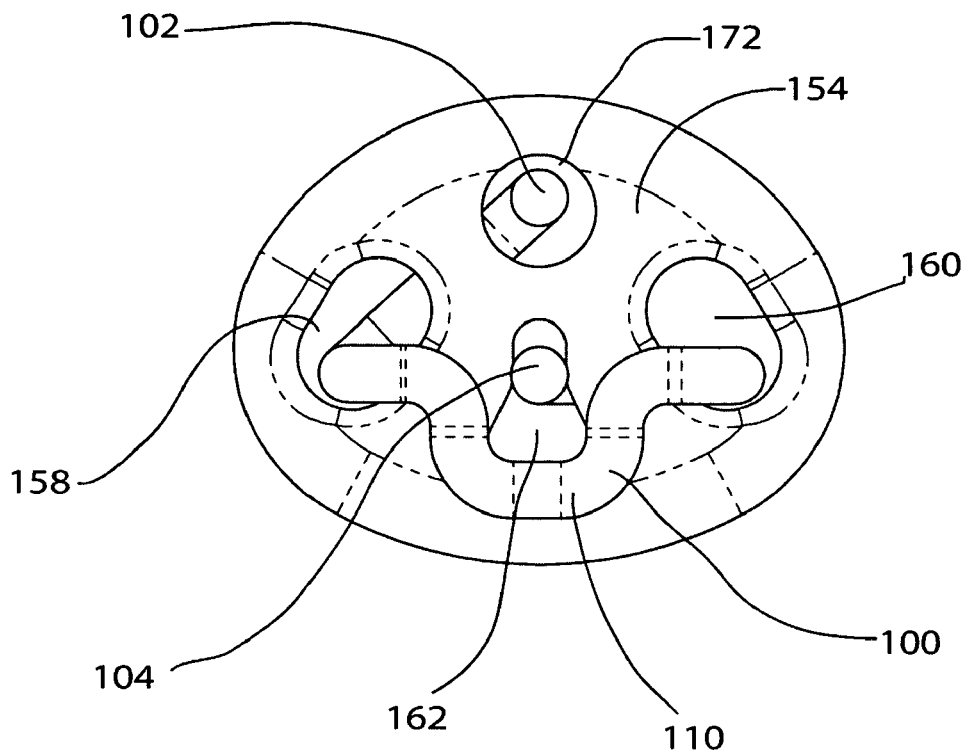
FIG. 12B is a top plan view of the line lock shown in FIG. 12A.
Figure 12C:
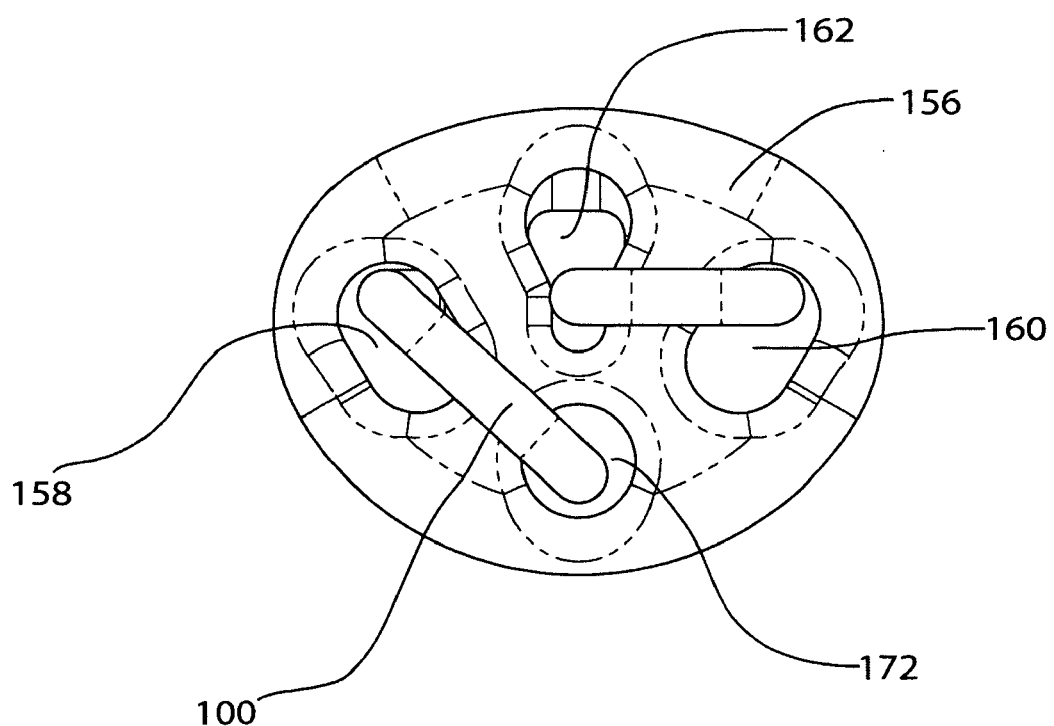
FIG. 12C is a bottom plan view of the line lock shown in FIG. 12A.

During use, as depicted in FIGS. 12A-12C, line 100 is routed through line lock 150 by passing working portion 104 from top surface 154 to bottom surface 156 through end passageway 172, up through primary passageway 158, down through secondary passageway 160, and finally up through working passageway 162. Compression portion 110 of line 100 extends between primary passageway 158 and secondary passageway 160 and is positioned to act upon working portion 104. Line lock 150 can be selectively advanced by pulling working portion 104 away from top surface 154 so that line 100 travels through line lock 150. Alternatively, line lock 150 can be manually slid toward standing portion 102. In either event, the length of standing portion 102 is decreased.

As line 100 is tensioned on line lock 150, line 100 locks on line lock 150 in substantially the same manner that line 100 locks with working passageway 28 as previously discussed with regard to line lock 10. That is, compression portion 110 forces working end 104 toward capture slot 34 so that the portion of line 100 within working passageway 162 is captured by wedged frictional engagement within capture slot 34. Furthermore, compression portion 110 either directly or indirectly biases working portion 104 against the top outside corner 76 of working passageway 162 at the second end thereof so as to increase the frictional engagement between line 100 and line lock 150. Line lock 150 thus provides a continuously adjustable line lock or a one way sliding stop. In alternative embodiments, it is appreciated that line lock 150 can be modified in at least the same ways as discussed with the other line locks disclosed herein.

The embodiment shown in FIGS. 12A-12C is advantageous in certain applications where line lock 150 is positioned behind a first object and working portion 104 and standing portion 102 pass through the first object. In this situation, standing portion 102 is fixed to a second object. By pulling on working portion 104, the first object is drawn irreversibly toward the second object. This is an advantage with surgical sutures where standing end 102 of a suture is attached to normal tissues and line lock 150 is placed behind tissue that has torn away. Standing portion 102 and working portion 104 pass through the torn tissue toward the normal tissue. By pulling on working portion 104 of suture, the torn tissue is pulled into apposition with the normal tissues and line lock 150 maintains the torn tissue adjacent to the normal tissue to facilitate healing of the tissue.

Figure 13A:
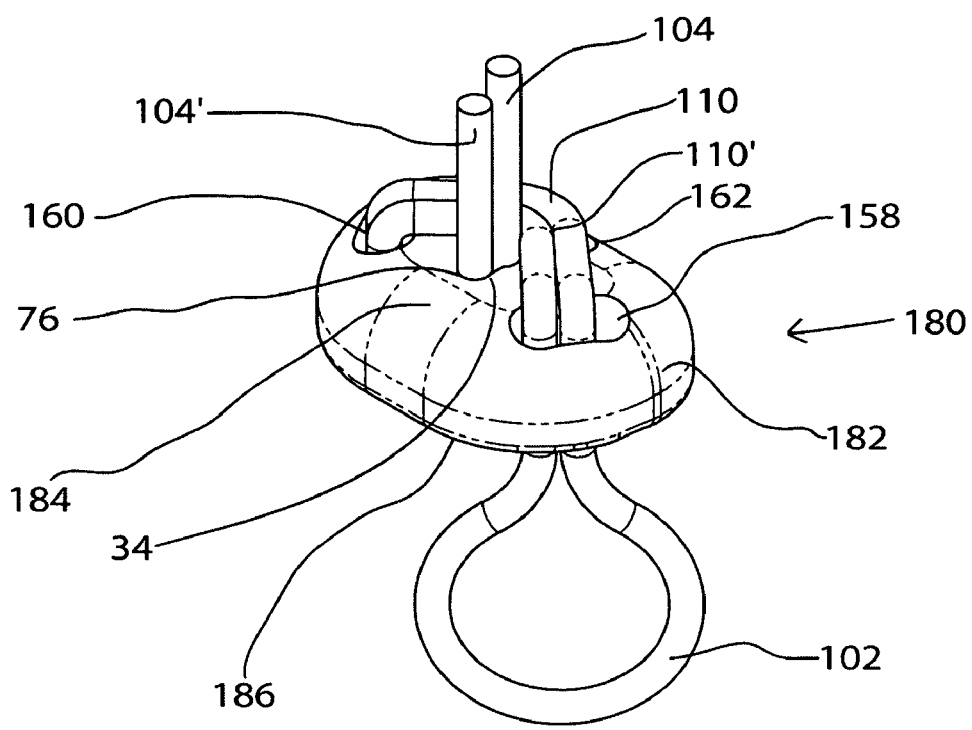
FIG. 13A is a top perspective view of a line lock having dual strands of line routed therethrough.
Figure 13B:
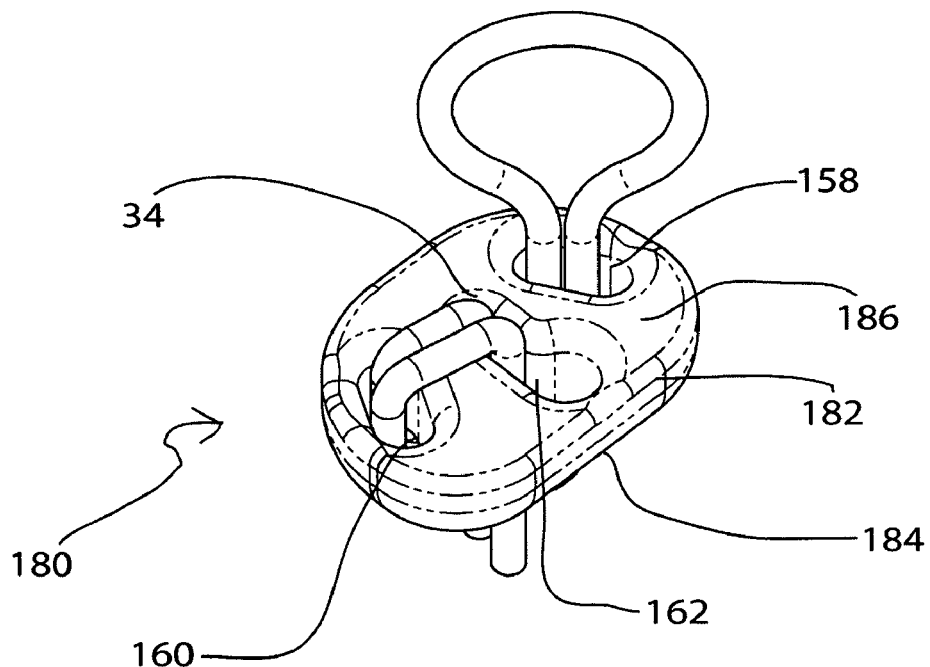
FIG. 13B is a bottom perspective view of the line lock shown in FIG. 13A.

Depicted in FIGS. 13A and 13B is another embodiment of a line lock 180 incorporating features of the present invention. Line lock 180 also comprises a substantially disk shaped body 182 having a top surface 184 and an opposing bottom surface 186. As with line lock 150, line lock 180 includes primary passageway 158, secondary passageway 160, and working passageway 162. Again, although not required, working passageway 162 is disposed such that a geometric line segment can be extended between primary passageway 158 and secondary passageway 160 so that the line segment intersects with working passageway 162. In contrast to line lock 150, line lock 180 does not include end passageway 172.

Each of passageways 158, 160, and 162 is configured to receive a double strand of line 100. Specifically, during use both working end 104 and 104' are passed up through primary passageway 158, down through secondary passageway 160 and then back up through working passageway 162. As a result, standing portion 102 is again formed in a loop that can be looped around, passed through, or otherwise secured to tissue or other structure. Unwanted slack is removed from standing portion 102 by again sliding line lock 180 on line 100 toward standing portion 102 and/or by pulling on one or both of working portions 104 and 104' so that line 100 passes through line lock 180.

When line 100 is tensioned on line lock 180, compression portions 110 and 110' force working portions 104, 104' toward capture slot 34 so that a portion of each line section passing through working passageway 162 is captured by wedged frictional engagement within capture slot 34. Compression portions 110 and 110' also bias working portions 104 and 104' toward and/or against top outsider corner 76 of working passageway 162 so as to increase the frictional engagement between line 100 and line lock 180. As previously discussed with passageways 22, 24, and 28 of line lock 10 in FIGS. 1-6, the radius of curvature of the top outside corner and bottom outside corner of each passageway 158, 160, and 162 can be set so as to further control the ability of line 100 to slide or not slide through the passageway. Other alternatives as discussed with the line locks herein are also applicable to line lock 180. In particular each of the passageways 158, 160, and 162 can also be configured to receive a single strand of line 100. In this configuration the single strand of line 100 is routed in a manner as described above for the double strand of line 100. Instead of the standing portion 102 forming a loop when a double strand of line 100 is used, in this case the standing portion 102 consists of a free end which can be attached to tissue or other structures.

Figure 14A:
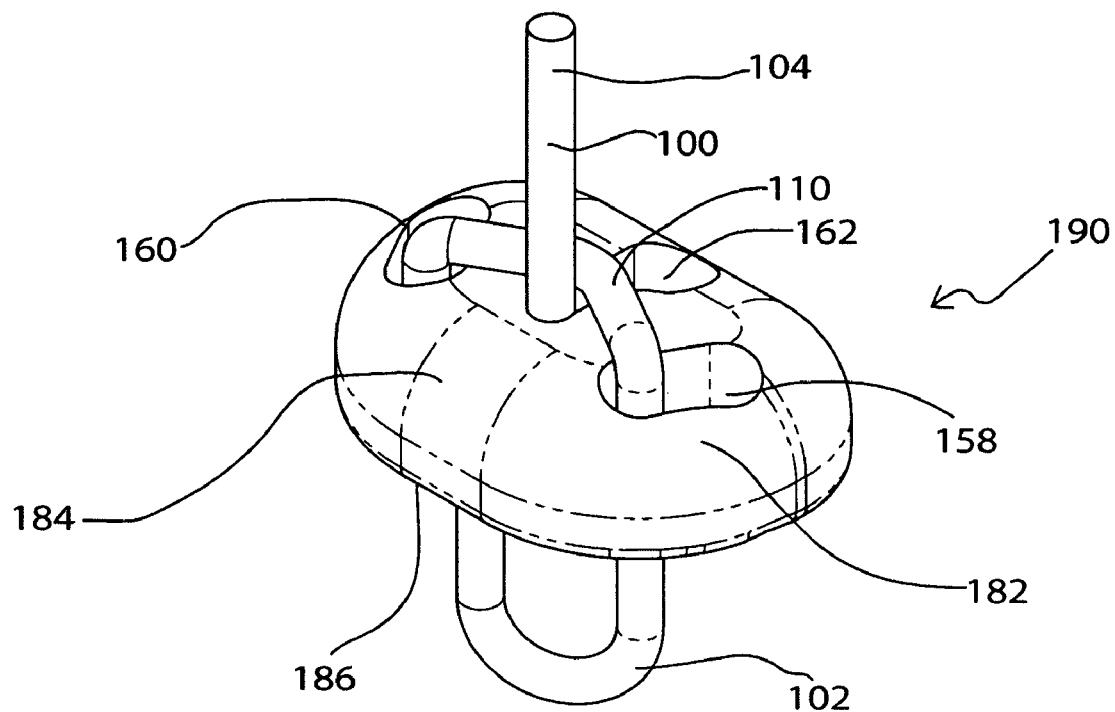
FIG. 14A is a top perspective view of a line lock having a line secured thereto.
Figure 14B:
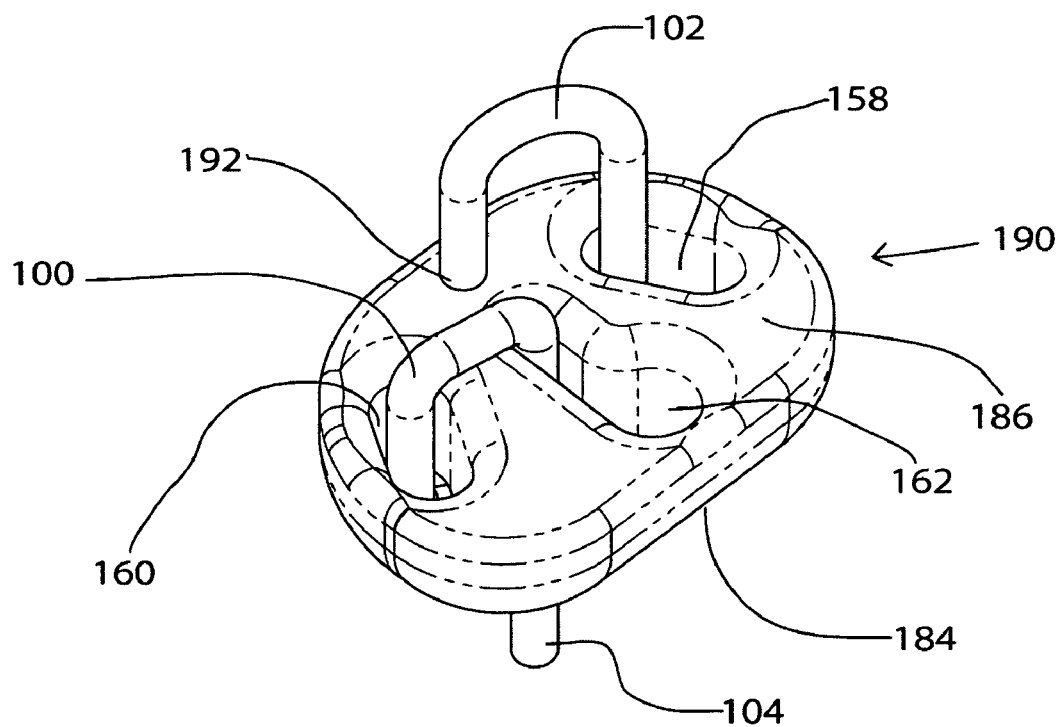
FIG. 14B is a bottom perspective view of the line lock shown in FIG. 14A.

Depicted in FIGS. 14A and 14B is still another embodiment of a line lock 190 incorporating features of the present invention. Line lock 190 has substantially the same configuration as line lock 180 with like elements being referenced with like reference characters. The primary distinction between line locks 180 and 190 is that in line lock 190, an end 192 of line 100 adjacent to standing portion 102 is secured to bottom surface 186 of body 182. End 192 can be secured to body 182 by being integrally molded into body 182 or can be otherwise secured such as by welding or mechanical attachment.

Line lock 190 is also distinguished from line lock 180 in that passageways 158, 160, and 162 need only be configured to receive a single strand of line 100. That is, working end 104 passes up through primary passageway 158, down through secondary passageway 160, and then back up through working passageway 162. Standing portion 102 is again substantially formed into a loop extending from end 192 of line 100 to primary passageway 158. Because end 192 of line 100 is secured to body 182, unwanted slack can be removed from standing portion 102 by pulling line 100 through line lock 190 and/or sliding line lock 190 down line 100. Line 100 is locked to line lock 190 in substantially the same manner as discussed above with regard to the other line locks when line 100 is tensioned on line lock 190.

Figure 15:
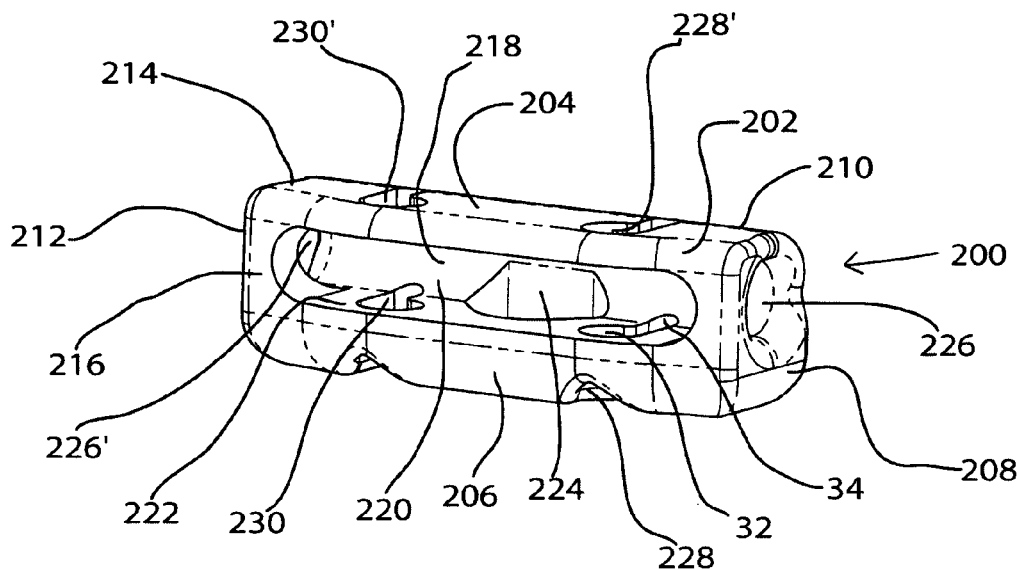
FIG. 15 is a perspective view of an alternative embodiment of a line lock.

Depicted in FIG. 15 is still another embodiment of a line lock 200 incorporating features of the present invention. Line lock 200 comprises an elongated substantially box shaped body 202 comprising a top wall 204 and an opposing bottom wall 206 each extending between a first side wall 208 and a first end 210 and an opposing second side wall 212 and an opposing second end 214. Also extending between top wall 204 and bottom wall 206 is a front wall 216 and an opposing back wall 218.

Partially bounded within body 202 is a hollow chamber 220. An access channel 222 is formed on front wall 216 so as to communicate with chamber 220. Also communicating with chamber 220 is a primary passageway 224. Primary passageway centrally extends through bottom wall 206 to chamber 220. A first secondary passageway 226 extends through first side wall 208 so as to communicate with chamber 220 while a second secondary passageway 226' extends through second side wall 212 so as to communicate with chamber 220. A pair of first working passageways 228 and 228' extend through bottom wall 206 and top wall 204, respectively, in vertical alignment between primary passageway 224 and first secondary passageway 226.

Similarly, a pair of second working passageways 230 and 230' extend through bottom wall 206 and top wall 204 in vertical alignment between primary passageway 224 and second secondary passageway 226'. As with the prior working passageways, each of working passageways 228, 228' and 230, 230' has a first end towards front wall 226 with an enlarged axis region 32 and an opposing second end toward back wall 218 with a capture slot 34 formed thereat.

Figure 16A:
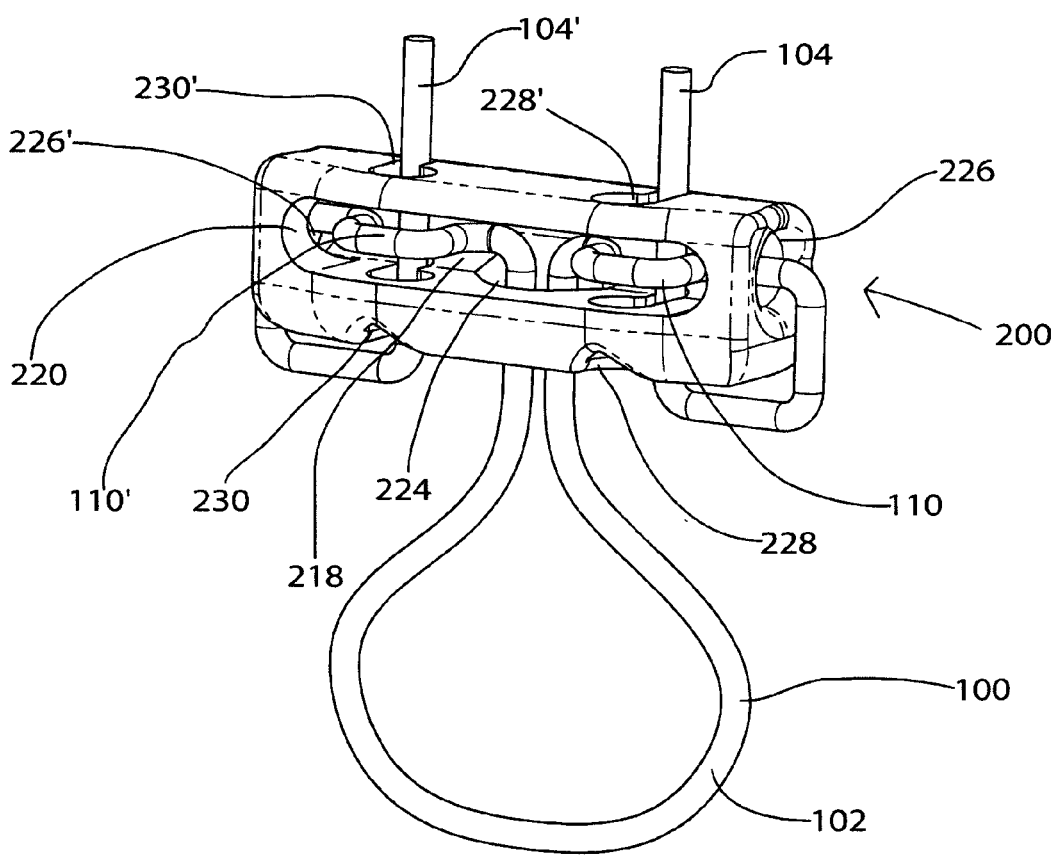
FIG. 16A is a perspective view of the line lock shown in FIG. 15 with a line routed therethrough.
Figure 16B:
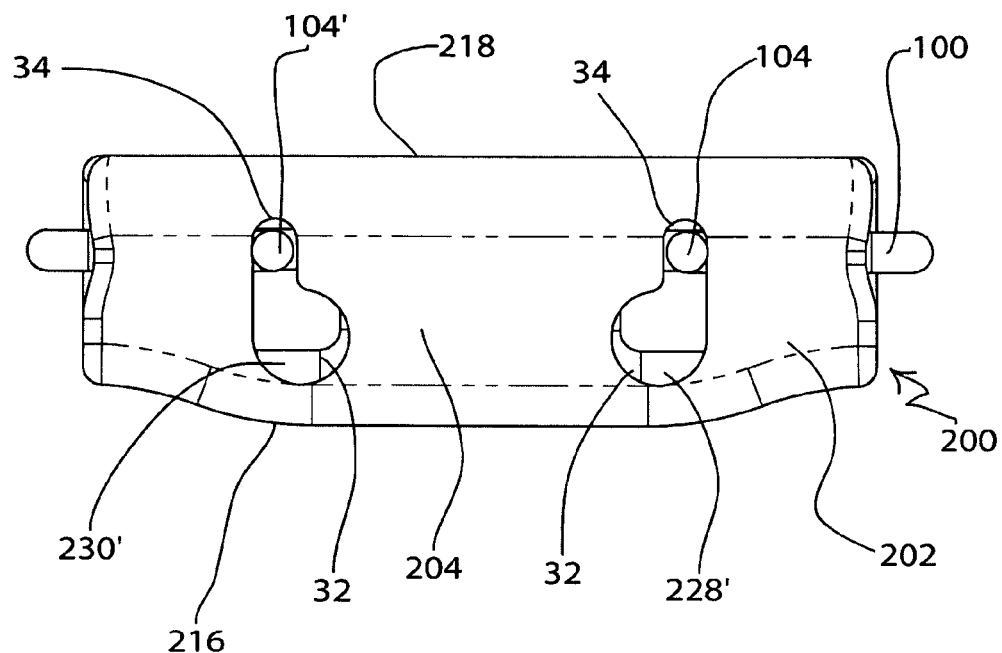
FIG. 16B is a top plan view of the line lock shown in FIG. 16A.
Figure 16C:
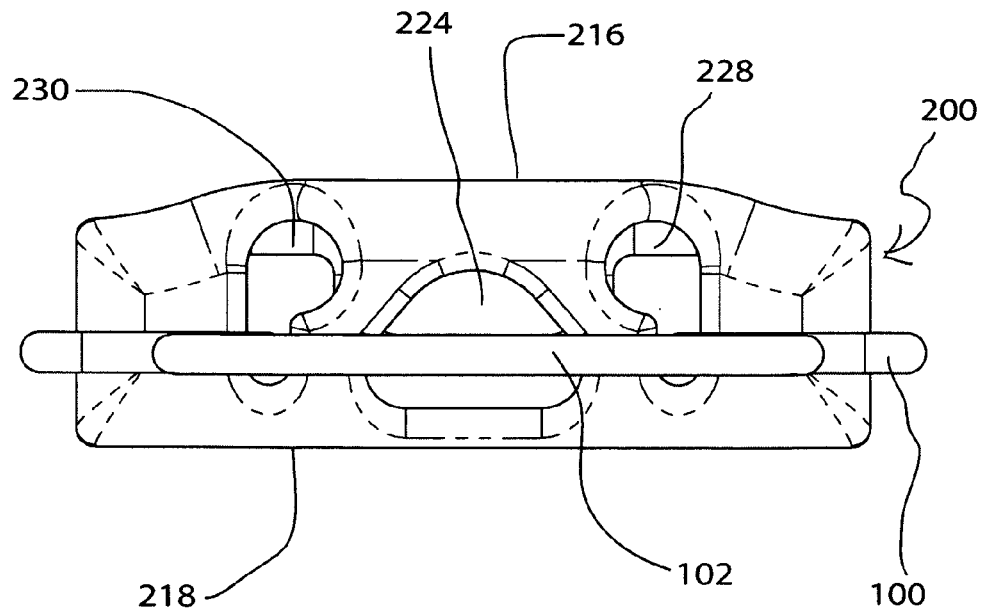
FIG. 16C is a bottom plan view of the line lock shown in FIG. 16A.

During use, as depicted in FIGS. 16A-16C, working portions 104 of line 100 are passed up through primary passageway 224 into chamber 220. Working portion 104 then passes out of chamber 220 through first secondary passageway 226. Finally, working portion 104 passes up through first working passageway 228, through chamber 220, and then out through first working passageway 228'. Compression portion 110 of line 100 extends from primary passageway 224 to first secondary passageway 226. Working portion 104 is routed such that line 100 passes between compression portion 110 and back wall 218.

In like manner, working portion 104' extends from chamber 220 out through second secondary passageway 226'. Working portion 104' then extends up through second working passageway 230, through chamber 220, and then out through second working passageway 230'. Again, line 100 extends between compression portion 110' and back wall 218.

As with the other embodiments, line lock 200 can be slid along line 100 and/or line 100 can be pulled therethrough so as to remove all unwanted slack from standing portion 102. As line 100 is tension on line lock 200, compression portions 110 and 110' force the portion of line 100 extending between first working passageways 228 and 228' and between second working passageways 230 and 230', respectively, toward corresponding capture slots 34. As a result, at least a portion of line 100 extending through each of the working passageways is captured by frictional wedge engagement within each of the corresponding capture slots 34. Line 100 is thus locked with line lock 200.

Line lock 200 offers several advantages. When standing end 102 is slack and working ends 104 and 104' are tensioned, the sections of line 100 extending between working passageways 228 and 228' and between working passageways 230 and 230' force compression portions 110 and 110', respectively, back toward front wall 216 so as to allow the free travel of line 100 through line lock 200. In contrast, as discussed above, when tension is created in standing end 102 and slack is created in working ends 104 and 104', compression portions 110 and 110' force the sections of line 100 extending between working passageways 228 and 228' and between working passageways 230 and 230' toward back wall 218 so as to secure line 100 within the capture slots 34. This back and forth movement of compression portions 110 and 110' creates "backlash," or a finite distance that line lock 200 can move away from standing end 102 until locking of line 100 is achieved.

Top wall 204 of line lock 200 provides a physical constraint to the amount of movement seen in compression portions 110 and 110', thereby minimizing the amount of backlash. Furthermore, top wall 204 provides an additional friction point when compression portions 110 and 110' compress against line 100, thereby increasing the strength of the locking of line 100. That is, one friction point is located at working passageways 228 and 230 on bottom wall 206 and the second friction point is located at working passageways 228' and 230' on top wall 204.

It is again appreciated that the alternatives as discussed with the other embodiments are also applicable to line lock 200. By way of example and not by limitation, line 100 can be routed through line lock 200 in a manner analogous to the routing in FIG. 7. The various passageways can be open or closed as depicted in FIGS. 8 and 9. Similarly, line lock 200 can be divided in half and modified to function similar to the line locks shown in FIGS. 11-14.

Figure 17:
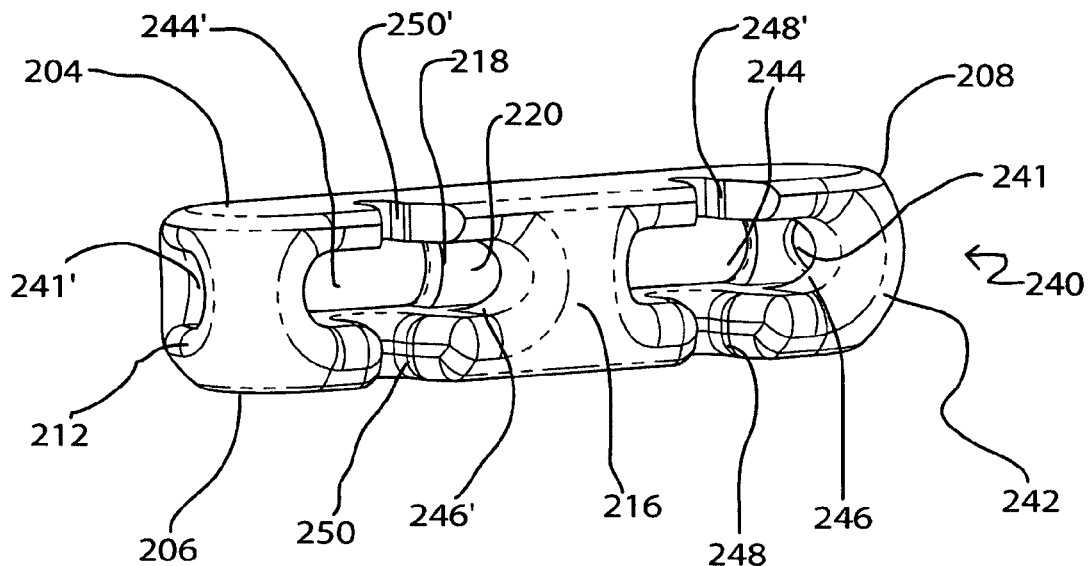
FIG. 17 is a perspective view of another alternative embodiment of a line lock.

Depicted in FIG. 17 is a final alternative embodiment of a line lock 240 incorporating features of the present invention. Line lock 240 has a configuration similar to line lock 200 and thus like elements are identified by like reference characters. Line lock 240 comprises an elongated substantially box shaped body 242. Similar to line lock 200, body 242 comprises top wall 204 and bottom wall 206 extending between side wall 208 and side wall 212. Body 242 also includes front wall 216 and back wall 218 which partially bound chamber 220.

In contrast to line lock 200, a first primary passageway 241 extends through first side wall 208 while second primary passageway 241' extends through second side wall 212. Primary passageways 241 and 241' each communicate with chamber 220. Body 242 of line lock 240 further comprises a first secondary passageway 244 extending through back wall 218 in communication with chamber 220 and a spaced apart second secondary passageway 244' in communication with chamber 220. A first access port 246 extends through front wall 216 in alignment with first secondary passageway 244' so as to communicate with chamber 220. Similarly, a second access port 246' extends through front wall 216 in alignment with second secondary passageway 244 so as to also communicate with chamber 220.

Furthermore, in contrast to the bounded working passageways of line lock 200, line lock 240 comprises a pair of first working passageways 248 and 248'. Working passageway 248 comprises a constricting slot that is formed on bottom wall 206 and is open along intersecting front wall 216. First working passageway 248' is aligned with first working passageway 248 and is formed on top wall 204 so as to also be open along intersecting front wall 216. A pair of second working passageways 250 and 250' are similarly formed on bottom wall 206 and top wall 204 so as to be aligned with second secondary passageway 244'. Each of the working passageways terminates at capture slot having a width substantially equal to or smaller than the diameter of line 100.

Figure 18A:
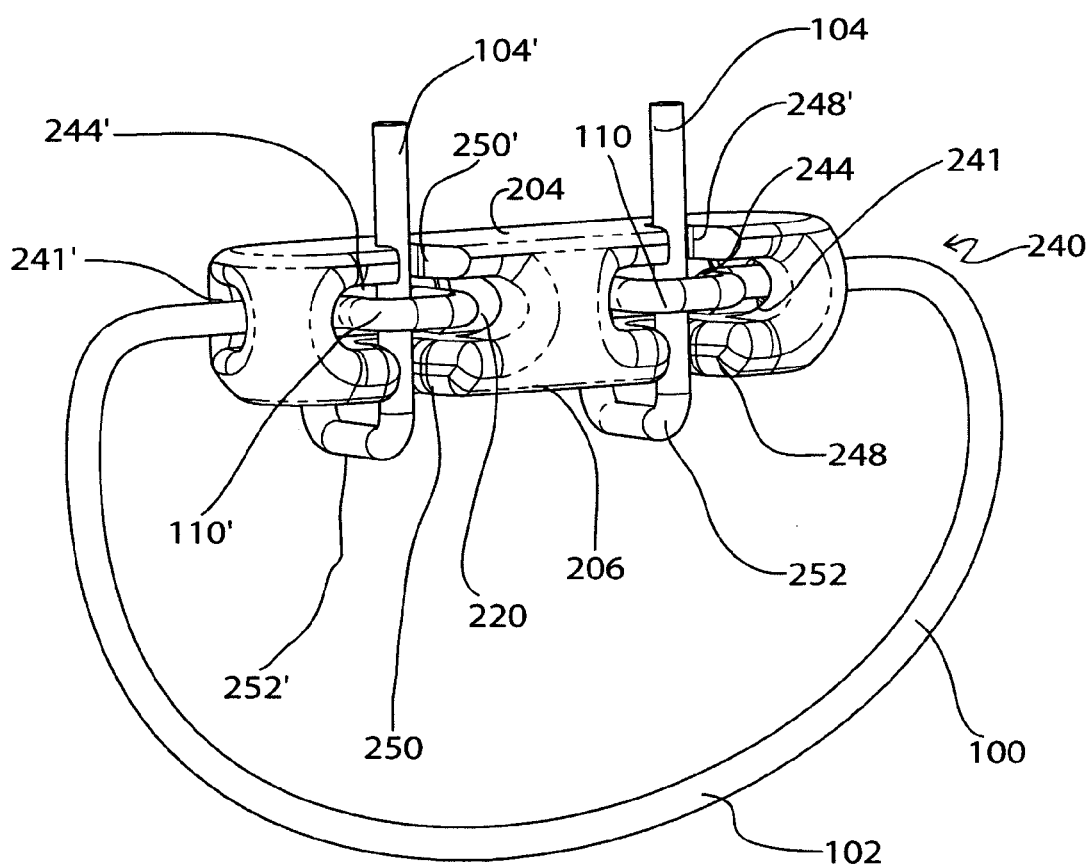
FIG. 18A is a perspective view of the line lock shown in FIG. 17 with a line routed therethrough.
Figure 18B:
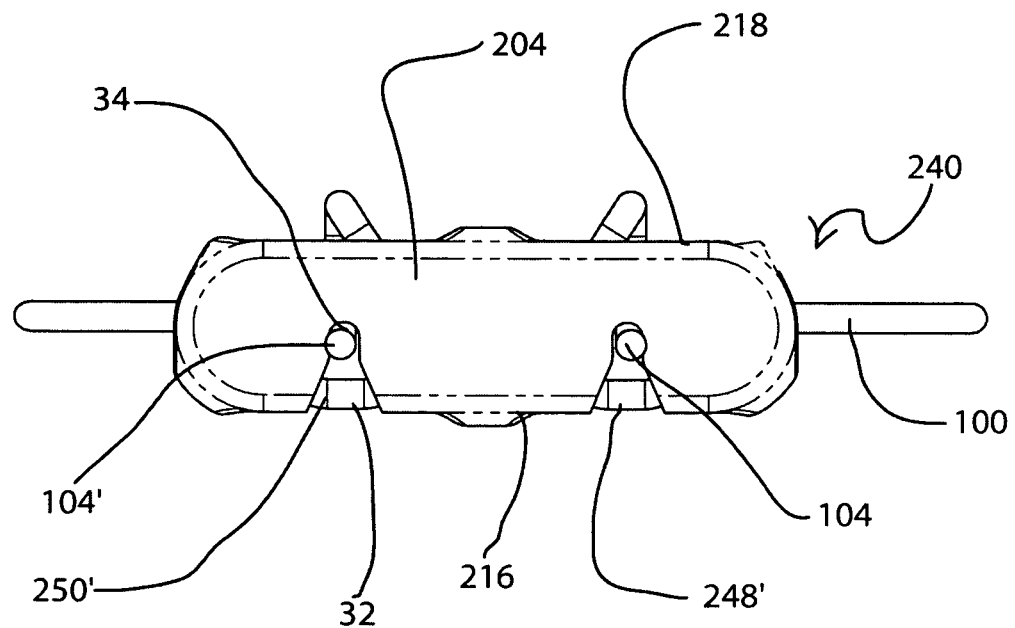
FIG. 18B is a top plan view of the line lock shown in FIG. 18A.
Figure 18C:
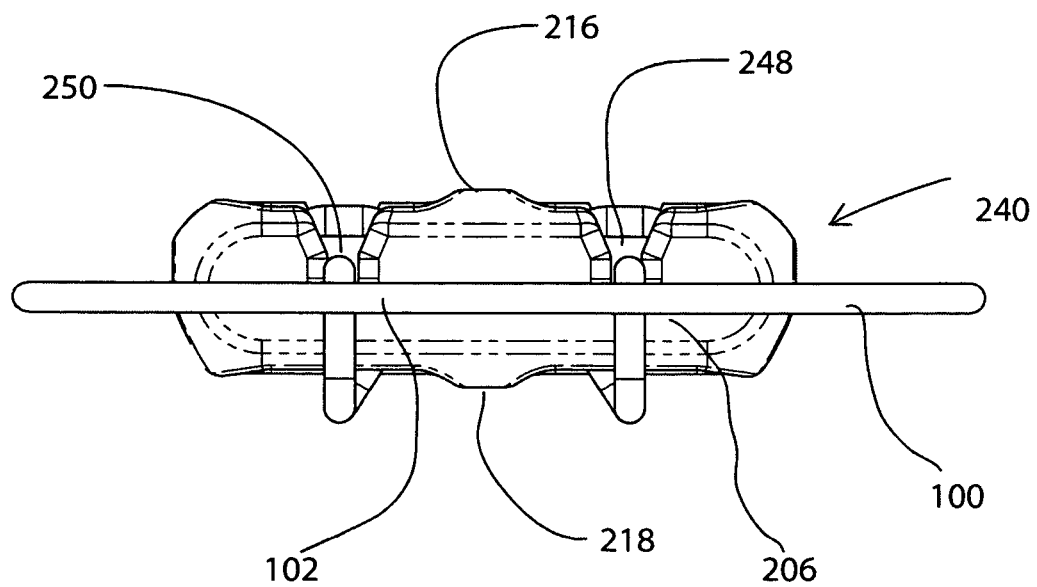
FIG. 18C is a bottom plan view of the line lock shown in FIG. 18A.

During use, as depicted in FIGS. 18A-18C, working end 104 of line 100 is passed through first primary passageway 242 into chamber 220 and then out through first secondary passageway 244. Working end 104 then passes down around bottom wall 206 and is then fed up through first working passageways 248 and 248'. A compression portion 110 of line 100 extends between primary passageway 241 and secondary passageway 244. Working portion 104 is passed between working passageways 248, 248' so that line 100 passes between compression portion 110 and first secondary passageway 244.

Working portion 104' is similarly passed through the passageways on the opposing side of line lock 240. That is, working portion 104' passes through primary passageway 241' and into chamber 220. Working portion 104' then travels out through secondary passageway 244', bends around bottom wall 206, and then travels up through working passageways 250 and 250'.

In the above configuration, slack can be removed from standing portion 102 by pulling line 100 through line lock 240 and/or sliding line lock 240 toward standing portion 102. As line 100 tensions on line lock 240, compression portions 110 and 110' again force portions of line 100 into capture slots 34 of the working passageways so as to secure line 100 to line lock 240 by wedged frictional engagement.

Like line lock 200, line lock 240 provides containment of compression portions 110 and 110' to minimize backlash.

Unlike the other embodiments, line 100 is routed through line lock 240 such that at least one line turn exceeds 90 degrees. For example, the transition between compression portions 110 and 110' and looping portions, designated as 252 and 252', respectively, create 180 degree turns in line 100. These sharp bends in line 100 increase the friction that must be overcome in order to advance line lock 240 toward standing end 102. However, the sharp bends also contribute to greater locking strength of line lock 240 to line 100. This embodiment is beneficial when line 100 is monofilament or single strand line, due to the commonly lower line on line friction and greater flexural stiffness of monofilament line when compared to braided or twisted strand line.

Figure 19:
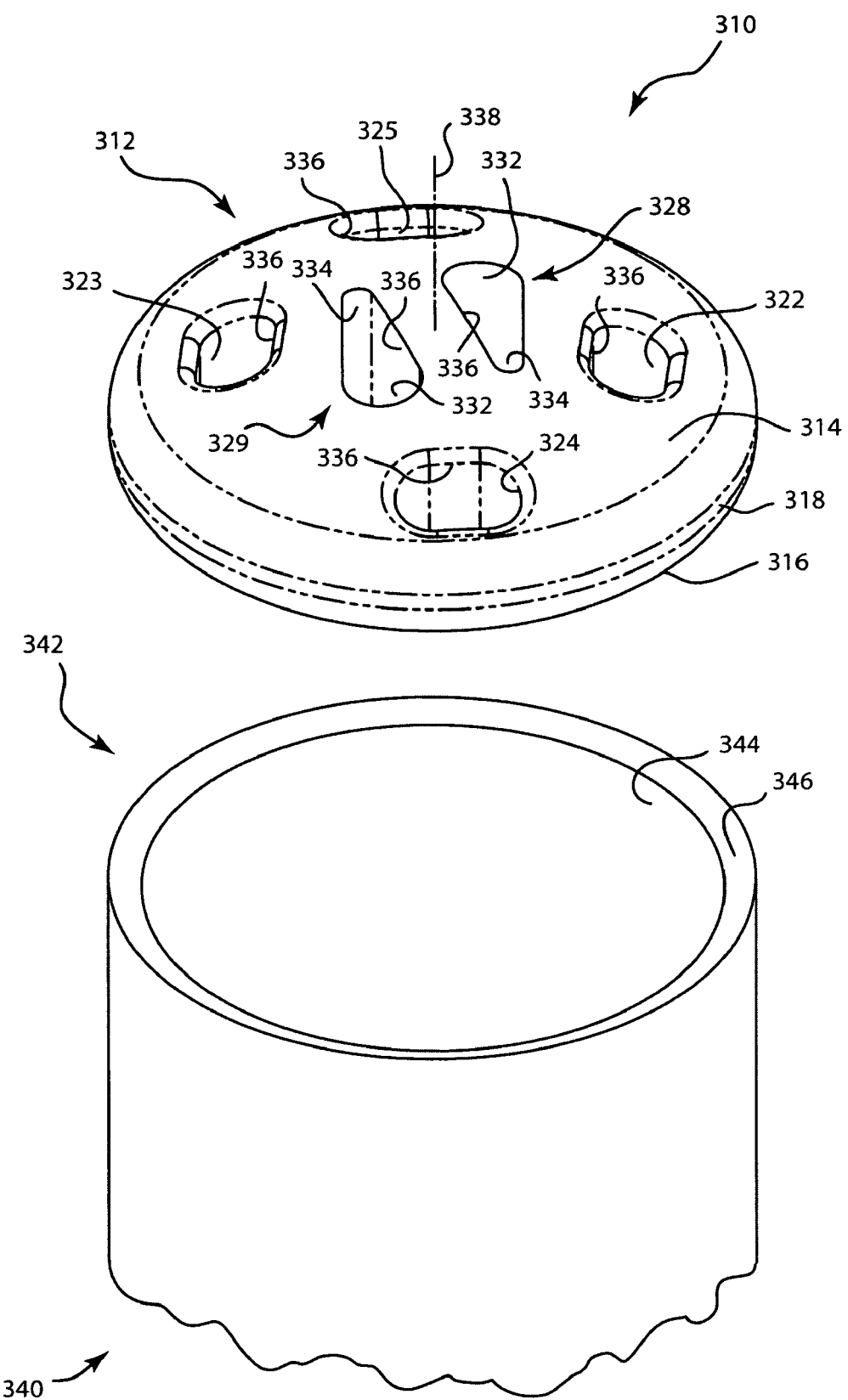
FIG. 19 is a perspective view of a line lock according to another alternative embodiment of the invention, with an associated insertion tool.

Referring to FIG. 19, a perspective view illustrates a line lock 310 according to one alternative embodiment of the invention. As shown, the line lock 310 has a body 312 that is generally disc-shaped. The body 312 has a top surface 314, a bottom surface 316, and a periphery 318 that extends between the top surface 314 and the bottom surface 316 to define a generally circular profile. In this application, a shape having a "generally circular profile" is any shape in which the outside boundary of any cross section passing through the main portion of the shape is substantially circular.

The body 312 bounds a plurality of passageways designed to cooperate receive a line such as a suture. In this application, passageways that "cooperate to receive" a line such as a suture receive the line such that the line passes through all of the cooperating passageways. The passageways of the body 312 include a first primary passageway 322 and a second primary passageway 323, each of which may be positioned adjacent to the periphery 318. The primary passageways 322, 323 are positioned on opposite sides of the body 312.

Furthermore, in the line lock 310 of FIG. 19, the passageways include a first secondary passageway 324 and a second secondary passageway 325, which are also positioned on opposite sides of the body 312, adjacent to the periphery 318. The secondary passageways 324, 325 may be positioned slightly closer to the periphery 318 than the primary passageways 322, 323. Yet further, the passageways also include a first working passageway 328 and a second working passageway 329. The working passageways 328, 329 are relatively centrally located with respect to the body 312.

Each of the primary and secondary passageways 322, 323, 324, 325 may be generally rounded, and may optionally be somewhat elongated to provide an oval cross-section capable of receiving a doubled-over suture end, as when a suture end (not shown) is inserted through a loop (not shown) and drawn through the primary and secondary passageways 322, 323, 324, 325 via the loop. Each of the working passageways 328, 329 may also have a cross-section broad enough to receive a doubled-over suture end.

The passageways 322, 323, 324, 325, 328, 329 intersect the top surface 314 to form corresponding openings, each of which is bounded by one of a plurality of top outside corners 336. The passageways 322, 323, 324, 324, 328, 329 also intersect the bottom surface 316 to form corresponding openings, each of which is bounded by one of a plurality of bottom outside corners (not shown).

As in the description previously set forth, some or all of the top outside corners 336 may have a smaller (i.e., sharper) radius than the corresponding bottom outside corners. More particularly, the top outside corners 336 of the working passageways 328, 329 may have comparatively small radii when compared to the bottom outside corners. In fact, in the embodiment of FIG. 19, the radii of the top outside corners 336 of the working passageways 328, 329 are considerably sharper than those of the top outside corners 336 of the primary and secondary passageways 322, 323, 324, 325. The sharp radii of the top outside corners 336 of the working passageways 328, 329 enhances locking of the suture by the line lock 310.

Each of the working passageways 328, 329 may have a shape that also facilitates locking of the suture, such as the teardrop-shaped cross-section illustrated in FIG. 19. More precisely, each of the working passageways 328 may have an access region 332 and a capture slot 334. The access region 332 is large enough to permit the suture to pass therethrough with clearance. However, the capture slot 334 may be somewhat narrower such that, when the suture is drawn into the capture slot 334, the walls of the capture slot 334 press against the suture to restrict further motion of the suture through the slot 334. The operation of the capture slot 334 will be further shown and described in connection with FIGS. 20 and 21.

In the embodiment of FIG. 19, the first primary, secondary, and working passageways 322, 324, 328 are symmetrically arranged about the center of the body 312 with respect to the second primary, secondary, and working passageways 323, 325, 329. In other words, the first primary, secondary, and working passageways 322, 324, 328 possess radial symmetry with respect to the second primary, secondary, and working passageways 323, 325, 329. Accordingly, if the first primary, secondary, and working passageways 322, 324, 328 were rotated 180° about a central axis 338 of the body 312, they would be substantially superimposed on the second primary, secondary, and working passageways 323, 325, 329.

According to one alternative embodiment, the capture slots 334 may extend at angles with respect to the access regions 332 so that the working passageways 328, 329 may be more compactly arranged, while keeping the capture slots 334 at the desired position and orientation with respect to the first primary and secondary passageways 322, 324 and with respect to the second primary and secondary passageways 323, 325. Such a configuration may potentially provide a more compact line lock (not shown) without losing suture locking capability.

In addition to the line lock 310, FIG. 19 also illustrates an insertion tool 340 that may be used to insert a line lock such as the line lock 310 of FIG. 19 into a relatively constricted space, such as a space within the body accessed via a cannula or the like. The insertion tool 340 has a proximal end (not shown), which may have handle or other structure to facilitate grasping by hand. The insertion tool 340 also has a distal end 342 and a hollow bore 344 that may extend along the entire displacement between the proximal end and the distal end 342 so that sutures or other items can be inserted into one end of the hollow bore 344 and retrieved from the opposite end. The distal end 342 has a rim 346, which may have an annular shape, a frustoconical shape, or the like, such that the body 312 is able to seat against the rim 346. The insertion tool 340 can thus be used to advance the line lock 310. The insertion tool 340 is illustrated proximate the bottom side 316 of the body 312 for clarity in FIG. 19; however, in use, the insertion tool 340 generally abuts the top side 314 and the periphery 318. The manner in which the insertion tool 340 is used to advance the line lock 310 will be more fully set forth in the description of FIG. 20.

Figure 20:
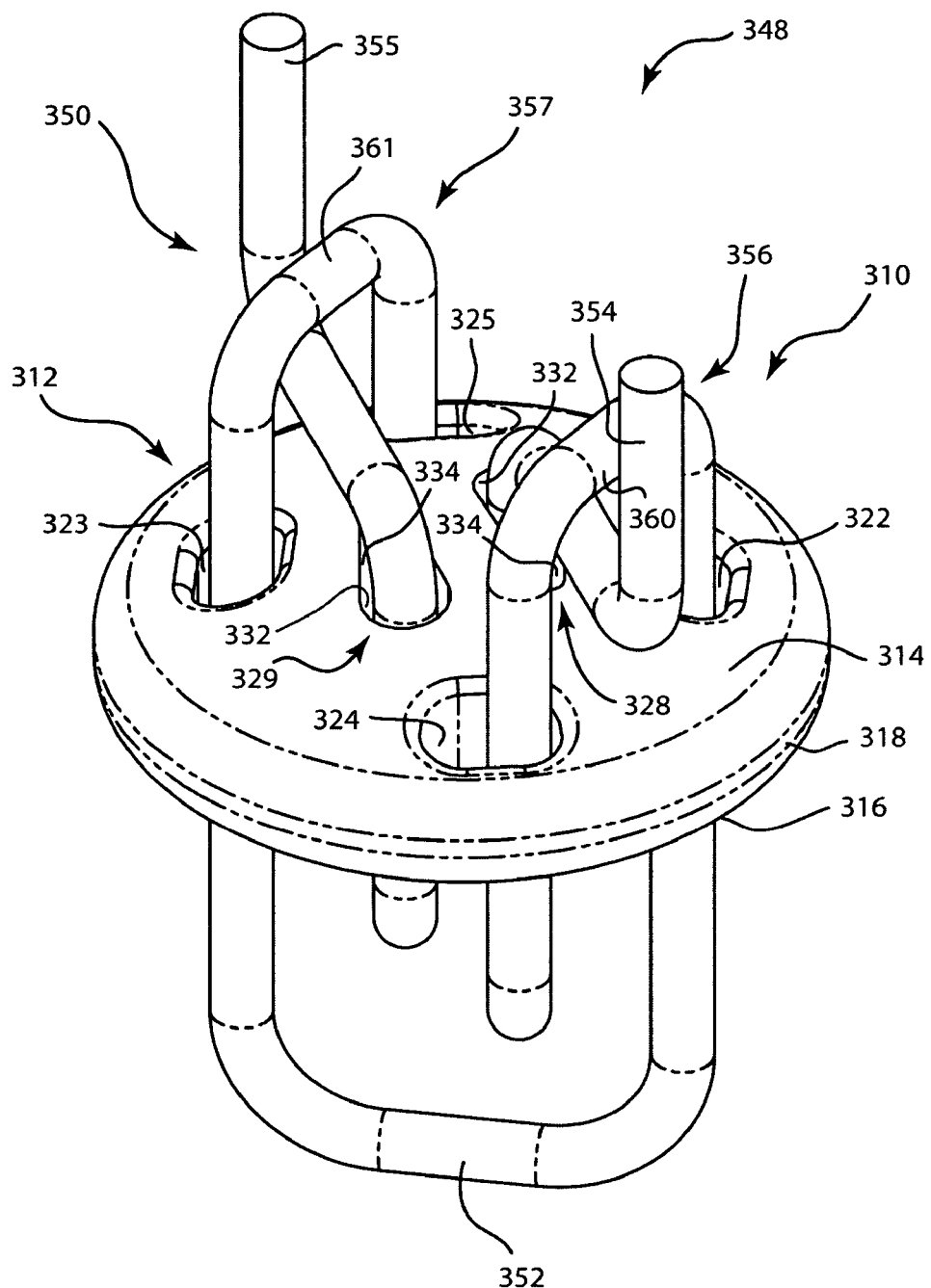
FIG. 20 is a perspective view of the line lock of FIG. 19, with a suture passing loosely through the passageways of the line lock.

Referring to FIG. 20, a perspective view illustrates a system 348 including the line lock 310 of FIG. 19 and a suture 350 relatively loosely passing through the passageways 322, 323, 324, 325, 328, 329 of the body 312. The suture 350 may be similar or identical to that described previously. Accordingly, the suture 350 may have a standing portion 352, which is the portion of the suture 350 that is placed under tension and constrained by advancement of the line lock 310, first and second working portions 354, 355, which are handled by a user, and first and second locking portions 356, 357 that are positioned between the standing portion 352 and the first and second working portions 354, 355, respectively.

The suture 350 may be inserted through the passageways 322, 323, 324, 325, 328, 329 according to a wide variety of methods. For example, the suture 350 may be inserted by hand. Alternatively, the suture 350 may be inserted through the use of threaders (not shown) that are initially routed through the passageways 322, 323, 324, 325, 328, 329 along the proper pathways. The threaders may have leading ends designed to be drawn by hand, and trailing ends with loops or other features capable of capturing and drawing the suture ends.

Thus, a user may simply attach the ends of the suture 350 to the trailing ends of the threaders, and then pull the threaders until the suture 350 passes through the passageways 322, 323, 324, 325, 328, 329 along the desired pathways. The ends of the suture 350 may then be removed from the trailing ends of the threaders. In addition to or in the alternative to the use of threaders, a cartridge (not shown) may be used to retain the line lock 310 and guide the suture 350 through the passageways 322, 323, 324, 325, 328, 329 along the desired pathways.

As illustrated in FIG. 20, the first locking portion 356 extends from the standing portion 352 through the first primary passageway 322, then through the first secondary passageway 324, and then through the first working passageway 328. From the first working passageway 328, the first working portion 354 extends between the top surface 314 and the section of the first locking portion 356 that passes from the first primary passageway 322 to the first secondary passageway 324. This section of the first locking portion 356 is a first compression section 360 of the suture 350.

Similarly, the second locking portion 357 extends from the standing portion 352 through the second primary passageway 323, then through the second secondary passageway 325, and then through the second working passageway 329. From the second working passageway 329, the second working portion 355 extends between the top surface 314 and the section of the second locking portion 357 that passes from the second primary passageway 323 to the second secondary passageway 325. This section of the second locking portion 357 is a second compression section 361 of the suture 350.

The standing portion 352 may be inserted through and/or around some feature (not shown), such as bodily tissue, that is to be retained by the system 348. The standing portion 352 may additionally or alternatively pass through an opening of a bone anchor or the like to enable tissues to be anchored to the bone, as in rotator cuff repair. From the configuration of FIG. 20, the suture 350 may be tightened by advancing the line lock 310 along the standing portion 352. The line lock 310 may be advanced by holding the working portions 354, 355 and pressing the body 312 toward the standing portion 352.

According to one method, the line lock 310 may be advanced along the standing portion 352 through the use of a tool such as the insertion tool 340 of FIG. 19. More precisely, the working portions 354, 355 may first be inserted into the hollow bore 344 at the distal end 342. The working portions 354, 355 are inserted through the hollow bore 344 such that they protrude from the hollow bore 344 at the proximal end. A user may then grasp the working portions 354, 355 and draw them proximally, while holding the insertion tool stationary or advancing it distally, until there remains no slack in the working portions 354, 355, and the body 312 is seated against the rim 346 of the distal end 342. The shape of the rim 346 may tend to draw the body 312 into a position and orientation coaxial with the insertion tool 340 to facilitate insertion of the line lock 310 into a relatively narrow space.

Once the slack has been removed from the working portions 354, 355, further tension on the working portions 354, 355 tends to cause the locking portions 356, 357 to advance through the passageways 322, 323, 324, 325, 328, 329, moving from the primary passageways 322, 323 toward the working passageways 328, 329. Motion of the locking portions 356, 357 in this direction is relatively unrestricted since the compression sections 360, 361 remain slack, thereby allowing the locking portions 356, 357 to move through the access regions 332 of the working passageways 328, 329. Consequently, the line lock 310 is able to advance along the standing portion 352, thereby causing the standing portion 352 to tighten.

In alternative to use of a tool such as the insertion tool 340 of FIG. 19, the line lock 310 may be advanced along the standing portion 352 without any tooling. For example, the line lock 310 may be pressed and moved along the standing portion 352 by direct pressure from a finger. Alternatively, grasping the working portions 354, 355 and pulling them in substantially opposite and/or co-linear directions may cause the line lock 310 to advance along the standing portion 352. Each of the working portions 354, 355 may then lie along the top surface 314, but may not pass through the corresponding capture slot 334 until locking is performed. Such a technique may be particularly useful for retaining tissues in more readily accessible areas, where the working portions 354, 355 can be oriented and drawn in opposite directions. Use of insertion tooling may be more appropriate for more confined spaces.

Figure 21:
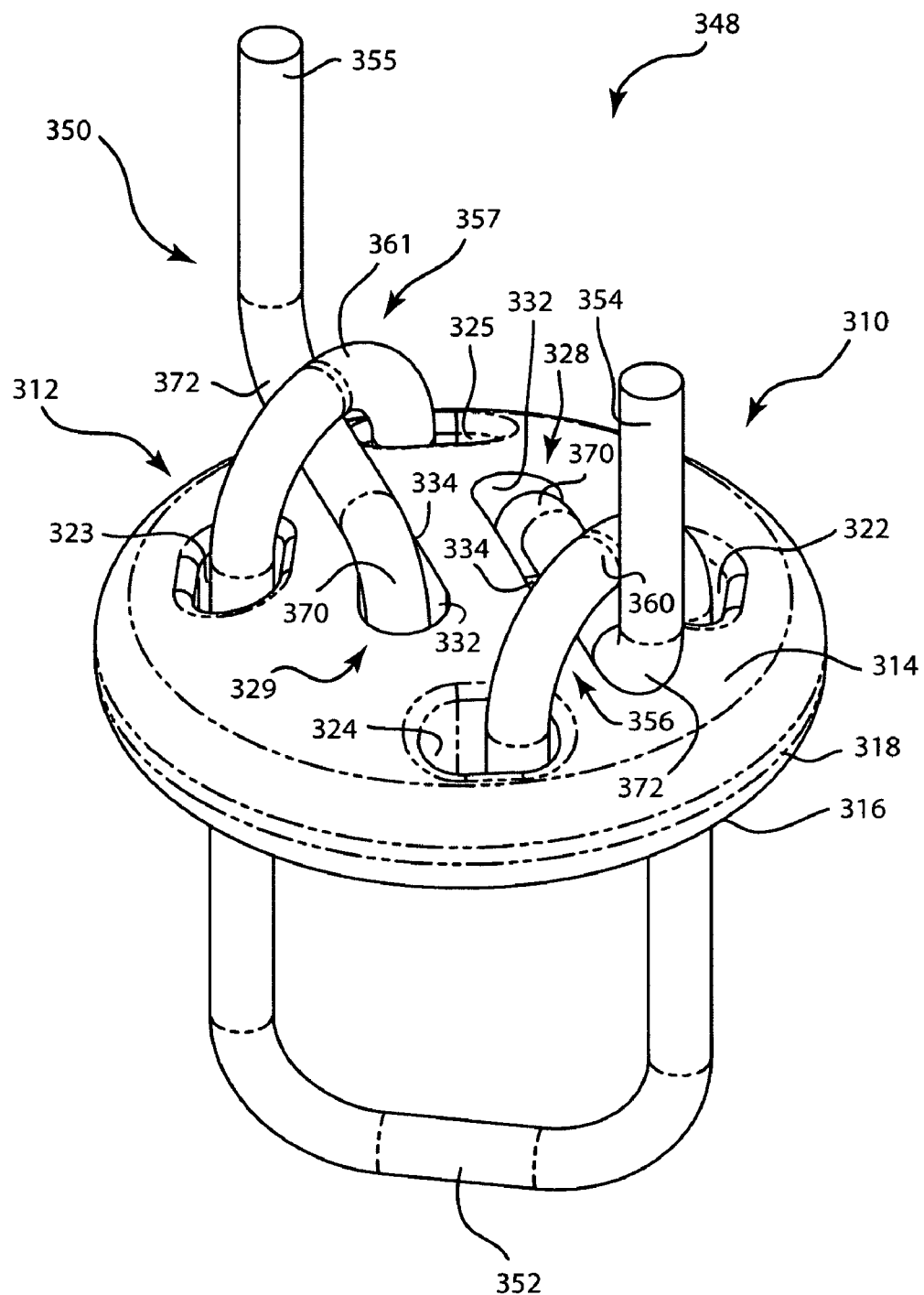
FIG. 21 is a perspective view of the line lock of FIG. 19, with suture passing tightly through the passageways of the line lock.

Referring to FIG. 21, a perspective view illustrates the system 348 of FIG. 20, with the suture 350 routed relatively tightly through the passageways 322, 323, 324, 325, 328, 329. As the standing portion 352 tightens, tension in the standing portion 352 causes the compression sections 360, 361 to become taught. The compression sections 360, 361 straighten, thereby drawing the portions of the suture 350 within the working passageways 328, 329 outward, into the capture slots 334. The sections of the working portions 354, 355 adjacent to the working passageways 328, 329 are pinned against the top surface 314 by the compression sections 360, 361.

Accordingly, each of the working portions 354, 355 is bent twice, with each bend having an angle of about ninety degrees. A first bend 370 is about the top outside corner 336 (as labeled in FIG. 19) of each corresponding working passageway 328, 329, and a second bend 372 is about the corresponding compression section 360, 361. As mentioned previously, the top outside corners 336 of the working passageways 328, 329 have tight radii. Accordingly, the top outside corners 336 of the working passageways 328, 329 provide relatively high friction surfaces, particularly when the working portions 354, 355 are pressed against them via tension, like that applied by the compression sections 360, 361. The compression sections 360, 361 may also provide considerable friction, depending on the structure and material of the suture 350.

Due to the friction applied to the bends 370, 372 of each of the working portions 354, 355 by the tensioned standing portion 352, the working portions 354, 355 are generally unable to retract back into the working passageways 328, 329. However, the standing portion 352 may still be tightened by further drawing on the working portions 354, 355. Tension in the working portions 354, 355 tends to pull the compression sections 360, 361 inward, thereby removing the bends 370, 372 and relieving the associated sources of friction. Further advancement of the body 312 along the standing portion 352 only increases the level of tension in the standing portion 352 so that, when tension on the working portions 328, 329 is relieved, the working portions 328, 329 are again drawn to the locked configuration.

After the locking portions 356, 357 have been locked via tension in the standing portion 352, the working portions 354, 355 may be cut short, for example, just outside the second bends 372. The friction on the bends 370, 372 keeps slippage to a level low enough that cutting the working portions 354, 355 in such a manner does not impair the operation of the line lock 310. The second bends 372 may disappear because there is no longer tension drawing the working portions 354, 355 to the orientation illustrated in FIG. 21. However, the second bends 372 are not required for locking; rather, the compression sections 360, 361 continue to press the suture 352 against the top surface 314, adjacent to the first bends 370. The friction of this compression interface, in addition to that of the first bends 370, is sufficient to keep the suture 350 from slipping back through the passageways 322, 323, 324, 325, 328, 329.

If desired, the line lock 310 and/or the suture 350 may be formed of biodegradable materials. Alternatively, the line lock 310 and the suture 350 may be small and compact enough that they can remain in the body indefinitely without causing any discomfort or significant health risks.

Figure 22:
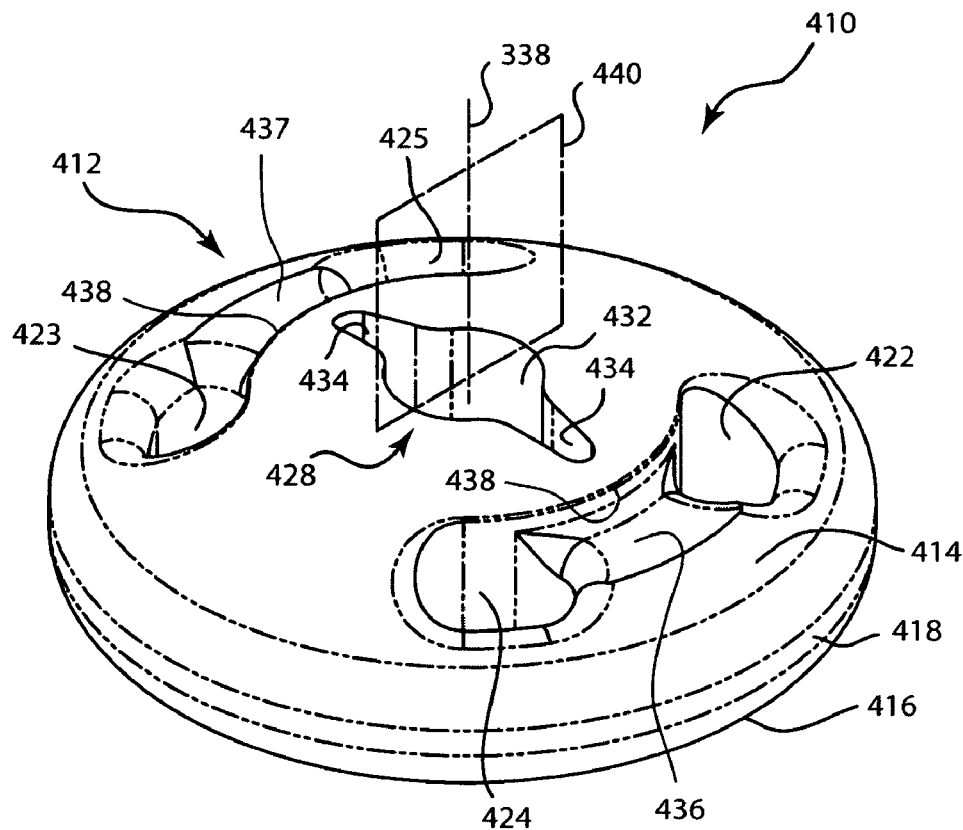
FIG. 22 is a perspective view of a line lock according to another alternative embodiment of the invention.

Referring to FIG. 22, a perspective view illustrates a line lock 410 according to another alternative embodiment of the invention. As in the previous embodiment, the line lock 410 has a body 412 that is generally disc-shaped. The body 412 has a top surface 414, a bottom surface 416, and a periphery 418 extending between the top surface 414 and the bottom surface 416 to provide the generally circular profile of the body 412. Furthermore, the body 412 bounds a first primary passageway 422, a second primary passageway 423, a first secondary passageway 424, and a second secondary passageway 425. The first passageways 422, 424 possess multiple forms of symmetry with respect to the second passageways 423, 425, as will be described subsequently. The passageways 422, 423, 424, 425 are also adjacent to the periphery 418.

In addition to the passageways 422, 423, 424, 425, the body 412 bounds a first working passageway 428. The first working passageway 428 has an access region 432 and a pair of capture slots 434 extending from either side of the access region 432. The first working passageway 428 accommodates both locking portions 356, 357 of the suture 350. Accordingly, the access region 432 is large enough to simultaneously receive two suture portions with clearance, and each of the capture slots 434 is sized to compress one of the suture portions.

The body 412 also defines a first groove 436 and a second groove 437, both of which are formed in the top surface 414. The first groove 436 extends along a generally arcuate path between the first primary and secondary passageways 422, 424. Similarly, the second groove 437 extends along a generally arcuate path between the second primary and secondary passageways 423, 425. The first and second grooves serve to provide a pair of sharpened lips 438 adjacent to each of the capture slots 434 of the first working passageway 428.

As shown in FIG. 22, the passageways 422, 423, 424, 425, 428 are symmetrical to each other about a central axis 338 of the body 412. This is because, if rotated 180° about the central axis 338, the first primary and secondary passageways 422, 424 would be superimposed on the second primary and secondary passageways 423, 425, and the first working passageway 428 would be superimposed on itself. Furthermore, the passageways 422, 423, 424, 425, 428 are symmetrical to each other about a plane 440 passing through the center of the body 412. This is because, if reflected across the plane 440, the first primary and secondary passageways 422, 424 would be superimposed on the second primary and secondary passageways 423, 425, and the first working passageway 428 would be superimposed on itself.

The suture 350 may be routed through the passageways 422, 423, 424, 425, 428 of the line lock 410 in a manner similar to that of the line lock 310. However, rather than being routed through two different working passageways 328, 329, the locking portions 356, 357 are both routed through the first working passageway 428. From the working passageway 428, the first working portion 354 extends between the first compression section 360 and the first groove 436, and the second working portion 355 extends between the second compression section 361 and the second groove 437.

The line lock 410 provides locking in a manner somewhat similar to that of the previous embodiment. More precisely, when the compression sections 360, 361 press the working portions 354, 355, respectively, against the top surface 414, the suture 350 becomes wedged in the capture slots 434. Additionally, the compression sections 360, 361 press the working portions 354, 355 against the grooves 436, 437, respectively. As shown, the compression sections 360, 361 may extend generally parallel to the grooves 436, 437 and the working portions 354, 355 may extend generally perpendicular to the grooves 436, 437. Accordingly, the working portions form bends (not shown) where they extend over the sharpened lips 438 of the grooves 436, 437. The sharpened lips 438 provide additional friction tending to resist motion of the working portions 354, 355 toward the first working passageway 428.

Otherwise, operation of the line lock 410 is similar to that of the line lock 310 of the previous embodiment. The suture 350 may be inserted into the passageways 422, 423, 424, 425, 428, tightened, and locked within the line lock 410 in any of the ways set forth in connection with the previous embodiment. As described above, the working portions 354, 355 may be cut short after the suture 350 has been tightened and locked by the line lock 410. The line lock 410 may also be formed of a variety of biodegradable or non-biodegradable materials. The text setting forth potential suture threading methods, line lock advancement methods, materials, and the like for the line lock 310 may also apply to the line lock 410 and/or any other embodiment of the invention.

Figure 23:
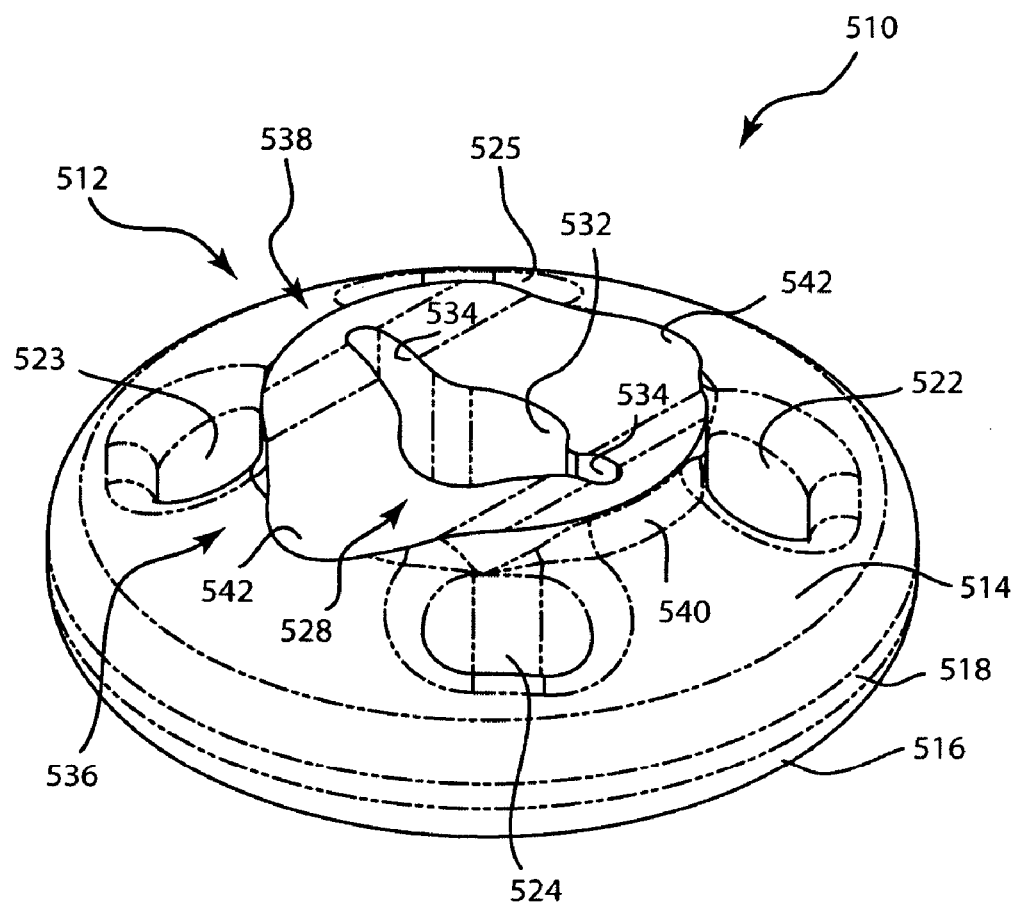
FIG. 23 is a perspective view of a line lock according to another alternative embodiment of the invention.

Referring to FIG. 23, a perspective view illustrates a line lock 510 according to another embodiment of the invention. As in the previous embodiment, the line lock 510 has a body 512 with a disc-like shape. The body 512 has a top surface 514, a bottom surface 516, and a periphery 518 arranged between the top surface 514 and the bottom surface 516 to define the circular profile of the body 512. The body 512 bounds a first primary passageway 522, a second primary passageway 523, a first secondary passageway 524, a second secondary passageway 525, and a first working passageway 528.

As in the previous embodiment, the first working passageway 528 has an access region 532 and a pair of oppositely disposed capture slots 534. However, in place of the grooves 436, 437 of the previous embodiment, the body 512 has a central plateau 536 around which the primary and secondary passageways 522, 523, 524, 525 are arranged. The first working passageway 528 extends through the central plateau 536.

The central plateau 536 may be somewhat tapered so as to form a sharpened rim 538. The central plateau 536 has a concave surface 540 that passes along a generally circular pathway between the sharpened rim 538 and the remainder of the body 512. The sharpened rim 538 has a pair of ears 542 that extend between the first primary passageway 522 and the second secondary passageway 525, and between the second primary passageway 523 and the first secondary passageway 524. The top surface of the central plateau 536 elevates as it extends outward, along the capture slots 534.

The suture 350 may be routed through the passageways 522, 523, 524, 525, 528 of the line lock 510 in a manner similar to that of the line lock 410 of the previous embodiment. Accordingly, both locking portions 356, 357 of the suture 350 will extend through the first working passageway 528. The first working portion 354 will extend from the first working passageway 528 to lie along the central plateau 536 and the top surface 514 between the first primary and secondary passageways 522, 524. The second working portion 355 will extend from the first working passageway 528 to lie along the central plateau 536 and the top surface 514 between the second primary and secondary passageways 523, 525.

When the standing portion 352 is tensioned, the compression sections 360, 361 will compress the working portions 354, 355 against the sharpened rim 538 of the central plateau 536, thereby forming bends and applying friction to keep the working portions 354, 355 from moving back toward the first working passageway 528. The sharpened rim 538 effectively forms a function similar to that of the sharpened lips 438 of the grooves 436, 437 of the previous embodiment. The compression sections 360 may tend to slide outward to either side of the central plateau 536 to enhance the bends formed in the working portions 354, 355.

Figure 24:
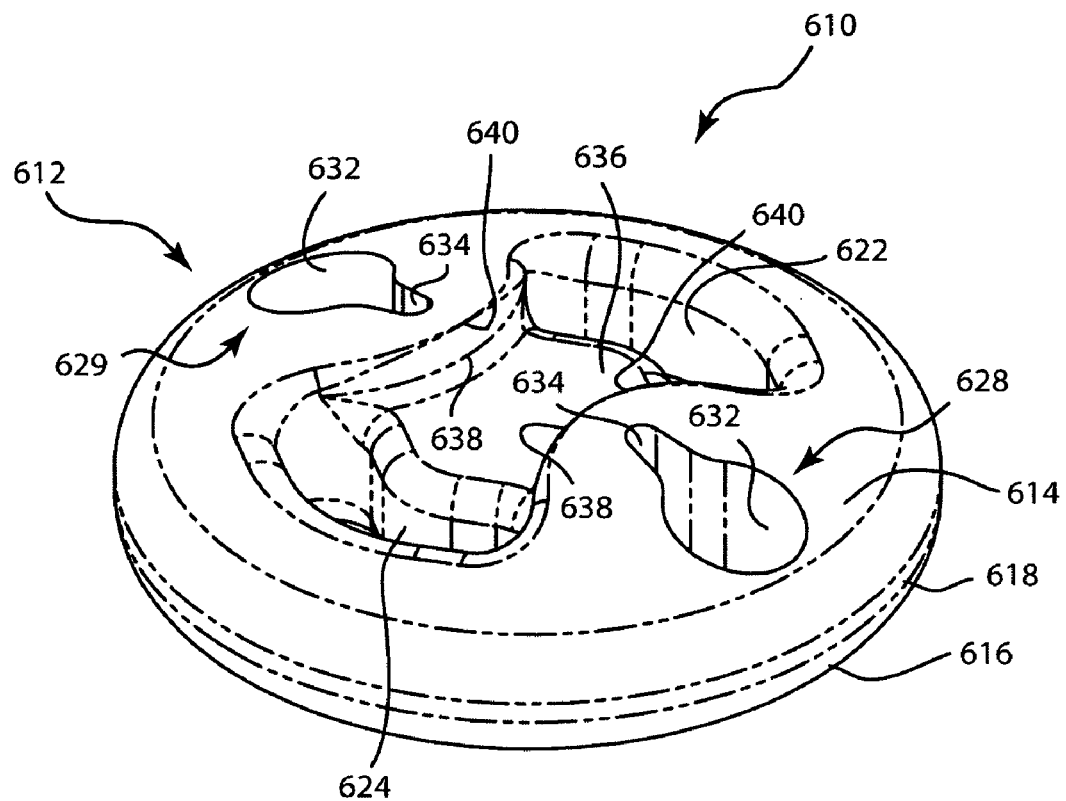
FIG. 24 is a perspective view of a line lock according to another alternative embodiment of the invention.

Referring to FIG. 24, a perspective view illustrates a line lock 610 according to another alternative embodiment of the invention. The line lock 610 has a body 612 with a disc-like shape. The body 612 has a top surface 614, a bottom surface 616, and a periphery 618 that extends between the top surface 614 and the bottom surface 616 to define the generally circular profile of the body 612. The body 612 bounds a first primary passageway 622 and a first secondary passageway 624, but no second primary or secondary passageways. The first primary and secondary passageways 622, 624 are generally arc-shaped, and each of the first primary and secondary passageways 622, 624 is broad enough to accommodate multiple passes of the suture 350.

The body 612 also bounds a first working passageway 628 and a second working passageway 629. The working passageways 628, 629 may be shaped similarly to the working passageways 328, 329 of the embodiment of FIG. 19, in that each of the working passageways 628, 629 has a keyhole-like shape with an access region 632 sized to permit passage of the suture 350 with clearance, and a capture slot 634 sized to grip the suture 350. The capture slots 634 are oriented inward, toward the center of the body 612.

The body 612 also has a central depression 636 positioned between the first primary and secondary passageways 622, 624. The central depression 636 may have a bowtie-like shape. The central depression 636 has side walls 638 that extend generally perpendicular to the top surface 614. Sharpened edges 640 are formed by the intersection of the side walls 638 with the top surface 614. The sharpened edges 640 serve to enhance locking of the suture 350 in a manner that will be set forth in connection with FIGS. 25 and 26.

Figure 25:
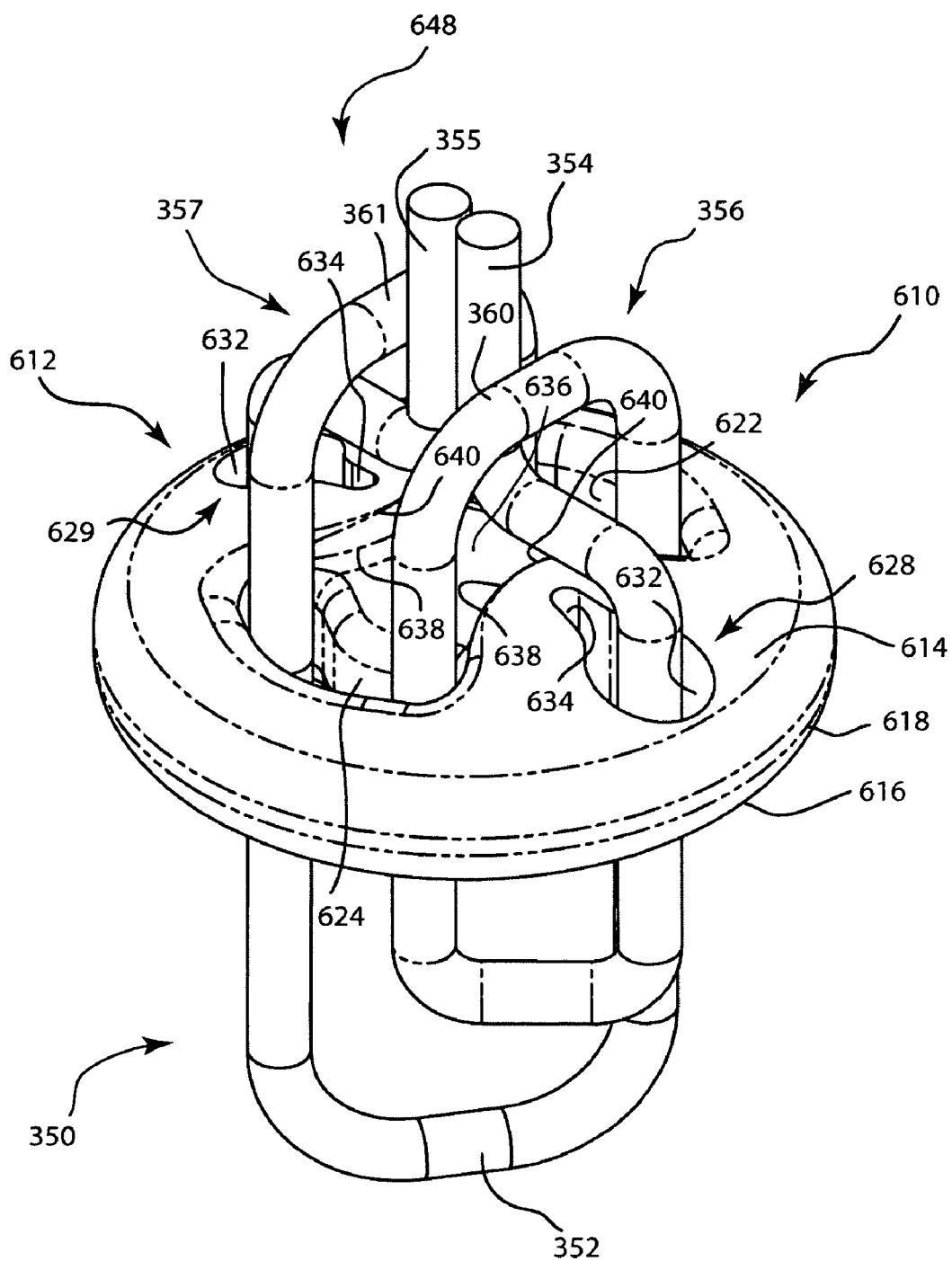
FIG. 25 is a perspective view of the line lock of FIG. 24, with a suture passing loosely through the passageways of the line lock.

Referring to FIG. 25, a perspective view illustrates a system 648 including the line lock 610 and the suture 350 passing through the passageways 622. 624, 628, 629 in a relatively loose configuration. As shown, the first locking portion 356 passes first through the first primary passageway 622, and then through the first secondary passageway 624 to define the first compression section 360. The second locking portion 357 passes first through the first secondary passageway 624 and then through the first primary passageway 622 to define the second compression section 361.

From the first secondary passageway 624, the first locking portion 356 passes through the first working passageway 628, and the first working portion 354 extends from the first working passageway 628, between the top surface 614 and the first compression section 360. Similarly, from the first primary passageway 622, the second locking portion 357 passes through the second working passageway 629, and the second working portion 355 extends from the second working passageway 629, between the top surface 614 and the second compression section 361.

Figure 26:
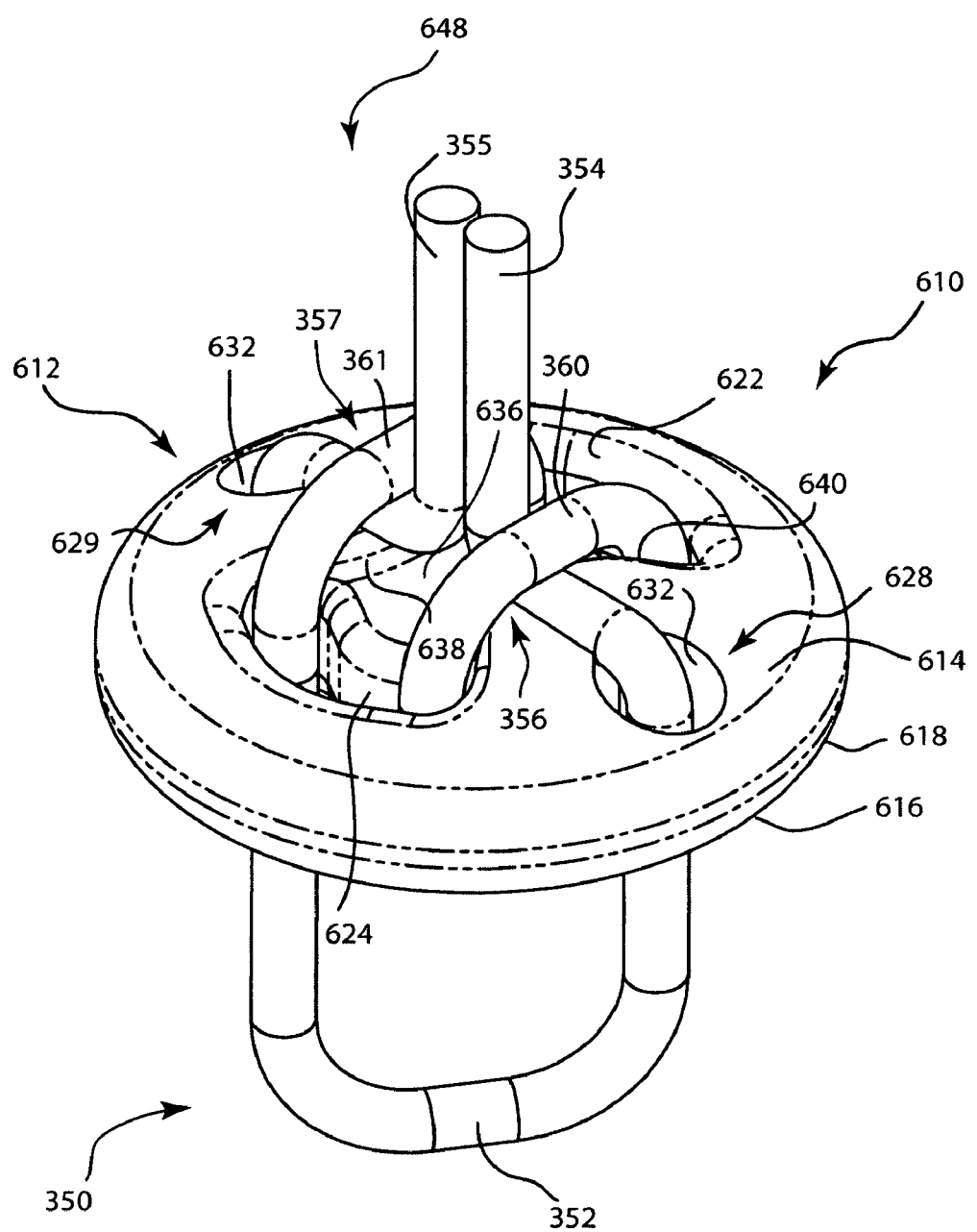
FIG. 26 is a perspective view of the line lock of FIG. 24, with suture passing tightly through the passageways of the line lock.

Referring to FIG. 26, a perspective view illustrates the assembly 648 of FIG. 25, with the suture 350 passing relatively tightly through the passageways 622, 624, 628, 629. When the standing portion 352 is tensioned, the compression sections 360, 361 press the working portions 354, 355 against the top surface 614 and/or into the central depression 636. The working portions 354, 355 are also pressed against the sharpened edges 640 to form bends in the working portions 354, 355 and to provide friction to keep the working portions 354, 355 from moving toward the working passageways 628, 629, respectively. The sharpened edges 640 effectively serve a function similar to that of the sharpened rim 538 and the sharpened lips 438 of previous embodiments.

Figure 27:
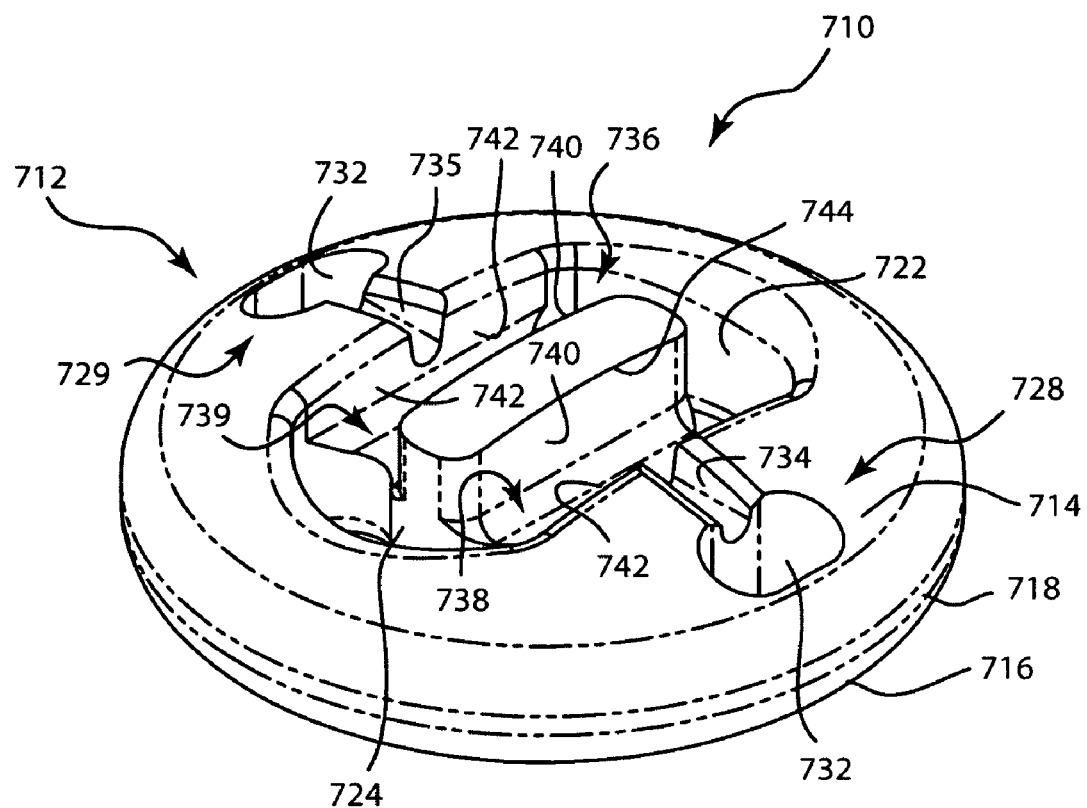
FIG. 27 is a perspective view of a line lock according to another alternative embodiment of the invention.

Referring to FIG. 27, a perspective view illustrates a line lock 710 according to another alternative embodiment of the invention. As in previous embodiments, the line lock 710 has a body 712 with a disc-like shape. The body 712 has a top surface 714, a bottom surface 716, and a periphery 718 that extends between the top surface 714 and the bottom surface 716 to define the generally circular profile of the body 712. The body 712 bounds a first primary passageway 722 and a first secondary passageway 724. The first primary and secondary passageways 722, 724 are generally arc-shaped, and each of the first primary and secondary passageways 722, 724 is broad enough to accommodate multiple passes of the suture 350.

The body 712 further bounds a first working passageway 728 and a second working passageway 729. Each of the working passageways 728, 729 includes an access region 732 that is sized to permit passage of the suture 350 therethrough with clearance. Furthermore, the body 712 has a first trough 734 adjoining the first working passageway 728 and a second trough 735 adjoining the second working passageway 729. The troughs 734, 735 are sized to press against the suture 350 to keep the suture 350 from sliding freely through the troughs 734, 735.

The body 712 also has a central plateau 736, a first groove 738, and a second groove 739. The grooves 738, 739 are positioned on either side of the central plateau 736 such that the first groove 738 lies between the central plateau 736 and the first working passageway 728 and the second groove 739 lies between the central plateau 736 and the second working passageway 729. The grooves 738, 739 are relatively straight and connect opposing ends of the first primary and secondary passageways 722, 724 together.

The grooves 738, 739 define a pair of inner walls 740 and a pair of outer walls 742, all of which extend generally perpendicular to the top surface 714. The inner walls 740 also provide the sides of the central plateau 736 and define sharpened edges 744 where they intersect the top surface of the central plateau 736.

Figure 28:
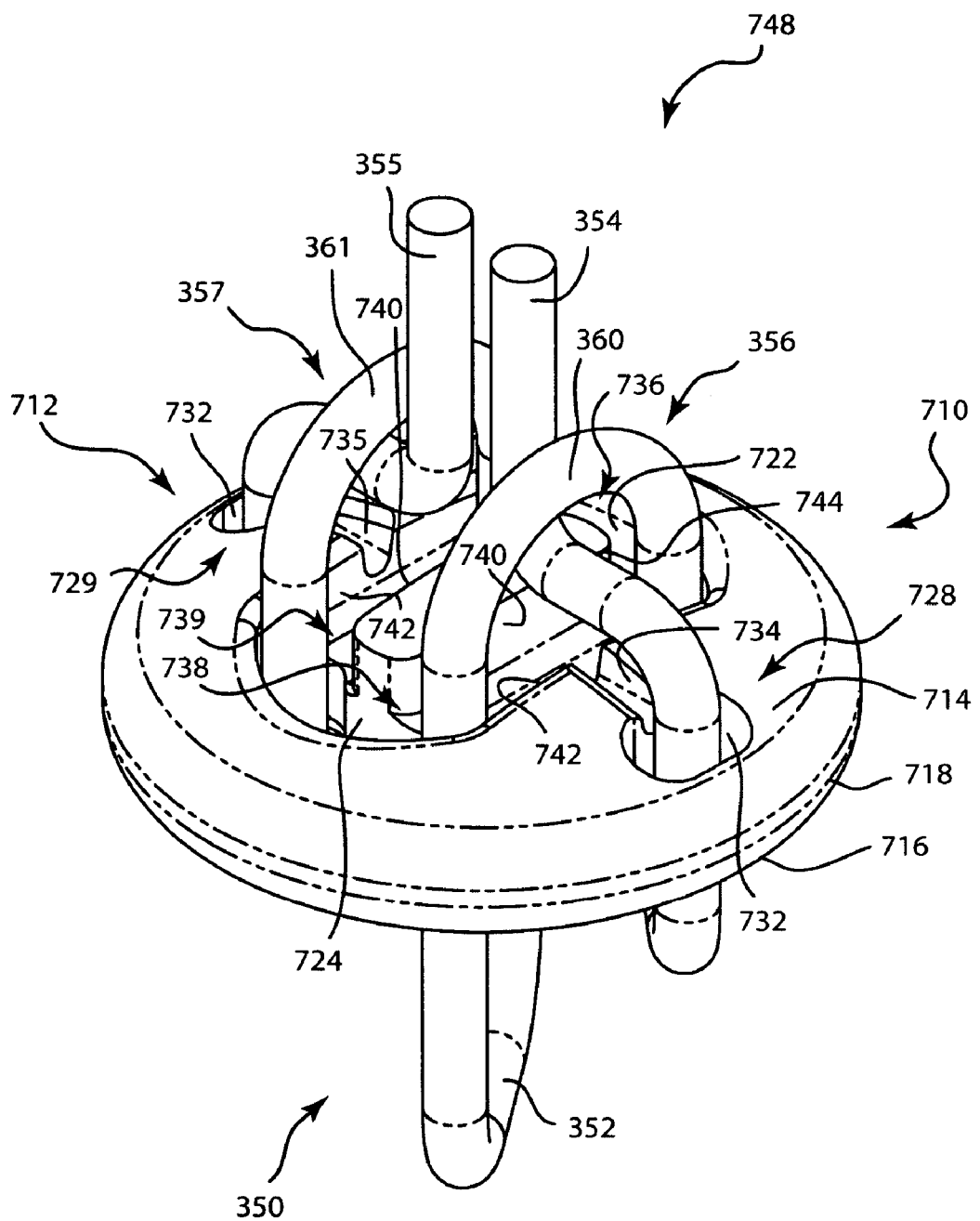
FIG. 28 is a perspective view of the line lock of FIG. 27, with a suture passing loosely through the passageways of the line lock.

Referring to FIG. 28, a perspective view illustrates a system 748 including the line lock 710 of FIG. 27 and the suture 350 passing relatively loosely through the passageways 722, 724, 728, 729 of the line lock 710. If desired, the suture 350 may be routed through the passageways 722, 724, 728, 729 in a manner very similar to that of the previous embodiment. Alternatively, as shown in FIG. 28, the first locking portion 356 may pass through the first secondary passageway 724, then through the first primary passageway 722, thereby defining the first compression section 360, and then through the first working passageway 728. Similarly, the second locking portion 357 may pass through the first primary passageway 722, then the first secondary passageway 724, thereby defining the second compression section 361, and then through the second working passageway 729.

From the first working passageway 728, the first working portion 354 passes between the first compression section 360 and the top surface 614 and/or the first trough 734 and the first groove 738. Similarly, from the second working passageway 729, the second working portion 355 passes between the second compression section 361 and the top surface 714 and/or the second trough 735

Figure 29:
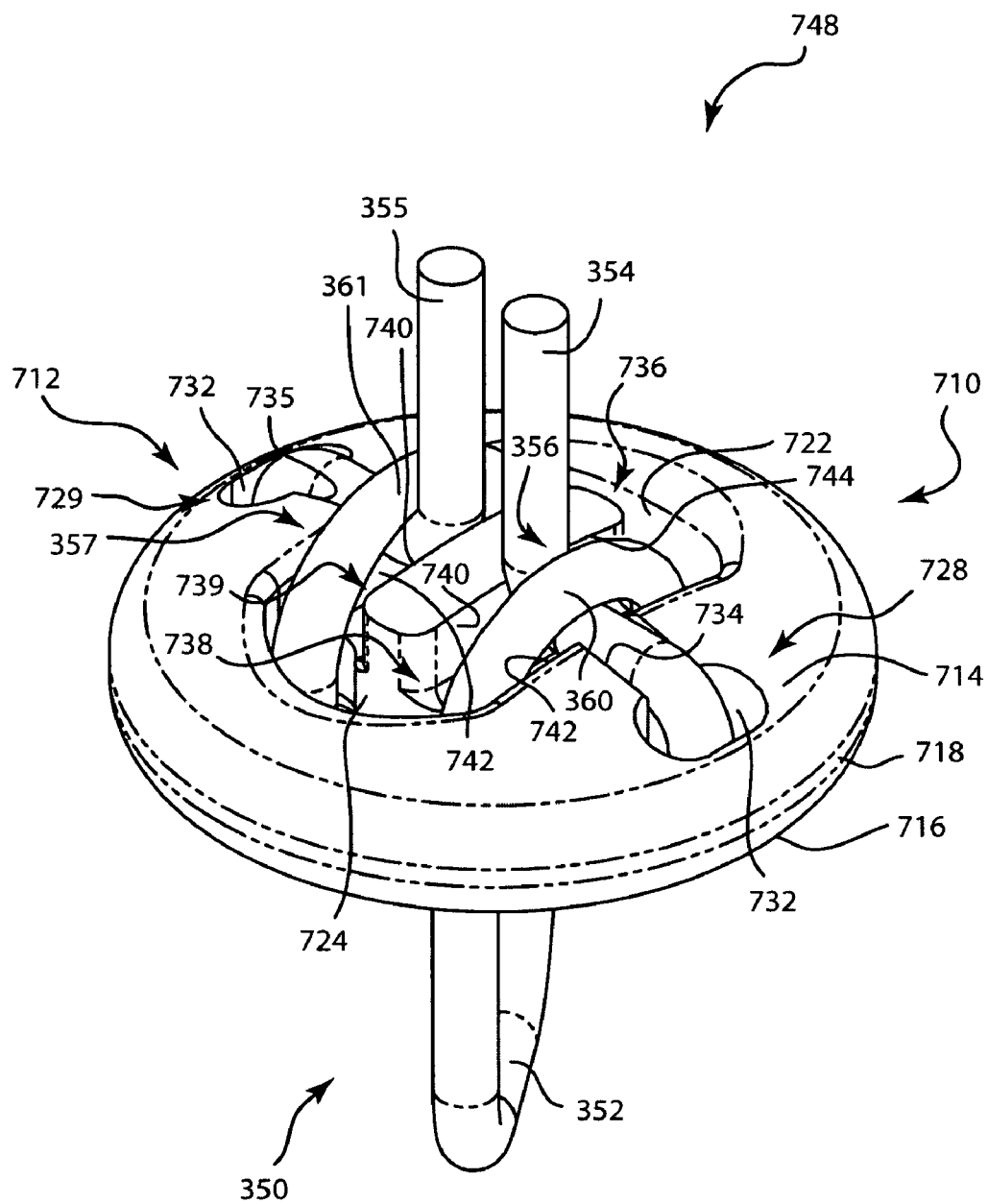
FIG. 29 is a perspective view of the line lock of FIG. 27, with suture passing tightly through the passageways of the line lock.

Referring to FIG. 29, a perspective view illustrates the system 748 of FIG. 28, with the suture 350 routed relatively tightly through the passageways 722, 724, 728, 729 of the line lock 710. When the standing portion 352 is tensioned, the compression sections 360, 361 press the working portions 354, 355 against the top surface 714, the troughs 734, 735, the grooves 738, 739, and the sharpened edge 744. The sharpened edge 744 helps to form a bend in each of the working portions 354, 355, and to provide friction that keeps the working portions 354, 355 from moving back toward the working passageways 728, 729. The working portions 354, 355 are also pressed into the troughs 734, 735, which add additional friction. Part of each of the working portions 354, 355 may be pressed into the grooves 738, 739 to enhance bending of the working portions 354, 355, thereby providing stronger locking.

Figure 30:
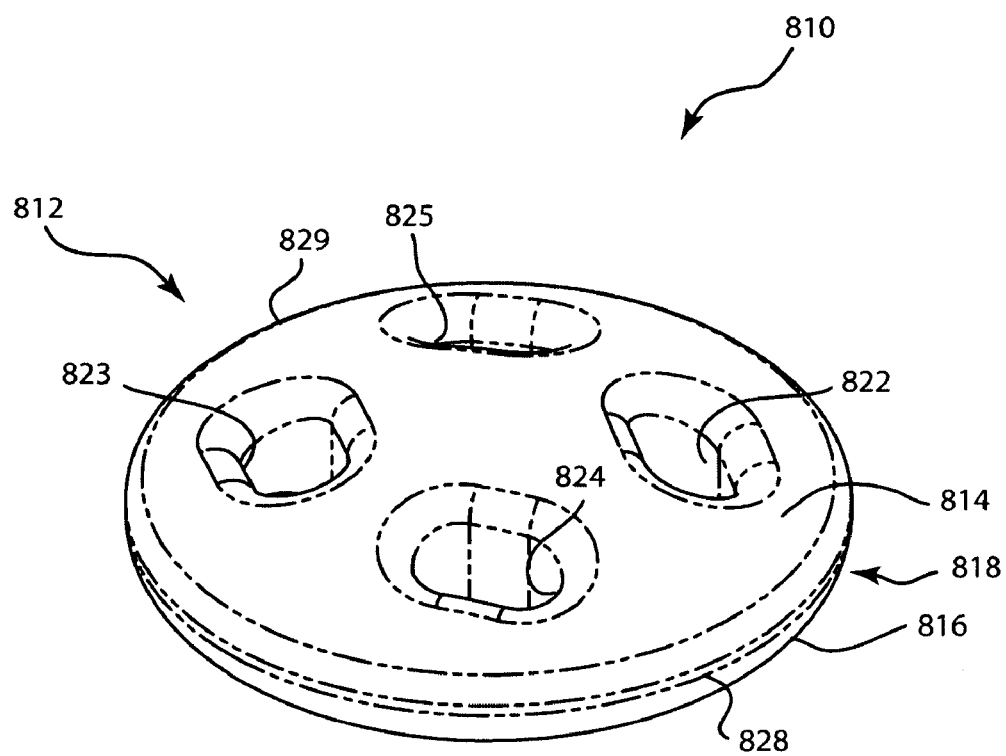
FIG. 30 is a perspective view of a line lock according to another alternative embodiment of the invention.

Referring to FIG. 30, a perspective view illustrates a line lock 810 according to another alternative embodiment of the invention. As in previous embodiments, the line lock 810 has a body 812 with a generally disc-like shape. The body 812 has a top surface 814, a bottom surface 816, and a periphery 818 extending between the top surface 814 and the bottom surface 816 to define the generally circular profile of the body 812. The body 812 bounds a first primary passageway 822, a second primary passageway 823, a first secondary passageway 824, and a second secondary passageway 825. All of the primary and secondary passageways 822, 823, 824, 825 are positioned proximate the periphery 818. However, the body 812 does not bound any working passageways.

The primary and secondary passageways 822, 823, 824, 825 are shaped in a manner similar to those of the embodiment of FIG. 19, and may thus be somewhat elongated to permit them to receive a doubled-over suture end or the like. Since no working passageways are present, the suture 350 may pass outside the periphery 818, and may rest against the periphery 818 in place of the bore of a working passageway.

For example, the standing portion of the suture 350 (not shown in FIG. 30) may extend from the bottom surface 816. The first locking portion 356 may pass through the first primary passageway 822, then through the first secondary passageway 824 to define the first compression section 360, and then around a first working portion 828 of the periphery 818. Similarly, the second locking portion 357 may pass through the second primary passageway 823, then through the second secondary passageway 825 to define the second compression section 361, and then around a second working portion 829 of the periphery. Although the suture 350 is not illustrated in FIG. 30, the pattern applied to the suture 350 by engagement with the line lock 810 may be similar to that of FIGS. 32 and 33, which will be described subsequently. Alternatively, the pattern applied to the suture 350 by engagement of the line lock 810 may be similar to that of FIGS. 35 and 36, which will also be described subsequently.

When the line lock 810 is locked, the compression sections 360, 361 may press the working portions 354, 355 of the suture against the top surface 814. The working portions 354, 355 must bend around the working portions 828, 829 of the periphery 818, which serve to provide friction in addition to bending. If desired, the working portions 828, 829 may be sharpened, notched, or otherwise shaped to enhance the magnitude of friction they provide. As in other embodiments, the working portions 354, 355 also frictionally engage the compression sections 360, 361. The line lock 810 of FIG. 30 is relatively compact, and may be especially useful for tissue retention in highly constrained spaces.

Figure 31:
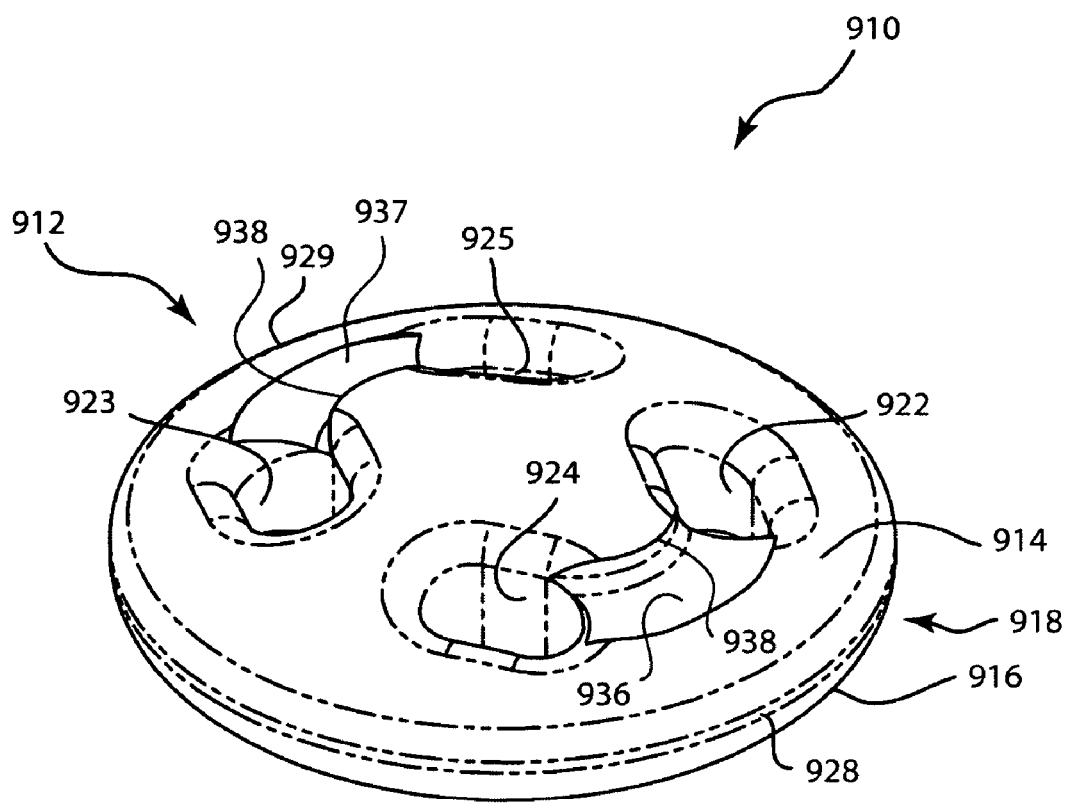
FIG. 31 is a perspective view of a line lock according to another alternative embodiment of the invention.

Referring to FIG. 31, a perspective view illustrates a line lock 910 according to another alternative embodiment of the invention. The line lock 910 has a body 912 with a disc-like shape. The body 912 may have a top surface 914, a bottom surface 916, and a periphery 918 that extends between the top surface 914 and the bottom surface 916 to define the generally circular profile of the body 912. As in the previous embodiment, the body 912 bounds a first primary passageway 922, a second primary passageway 923, a first secondary passageway 924, and a second secondary passageway 925.

Working passageways have again been omitted, and the periphery 918 includes first and second working portions 928, 929 along which the suture 350 may be routed in place of working passageways. Additionally, the body 912 has a first groove 936 extending between the first primary and secondary passageways 922, 924, and a second groove 937 extending between the second primary and secondary passageways 923, 925. The grooves 936, 937 define sharpened lips 938 where they intersect the top surface 914. The sharpened lips 938 face outward, and each of the sharpened lips 938 has a generally arcuate shape similar to the generally arcuate shape of each of the grooves 936, 937.

Figure 32:
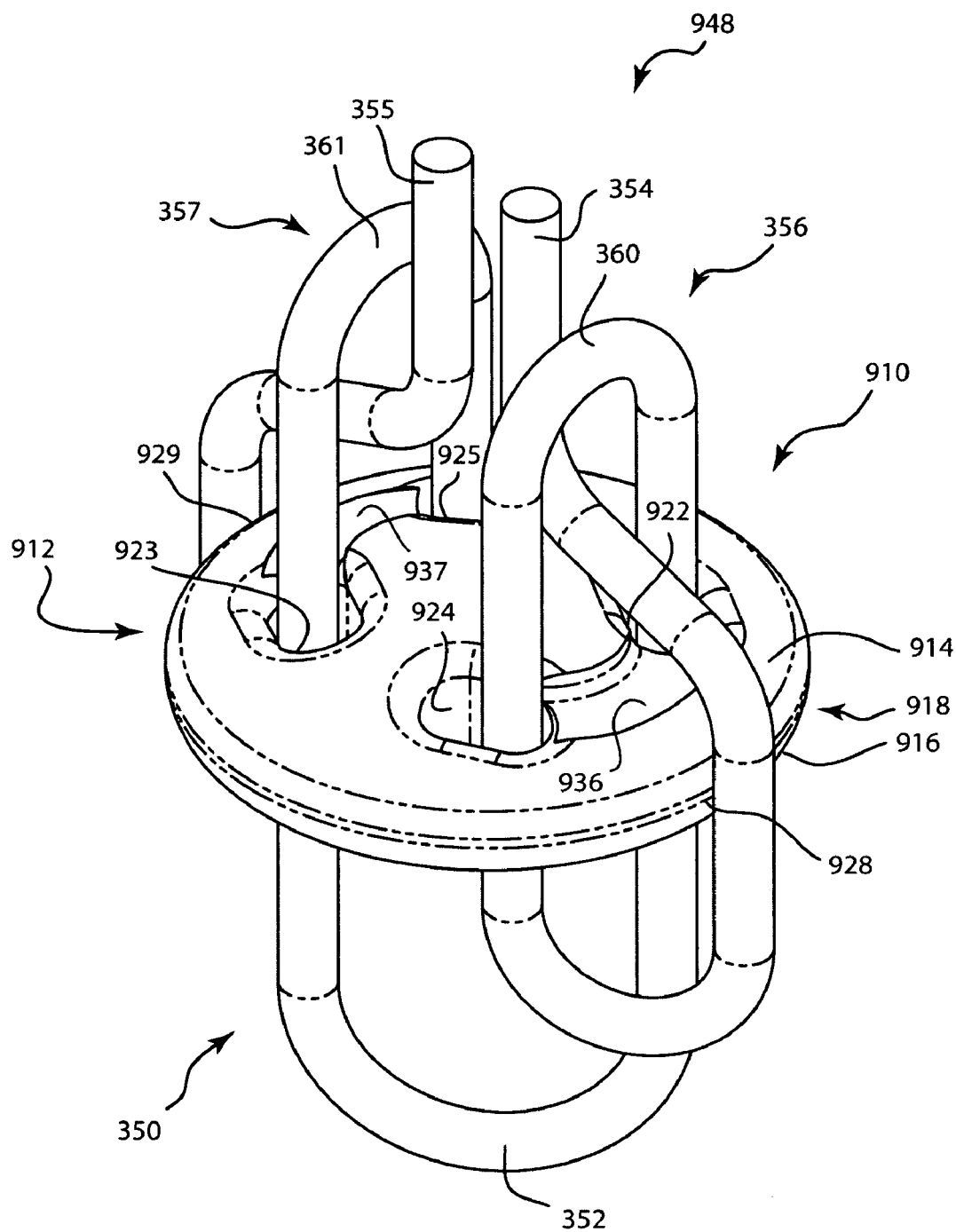
FIG. 32 is a perspective view of the line lock of FIG. 31, with a suture passing loosely through the passageways of the line lock.

Referring to FIG. 32, a perspective view illustrates a system 948 including the line lock 910 and the suture 350, with the suture 350 passing relatively loosely through the passageways 922, 923, 924, 925 of the line lock 910. As shown, the first locking portion 356 passes through the first primary passageway 922, then the first secondary passageway 924, thereby defining the first compression section 360 of the suture 350. Similarly, the second locking portion 357 passes through the second primary passageway 923, then through the second secondary passageway 925 to define the second compression section 361 of the suture 350.

The first locking portion 356 then passes around the first working portion 928 of the periphery 918, and then between the top surface 914 and the first compression section 360. By the same token, the second locking portion 357 then passes around the second working portion 929 of the periphery 918, and then between the top surface 914 and the second compression section 361.

Figure 33:
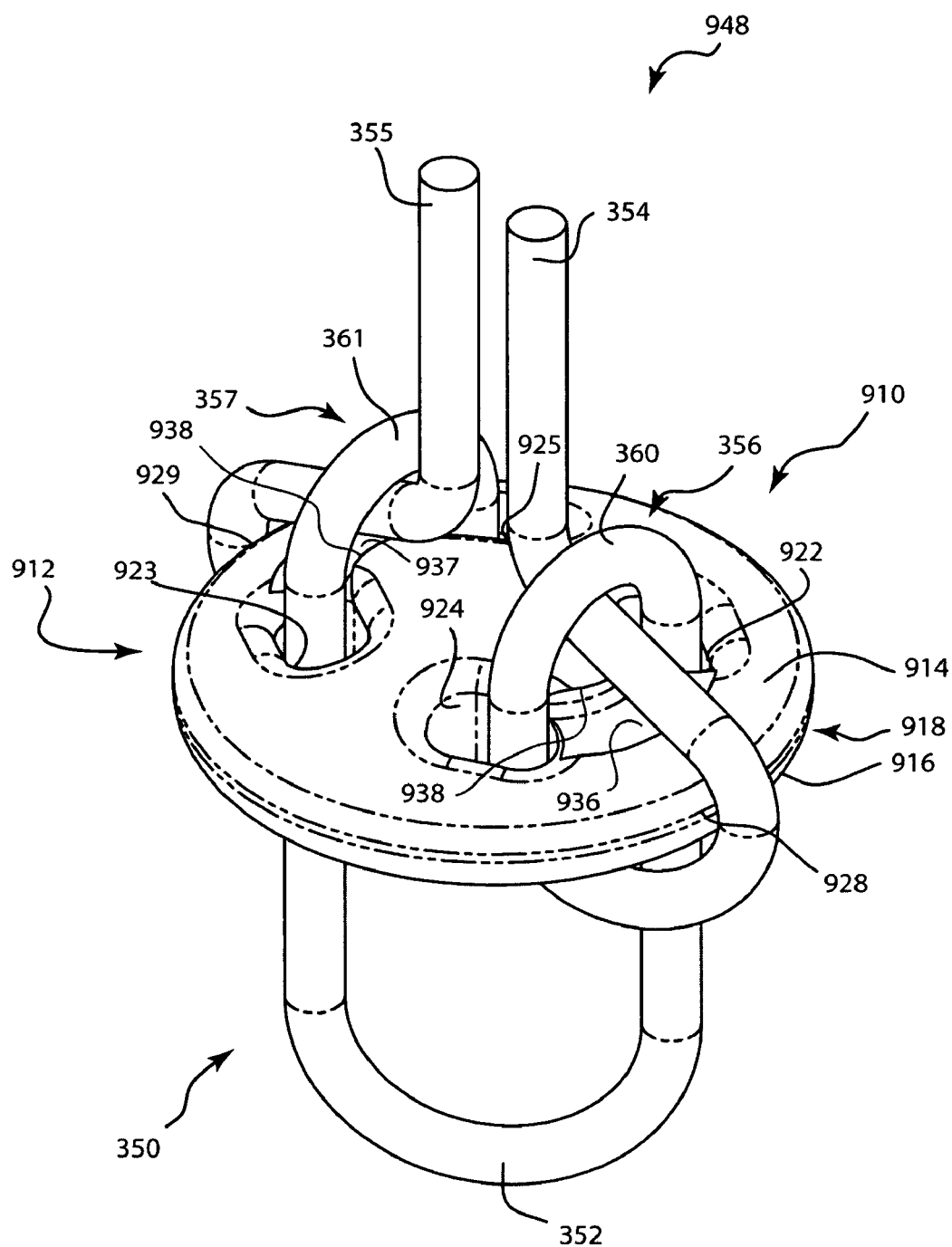
FIG. 33 is a perspective view of the line lock of FIG. 31 with suture passing tightly through the passageways of the line lock.

Referring to FIG. 33, a perspective view illustrates the system 948 of FIG. 32, with the suture 350 passing relatively tightly through the passageways 922, 923, 924, 925 of the line lock 910. When the standing portion 352 tightens, the compression sections 360, 361 press the working portions 354, 355 of the suture 350 against the grooves 936, 937 and the top surface 914, including the sharpened lips 938. The sharpened lips 938 provide bends in the working portions 354, 355, and also exert frictional force on the working portions 354, 355 to keep them from moving toward the working portions 928, 929 of the periphery 918. The compression sections 360, 361 may slide into the grooves 936, 937 to enhance bending of the working portions 354, 355.

Figure 34:
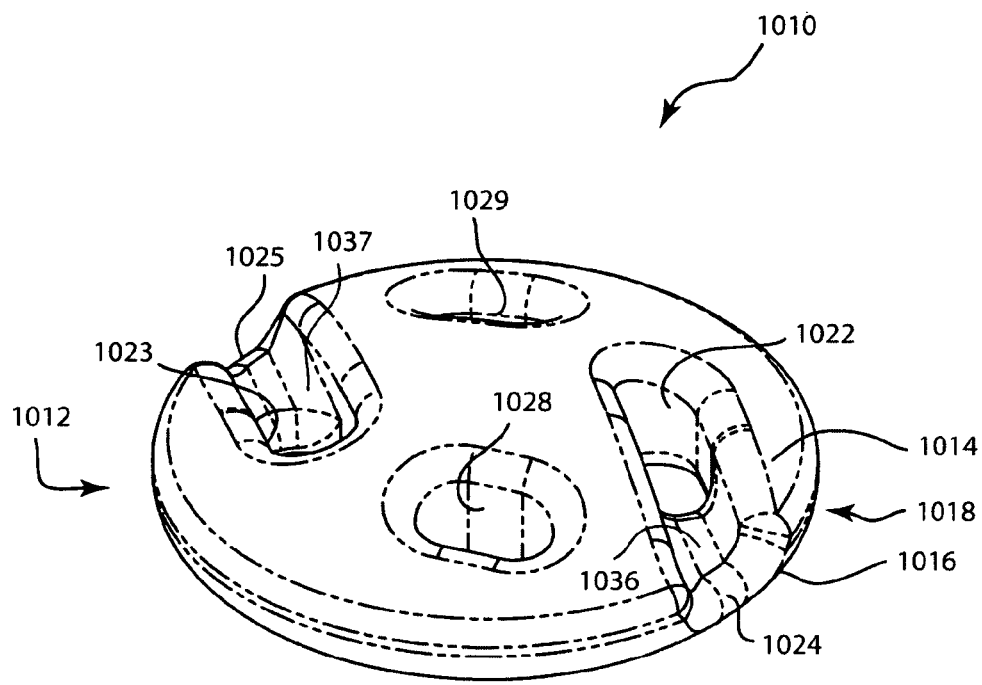
FIG. 34 is a perspective view of a line lock according to another alternative embodiment of the invention.

Referring to FIG. 34, a perspective view illustrates a line lock 1010 according to another alternative embodiment of the invention. The line lock 1010 has a body 1012 with a disc-like shape. The body 1012 has a top surface 1014, a bottom surface 1016, and a periphery 1018 extending between the top surface 1014 and the bottom surface 1016 to provide the generally circular profile of the body 1012. The body 1012 bounds a first primary passageway 1022 and a second primary passageway 1023.

Furthermore, the body 1012 partially bounds a first secondary passageway 1024 and a second secondary passageway 1025. In the embodiment of FIG. 34, the secondary passageways 1024, 1025 take the form of notches formed in the periphery 1018. As mentioned previously, the term "passageway," as used in this application, is broadly interpreted to include partially bound apertures, open channels, recesses, grooves, slots, and the like, that are capable of receiving a line and at least partially retaining the line therein. Accordingly, the structures labeled by reference numbers 1024, 1025 of FIG. 34 are, indeed, passageways. The secondary passageways 1024, 1025 are contiguous with the periphery 1018 because the bore of each of the secondary passageways 1024, 1025 transitions directly into the periphery 1018, with no significant intervening surface.

The body 1012 also bounds a first working passageway 1028 and a second working passageway 1029. The primary passageways 1022, 1023 and the working passageways 1028, 1029 may be shaped similarly to the primary and secondary passageways 322, 323, 324, 325 of the embodiment of FIG. 19, in that they are slightly elongated to permit passage of a doubled-over suture end. The body 1012 also has a first groove 1036 extending between the first primary passageway 1022 and the first secondary passageway 1024, and a second groove 1037 extending between the second primary passageway 1023 and the second secondary passageway 1025.

Figure 35:
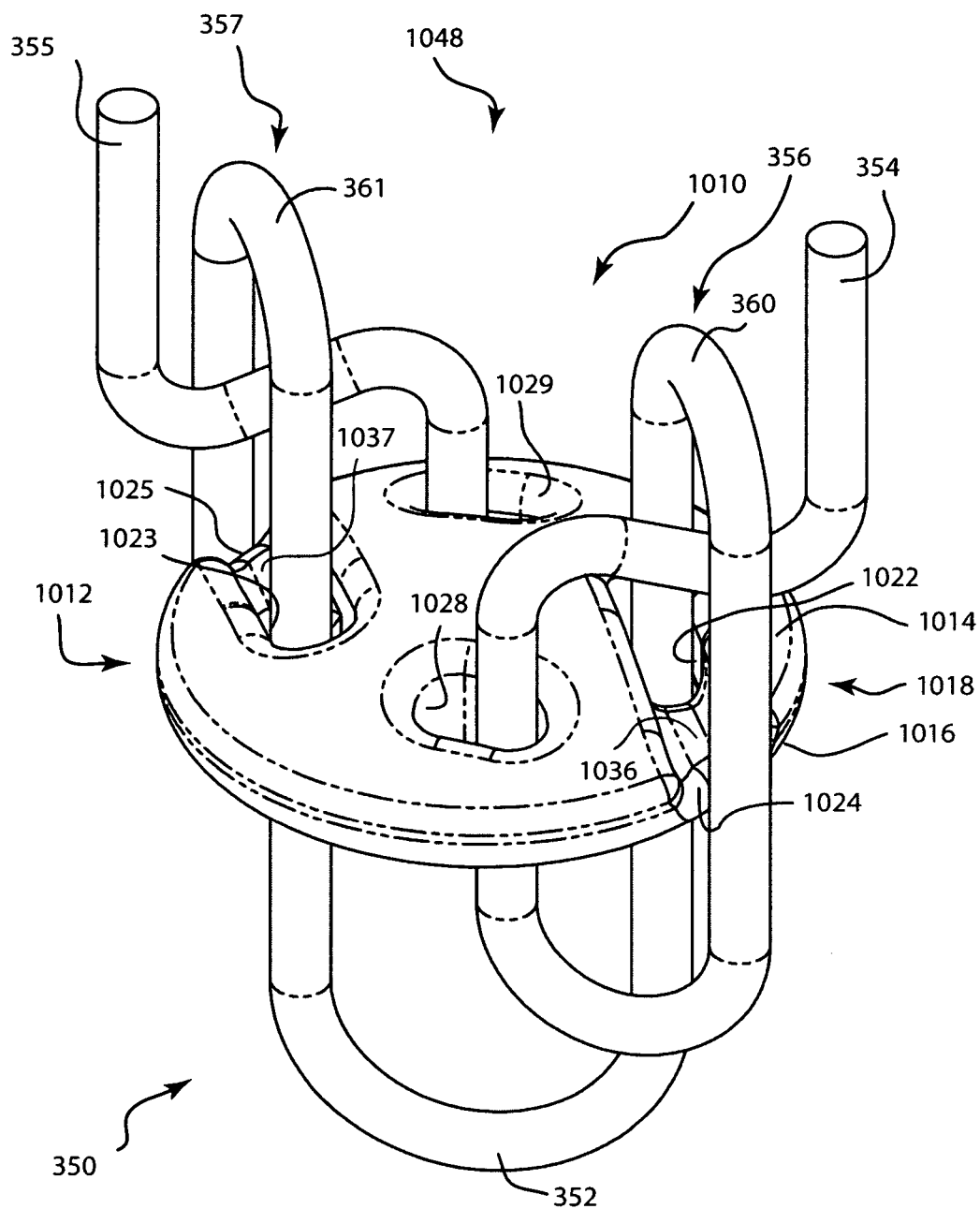
FIG. 35 is a perspective view of the line lock of FIG. 34, with a suture passing loosely through the passageways of the line lock.

Referring to FIG. 35, a perspective view illustrates a system 1048 including the line lock 1010 of FIG. 34 and the suture 350 passing relatively loosely through the passageways 1022, 1023, 1024, 1025, 1028, 1029 of the body 1012. As shown, the first locking portion 356 of the suture 350 extends through the first primary passageway 1022, then through the first secondary passageway 1024 to define the first compression section 360. Similarly, the second locking portion 357 extends through the second primary passageway 1023, then through the second secondary passageway 1025 to define the second compression section 361.

From the first secondary passageway 1024, the first locking portion 356 extends through the first working passageway 1028, and then between the first compression section 360 and the top surface 1014 and the first groove 1036. Similarly, from the second secondary passageway 1025, the second locking portion 357 extends through the second working passageway 1029, and then between the second compression section 361 and the top surface 1014 and the second groove 1037.

Figure 36:
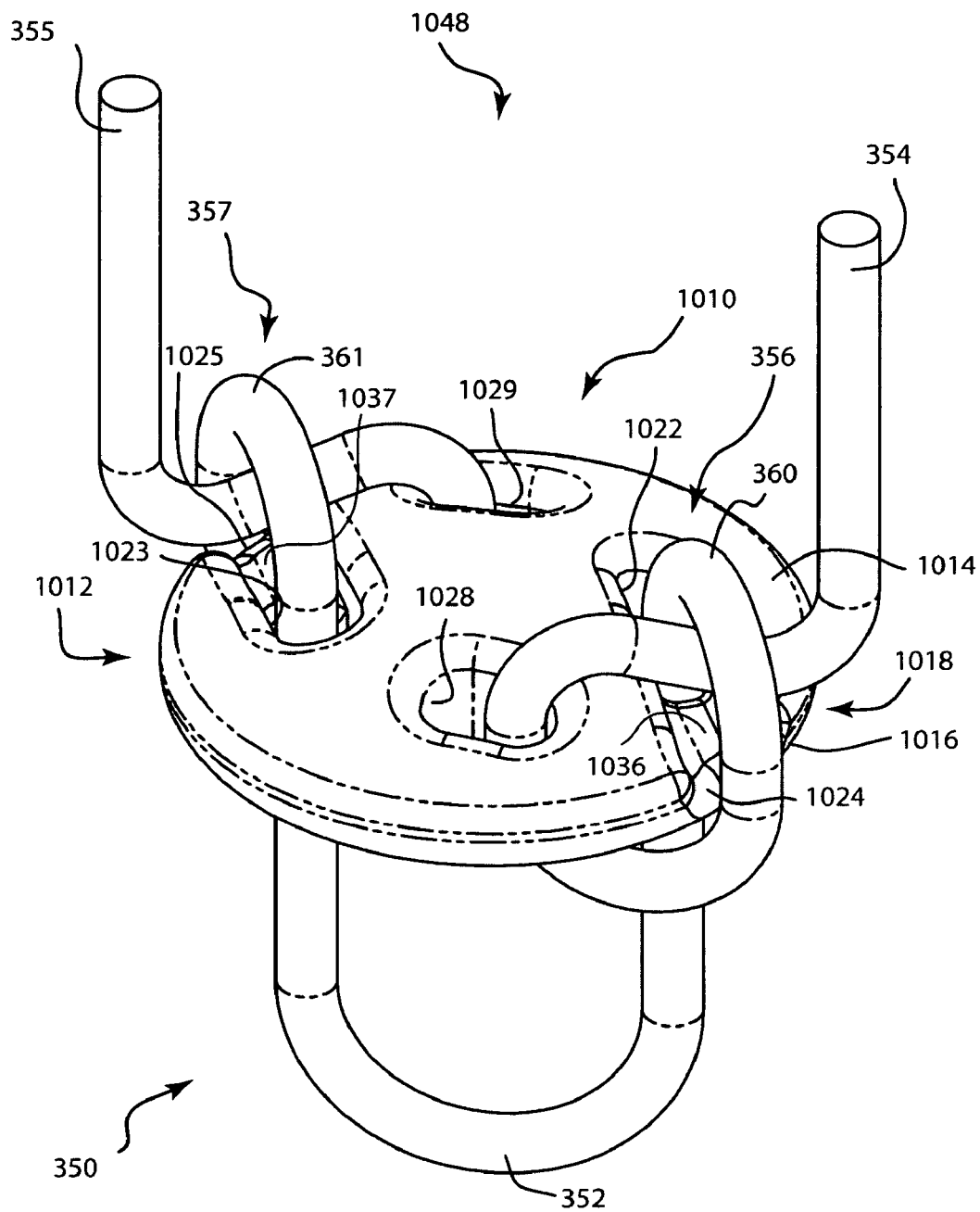
FIG. 36 is a perspective view of the line lock of FIG. 34 with suture passing tightly through the passageways of the line lock.

Referring to FIG. 36, a perspective view illustrates the system 1048 of FIG. 35, with the suture 350 passing relatively tightly through the passageways 1022, 1023, 1024, 1025, 1028, 1029 of the body 1012. When the standing portion 352 is tensioned, the compression sections 360, 361 press the working portions 354, 355 against the top surface 1014 and the grooves 1036, 1037. The working portions 354, 355 lie generally perpendicular to the grooves 1036, 1037 and are pressed into the grooves 1036, 1037 to form a pair of bends in each of the working portions 354, 355. The edges of the grooves 1036, 1037 also exert frictional force on the working portions 354, 355 to keep them from moving toward the working passageways 1028, 1029.

Figure 37:
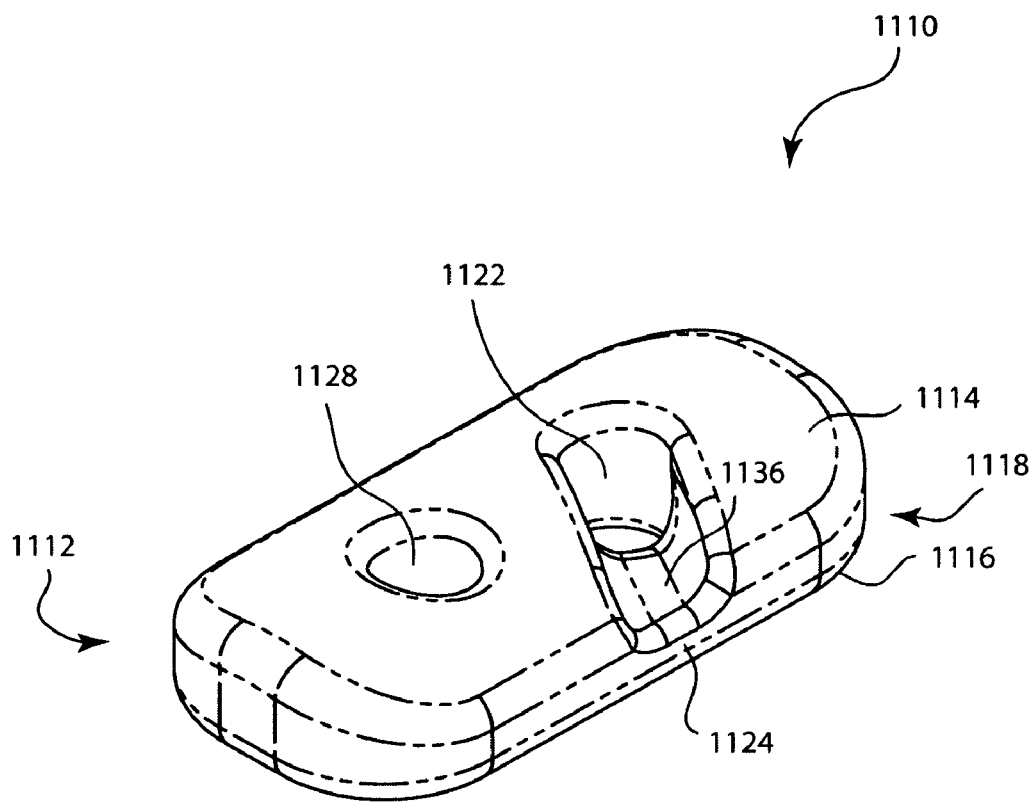
FIG. 37 is a perspective view of a line lock according to another alternative embodiment of the invention.

Referring to FIG. 37, a perspective view illustrates a line lock 1110 according to another embodiment of the invention. As shown, the line lock 1110 has a body 1112 with a generally rectangular prismatic shape, with rounded corners. The body 1112 has a top surface 1114, a bottom surface 1116, and a periphery 1118 extending between the top surface 1114 and the bottom surface 1116 to define the generally rectangular profile of the body 1112. The body 1112 at least partially bounds a plurality of passageways that enable the body 1112 to perform the function of half of the line lock 1010 of the previous embodiment, as will be set forth in greater detail below.

The passageways of the body 1112 include a first primary passageway 1122 fully bounded by the body 1112, a first secondary passageway 1124 partially bounded by the body 1112, and a first working passageway 1128 fully bounded by the body 1112. The first primary, secondary, and working passageways 1122, 1124, 1128 are similar to their counterparts 1022, 1024, 1028 from the previous embodiment, and operate to retain the suture 350 in a similar manner. Additionally, the body 1112 includes a first groove 1136 similar to the first groove 1036 of the previous embodiment.

Figure 38:
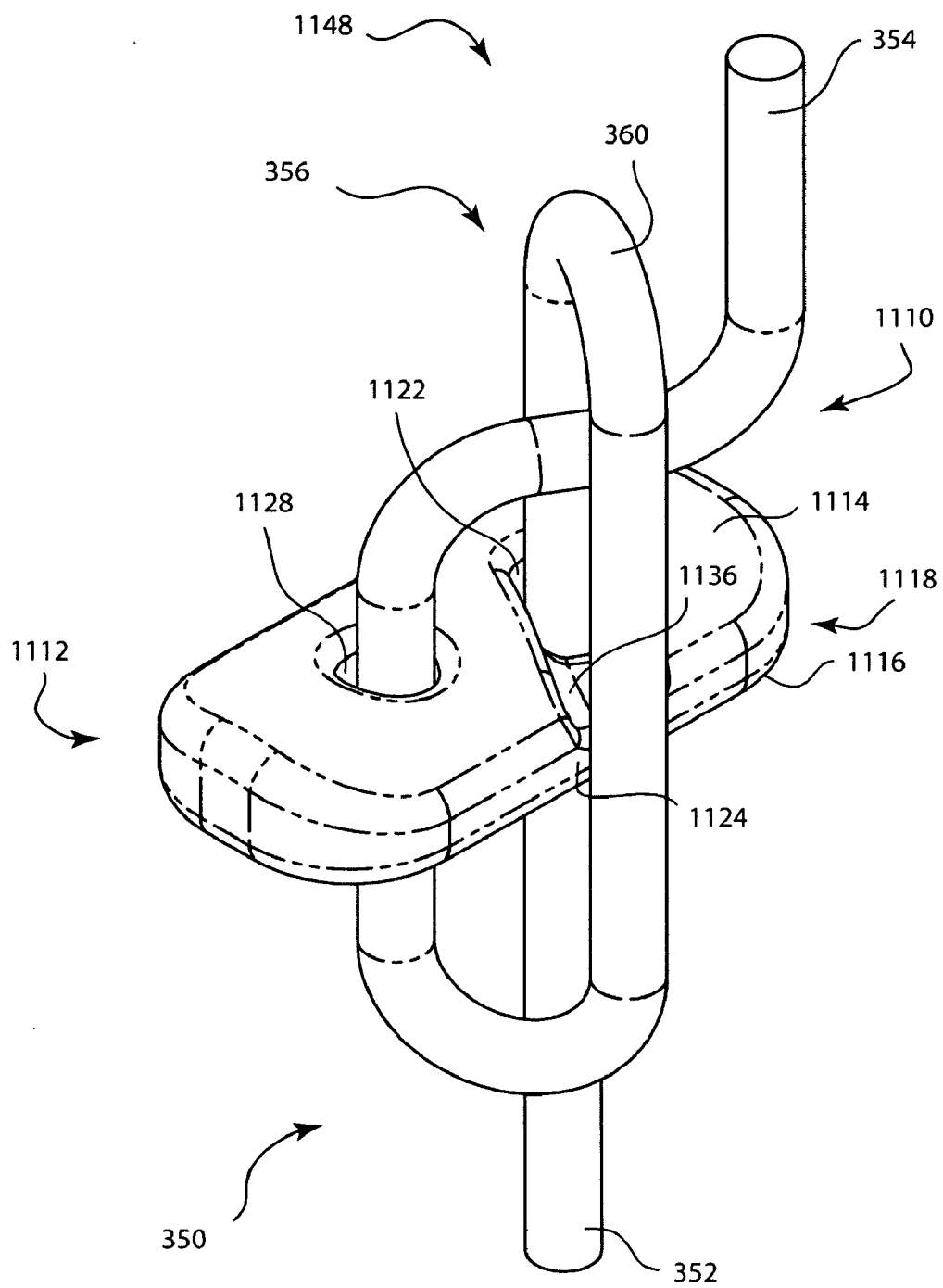
FIG. 38 is a perspective view of the line lock of FIG. 37, with a suture passing loosely through the passageways of the line lock.

Referring to FIG. 38, a perspective view illustrates a system 1148 including the line lock 1110 and the suture 350 passing relatively loosely through the passageways 1122, 1124, 1128 of the body 1112. The first locking portion 356 of the suture 350 passes through the first primary passageway 1122, then through the first secondary passageway 1124 to define the first compression section 360 of the suture 350. The first locking portion 356 then passes through the first working passageway 1128. From the first working passageway 1128, the first working portion 354 passes between the first compression section 360 and the top surface 1114 and the first groove 1136.

Figure 39:
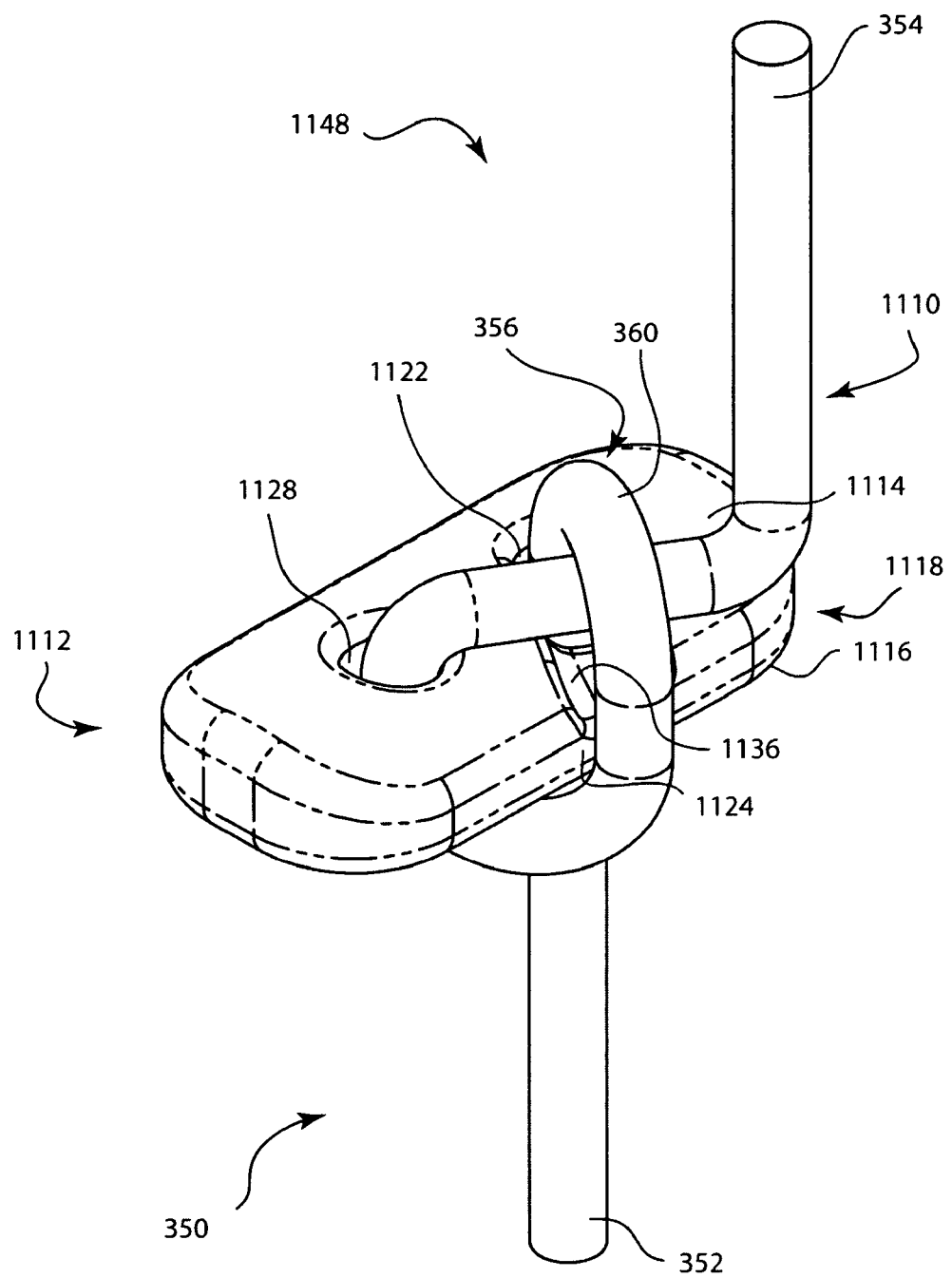
FIG. 39 is a perspective view of the line lock of FIG. 37 with suture passing tightly through the passageways of the line lock.

Referring to FIG. 39, a perspective view illustrates the system 1148 of FIG. 38, with the suture 350 passing relatively tightly through the passageways 1122, 1124, 1128. When the standing portion 352 is tensioned, the first compression section 360 presses the first working portion 354 against the top surface 1114 and the first groove 1136. As in the previous embodiment, the first groove 1136 helps to form bends in the first working portion 354 and to exert frictional force to keep the first working portion 354 from moving back toward the first working passageway 1128. Thus, as in previous embodiments, the first locking portion 356 is only able to move through the passageways 1122, 1124, 1128 along one direction.

In FIGS. 38 and 39, the working portion 352 is shown as an end, not a loop. However, the suture 350 need not terminate at the working portion 352 as shown, but may a continue to provide the second locking portion 357 including the second compression section 361, and then the second working portion 355 (not shown in FIG. 38), as illustrated in connection with previous embodiments. The working portion 352 may then form a loop, and a second line lock (not shown) similar to the line lock 1110 may be used to lockably retain the second locking portion 357. Thus, the two line locks may cooperate to retain tissue.

Alternatively, the working portion 352 may indeed terminate with no loop. The working portion 352 may instead be tied or otherwise attached to an anchor or the like, so that the line lock 1110 can be used to cinch tissue along the standing portion 352 by moving along only one length of the suture 350. Since the line lock 1110 is only made to retain one length of the suture 350, the line lock 1110 may be relatively compact by comparison with previous embodiments, and may thus be especially useful for tissue retention in constrained spaces.

Figure 40:
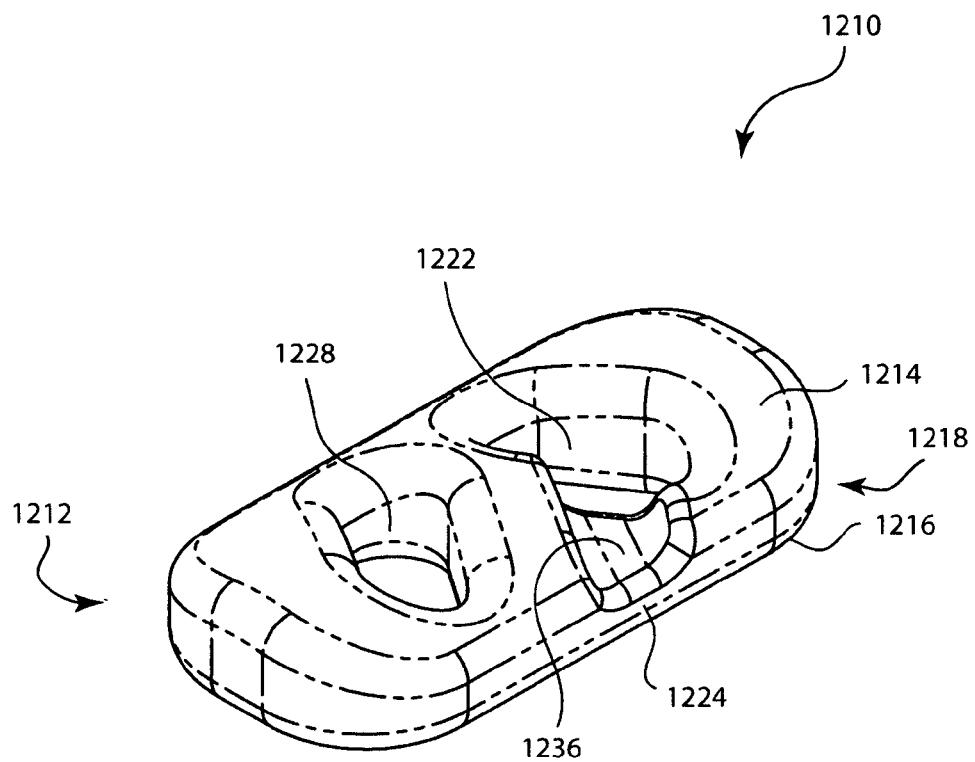
FIG. 40 is a perspective view of a line lock according to another alternative embodiment of the invention.

Referring to FIG. 40, a perspective view illustrates a line lock 1210 according to another alternative embodiment of the invention. As in the previous embodiment, the line lock 1210 has a body 1212 with a generally rectangular prismatic shape, with rounded corners. The body 1212 has a top surface 1214, a bottom surface 1216, and a periphery 1218 extending between the top surface 1214 and the bottom surface 1216 to define the generally rectangular profile of the body 1212. The body 1212 is configured similarly to the body 1112 of the previous embodiment, except that the body 1212 has passageways sized to simultaneously receive and lock multiple suture lengths.

More precisely, the body 1212 bounds a first primary passageway 1222, partially bounds a first secondary passageway 1224, and bounds a first working passageway 1228. The first primary and working passageways 1222, 1228 are elongated so as to be capable of simultaneously receiving multiple suture lengths. The first secondary passageway 1224 is only partially bounded by the body 1212, and may therefore be able to receive multiple suture lengths without elongation. As in the previous embodiment, the body 1212 also includes a first groove 1236 that extends between the first primary and secondary passageways 1222, 1224.

Figure 41:
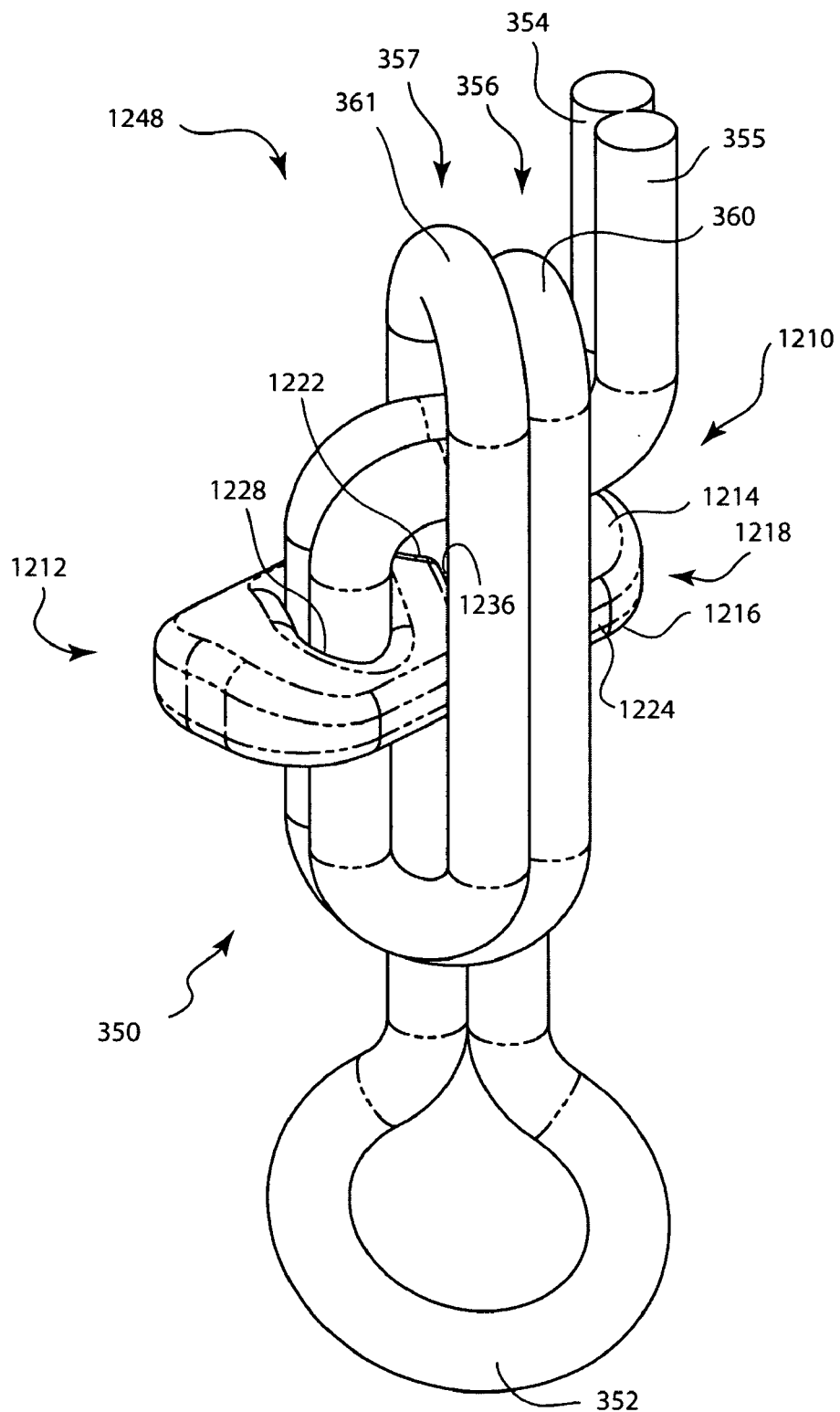
FIG. 41 is a perspective view of the line lock of FIG. 40, with a suture passing loosely through the passageways of the line lock.

Referring to FIG. 41, a perspective view illustrates a system 1248 including the line lock 1210 and the suture 350, with the suture 350 passing relatively loosely through the passageways 1222, 1224, 1228 of the body 1212. FIG. 41 illustrates the standing portion 352, both working portions 354, 355, and both locking portions 356, 357 of the suture 350, including both compression sections 360, 361. The standing portion 352 is again illustrated as a loop.

As shown, the locking portions 356, 357 are routed through the passageways 1222, 1224, 1228 side-by-side. More precisely, the locking portions 356, 357 pass through the first primary passageway 1222, then through the first secondary passageway 1224 to define the first and second compression sections 360, 361. The locking portions 356, 357 then pass through the first working passageway 1228. From the first working passageway 1228, the working portions 354, 355 pass between the compression sections 360, 361 and the top surface 1214 and the first groove 1236.

Figure 42:
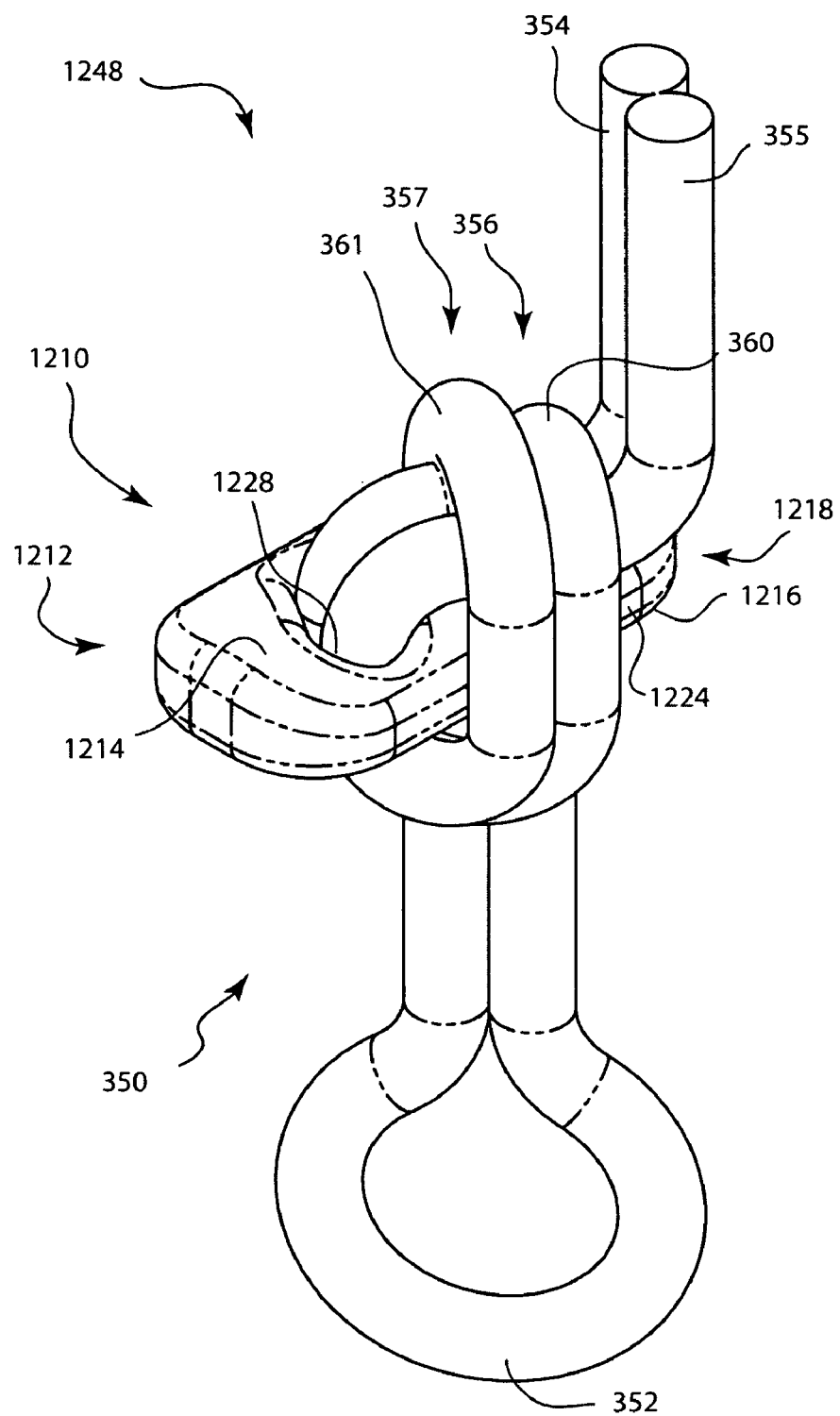
FIG. 42 is a perspective view of the line lock of FIG. 40 with suture passing tightly through the passageways of the line lock.

Referring to FIG. 42, a perspective view illustrates the system 1248 of FIG. 41, with the suture 350 relatively tightly passing through the passageways 1222, 1224, 1228 of the body 1212. The compression sections 360, 361 press the working portions 354, 355 against the top surface 1214 and the first groove 1236. The first groove 1236 helps to form bends in the working portions 354, 355 and to exert frictional force to keep the first working portions 354, 355 from moving back toward the first working passageway 1228. Thus, as in previous embodiments, the locking portions 356, 357 are only able to move through the passageways 1222, 1224, 1228 along one direction. As in previous embodiments, the standing portion 352 may pass through an anchor or the like to enable usage of the line lock 1210 for tissue retention.

The present invention has particular relevance to surgery, and more particularly to tissue retention through the use of sutures. However, the principles, structures, and methods of the present invention may also be extended to other fields, including the use of larger line locks for locking ropes or cables in a wide variety of applications.

While the present invention has application to any need for securing a line, it is particularly advantages to surgical suture applications as a way to conveniently and reliable replace the need to tie suture knots. The advantage is even greater in arthroscopic and endoscopic applications, where sophisticated sliding knots followed by "back-up" knots must be tied outside of a cannula and slid into final position at an internal body site. The sophisticated sliding knots are difficult to tie, time consuming, and bulky. The present invention provides an easy to apply, quick to deliver, and low profile solution that will reliably maintain the desired suture tension.

The present invention may be embodied in other specific forms without departing from its spirit or essential characteristics. For example, above are described various alternative examples of different adjustable line locks. It is appreciated that various features of the line locks can be mixed and matched to form a variety of other alternatives. As such the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A system for retaining tissue, the system comprising:
a line lock comprising a body at least partially bounding a plurality of passageways; and
a suture routed through the passageways such that a first locking portion of the suture is able to be drawn along a pathway through at least some of the passageways fully bounded by the body, along only one direction along the pathway defined by the routing of the suture, wherein the first locking portion is routed through the passageways such that a first compression section of the first locking portion presses another part of the first locking portion against the line lock in response to tension urging the first locking portion to move through the passageways opposite to the one direction;
wherein the suture is further routed through the passageways such that a second locking portion of the suture is able to be drawn through at least some of the passageways substantially along only a second direction, wherein the second locking portion is spaced apart from the first locking portion.

2. The system of claim 1, wherein the passageways are arranged such that the first and second locking portions extend along pathways that are symmetrical across a plane extending through a center of the body.

3. The system of claim 1, wherein the passageways are arranged such that the first and second locking portions extend along pathways that are symmetrical about an axis extending through a center of the body.

4. The system of claim 1, wherein the body comprises a generally circular profile within a plane extending substantially perpendicular to at least one of the passageways.

5. The system of claim 1, wherein the passageways comprise a first primary passageway, a first secondary passageway, and a first working passageway, wherein the passageways cooperate to receive the first locking portion along a first pathway extending through the first primary passageway, then the first secondary passageway, and then the first working passageway such that the first locking portion is able to be drawn along the first pathway toward the first working passageway, but not toward the first primary passageway.

6. The system of claim 5, wherein the passageways further comprise a second working passageway, wherein first primary and secondary passageways and the second working passageway cooperate to receive the second locking portion along a second pathway extending through one of the first primary and secondary passageways, then the other of the first primary and secondary passageways, and then the second working passageway.

7. The system of claim 5, wherein the body comprises a top surface, wherein the first working passageway comprises a capture slot, wherein at least part of the first locking portion lies along the top surface in response to tightening of the first locking portion to directly press a portion of the suture into the capture slot to resist motion of the first locking portion toward the first primary passageway.

8. The system of claim 7, wherein the first working passageway is fully bounded by the body.

9. The system of claim 7, wherein the body further comprises a first groove positioned proximate the first primary and secondary passageways such that, in response to tension on the first locking portion, a portion of the suture extending nonparallel to the groove is pressed against the groove to enhance retention of the first locking portion by the line lock.

10. The system of claim 1, wherein the second locking portion comprises a second compression section that presses another part of the second locking portion against the line lock in response to tension urging the second locking portion to move through the passageways opposite to the second direction, the suture further comprising a first working portion, a second working portion, and a standing portion, wherein the first locking portion extends from the first working portion to the standing portion, and the second locking portion extends from the second working portion to the standing portion.

11. The system of claim 10, wherein the passageways are arranged such that the body advances along the standing portion in response to tension drawing the first and second working portions in substantially opposite directions.

12. The system of claim 10, wherein the body comprises a top surface and an opposing bottom surface, wherein the first and second locking portions are received by the passageways along pathways selected to provide four spaced apart bends of the suture on the top surface and two bends of the suture on the bottom surface.

13. The system of claim 1, wherein the suture further comprises a first working portion, a second working portion, and a standing portion, wherein the first locking portion extends from the first working portion to the standing portion, and the second locking portion extends from the second working portion to the standing portion, the system further comprising an insertion tool having a hollow bore sized to receive the first and second working portions to facilitate advancement of the body along the standing portion.

14. A system for retaining tissue, the system comprising:
a line lock comprising a body at least partially bounding a first primary passageway and a first secondary passageway; and
a suture routed and drawn through the first primary and secondary passageways along one direction along a pathway defined by the routing of the suture;
wherein the first locking portion is routed through the passageways such that a first compression section of the first locking portion presses another part of the first locking portion against the line lock in response to tension urging the first locking portion to move through the passageways opposite to the one direction;
wherein the first primary and secondary passageways are further shaped and arranged such that, while the first locking portion extends through the first primary and secondary passageways, a second locking portion of the suture can be inserted through the first primary and secondary passageways along a second path;
wherein the first and second locking portions are spaced apart from each other.

15. The system of claim 14, wherein the passageways are arranged such that the first and second locking portions extend along pathways that are symmetrical to each other with respect to a center of the body.

16. The system of claim 14, wherein the body comprises a generally circular profile within a plane extending substantially perpendicular to at least one of the passageways.

17. The system of claim 14, wherein the line lock further at least partially bounds a first working passageway, wherein the passageways cooperate to receive the first locking portion along a first pathway extending through the first primary passageway, then the first secondary passageway, and then the first working passageway such that the first locking portion is able to be drawn along the first pathway toward the first working passageway, but not toward the first primary passageway.

18. The system of claim 17, wherein the line lock further at least partially bounds a second working passageway, wherein the first primary passageway, the first secondary passageway, and the second working passageway cooperate to receive the second locking portion along a second pathway extending through one of the first primary and secondary passageways, then through the other of the first primary and secondary passageways, and then through the second working passageway.

19. The system of claim 14, the suture further comprising a first working portion, a second working portion, and a standing portion, wherein the first locking portion extends from the first working portion to the standing portion, and the second locking portion extends from the second working portion to the standing portion.

20. The system of claim 14, wherein the suture further comprises a first working portion, a second working portion, and a standing portion, wherein the first locking portion extends from the first working portion to the standing portion, and the second locking portion extends from the second working portion to the standing portion, the system further comprising an insertion tool having a hollow bore sized to receive the first and second working portions to facilitate advancement of the body along the standing portion.

21. A system for retaining tissue, the system, comprising:
a line lock comprising a body at least partially bounding a first primary passageway and a first secondary passageway;
a suture routed and drawn along a first pathway through the first primary and secondary passageways, along only one direction defined by routing of the suture, to define a compression section of the suture, the compression section extending between the first primary and secondary passageways to span a displacement between the passageways, such that the compression section presses another part of the suture against the line lock in response to tension urging the suture to move through the passageways opposite to the one direction;
wherein the body further comprises a groove positioned proximate the first primary and secondary passageways such that, in response to tension on the compression section, the compression section directly presses a portion of the suture against the groove to cause retention of the portion by the line lock.

22. The system of claim 21, wherein the body further comprises second primary and secondary passageways, wherein the second passageways are arranged symmetrically to the first passageways with respect to a center of the body.

23. The system of claim 21, wherein the body comprises a generally circular profile within a plane extending substantially perpendicular to at least one of the passageways.

24. The system of claim 21, wherein the body further at least partially bounds a first working passageway, wherein the passageways cooperate to receive the suture along the first pathway extending through the first primary passageway, then the first secondary passageway, and then the first working passageway such that the suture is able to be drawn along the first pathway toward the first working passageway, but not toward the first primary passageway.

25. The system of claim 24, wherein the body comprises a top surface, wherein the first working passageway comprises a capture slot, wherein at least part of the suture lies along the top surface in response to tension in the compression section to directly press a portion of the suture into the capture slot to resist motion of the suture toward the first primary passageway.

26. The system of claim 21, further comprising a suture having the compression section, the suture further comprising a first working portion, a second working portion, and a standing portion, the body further comprising a top surface and an opposing bottom surface, wherein the working portion extends from the top surface and the standing portion extends from the bottom surface such that the line lock is able to be advanced along the standing portion.

27. The system of claim 26, further comprising an insertion tool having a hollow bore sized to receive the first and second working portions to facilitate advancement of the body along the standing portion.

28. The system of claim 21, wherein the passageways are further arranged such that the portion of the suture extends nonparallel to the groove.

29. The system of claim 28, wherein the groove is oriented substantially parallel to the displacement between the passageways such that the compression section extends substantially parallel to the groove.

\* \* \* \* \*

UNITED STATES PATENT AND TRADEMARK OFFICE
CERTIFICATE OF CORRECTION

PATENT NO. : 7,566,339 B2
APPLICATION NO. : 10/936376
DATED : July 28, 2009
INVENTOR(S) : T. Wade Fallin and M. Mary Sinnott Page 1 of 2

It is certified that error appears in the above-identified patent and that said Letters Patent is hereby corrected as shown below:

Column 1, Line 55, ADD "the" after "over" currently reads "line lock over suture" should read --line lock over the suture--.

Column 2, Line 12, ADD "the" before "line" currently reads "view of line lock" should read --view of the line lock--.

Column 8, Line 11, DELETE "capture" should be changed to --captured--.

Column 8, Line 51, DELETE "cause" should be changed to --causes--.

Column 9, Line 17, DELETE "relative" should be changed to --relatively--.

Column 11, Line 35, ADD "the" before "suture" currently reads "portion 104 of suture" should read --portion 104 of the suture--.

Column 11, Line 53, DELETE "end" should be changed to --ends--.

Column 13, Line 27, DELETE "tension" should be changed to --tensioned--.

Column 14, Line 12, DELETE "bound" should be changed to --bounds--.

Column 14, Line 39, ADD "a" after "capture" currently reads "at capture slot" should read --at a capture slot--.

Column 15, Line 10, ADD "a" before "monofilament" currently reads "is monofilament line" should read --is a monofilament line--.

Column 15, Line 25, ADD "to" after "cooperate" currently reads "to cooperate receive" should read --to cooperate to receive--.

Signed and Sealed this
Twentieth Day of September, 2011

David J. Kappos
*Director of the United States Patent and Trademark Office*

CERTIFICATE OF CORRECTION (continued)
U.S. Pat. No. 7,566,339 B2

Column 15, Line 55, DELETE "324, 324" should be changed to --324, 325--.

Column 21, Line 63, DELETE "622. 624" should be changed to --622, 624--.

Column 23, Line 19, ADD "." after "735" currently reads "trough 735" should read --trough 735.--.

Column 27, Line 67, DELETE "advantage" should be changed to --advantageous--.

Column 28, Line 1, DELETE "reliable" should be changed to --reliably--.

Column 30, Line 47, Claim 21, ADD "and" after "passageway;" currently reads "passageway; a suture" should read --passageway; and a suture--.

Column 30, Line 48, Claim 21, DELETE "and drawn" after "routed" currently reads "suture routed and drawn along" should read --suture routed along--.